United States Patent
Berzal Herranz et al.

(10) Patent No.: US 9,938,532 B2
(45) Date of Patent: Apr. 10, 2018

(54) MOLECULES INHIBITING THE HUMAN IMMUNODEFICIENCY VIRUS TYPE 1 (HIV-1), METHOD FOR THE PRODUCTION THEREOF AND APPLICATIONS OF SAME

(71) Applicants: CONSEJO SUPERIOR DE INVESTIGACIONES CIENTÍFICAS (CSIC), Madrid (ES); INSTITUTO NACIONAL DE TÉCNICA AEROESPACIAL "ESTEBAN TERRADAS", Torrejón de Ardoz, Madrid (ES)

(72) Inventors: Alfredo Berzal Herranz, Granada (ES); Carlos Briones Llorente, Madrid (ES); Francisco José Sánchez-Luque, Granada (ES); Susanna Cuevas Manrubia, Madrid (ES); Michael Stich, Madrid (ES)

(73) Assignees: CONSEJO SUPERIOR DE INVESTIGACIONES CIENTÍFICAS (CSIC), Madrid (ES); INSTITUTO NACIONAL DE TÉCNICA AEROESPACIAL "ESTEBAN TERRADAS", Madrid (ES)

( * ) Notice: Subject to any disclaimer, the term of this patent is extended or adjusted under 35 U.S.C. 154(b) by 0 days.

(21) Appl. No.: 14/646,573

(22) PCT Filed: Nov. 22, 2013

(86) PCT No.: PCT/ES2013/070809
§ 371 (c)(1),
(2) Date: Sep. 24, 2015

(87) PCT Pub. No.: WO2014/080061
PCT Pub. Date: May 30, 2014

(65) Prior Publication Data
US 2016/0017332 A1 Jan. 21, 2016

(30) Foreign Application Priority Data
Nov. 23, 2012 (ES) .................................. 201231819

(51) Int. Cl.
*C12N 15/115* (2010.01)
*C12N 15/10* (2006.01)
*G01N 33/569* (2006.01)

(52) U.S. Cl.
CPC ........ *C12N 15/115* (2013.01); *C12N 15/1048* (2013.01); *G01N 33/56988* (2013.01); *C12N 2310/16* (2013.01); *C12N 2310/3519* (2013.01); *C12N 2320/30* (2013.01); *G01N 2469/10* (2013.01)

(58) Field of Classification Search
None
See application file for complete search history.

(56) References Cited

U.S. PATENT DOCUMENTS

2008/0318210 A1* 12/2008 Bentwich ............... C12Q 1/703
435/6.11

FOREIGN PATENT DOCUMENTS

WO 96/27605 9/1996

OTHER PUBLICATIONS

Watrin et al., "In Vitro Selection of RNA Aptamers Derived from a Genomic Human Library against the TAR RNA Element of HIV-1", Biochemistry, vol. 48, 2009, pp. 6278-6284.
Briones et al., "Applications of peptide nucleic acids (PNAs) and locked nucleic acids (LNAs) in biosensor development", Anal Bioanal Chem, vol. 402, 2012, pp. 3071-3089.
Ducongé et al., "In vitro selection identifies key determinants for loop-loop interactions: RNA aptamers selective for the TAR RNA element of HIV-1", RNA, vol. 5, 1999, pp. 1605-1614.
Ellington et al., "In vitro selection of RNA molecules that bind specific ligands", Articles, Nature, vol. 346, Aug. 1990, pp. 818-822.
Geyer et al., "Nucleobase Pairing in Expanded Watson-Crick-like Genetic Information Systems", Structure, vol. 11, Dec. 2003, pp. 1485-1498.
Good et al., "Expression of small, therapeutic RNAs in human cell nuclei", Gene Therapy, vol. 4, 1997, pp. 45-54.
Horvath et al., "An Automate DNA Synthesizer Employing Dexynucleoside 3'-Phosphoramidites", Methods in Enzymology, vol. 154, pp. 314-326.
Huthoff et al., "Two alternating structures of the HIV-1 leader RNA", RNA, vol. 7, 2001, pp. 143-157.
Joyce, "Directed evolution of Nucleic Acid Enzymes", Annu. Rev. Biochem, vol. 73, 2004, pp. 791-836.

(Continued)

*Primary Examiner* — Tracy Vivlemore
(74) *Attorney, Agent, or Firm* — Wenderoth, Lind & Ponack, L.L.P.

(57) ABSTRACT

The invention relates to an aptamer, the structure thereof comprising at least one nucleotide sequence 5'-GGCA(A/G)GGA-3', that can specifically bind to the poly(A) hairpin of the 5'UTR region of the genome of the human immunodeficiency virus type 1 (HIV-1), providing the method for producing aptamers with said sequence by means of a combination of experimental techniques of in vitro selection of nucleic acids with computational techniques of sequence optimization. The invention also relates to a DNA gene structure for synthesizing said aptamers, preferably RNA. The invention further relates to the different uses of the above-mentioned aptamer, including the use thereof as a biosensor molecule for detecting and/or quantifying HIV-1, as an inhibitor of the production of viral particles of HIV-1, and to the application thereof in medicine, the invention also relating to a method for treating a disease caused by HIV-1, and to a pharmaceutical composition comprising said aptamer.

15 Claims, 21 Drawing Sheets

(56) References Cited

OTHER PUBLICATIONS

Figure 1:
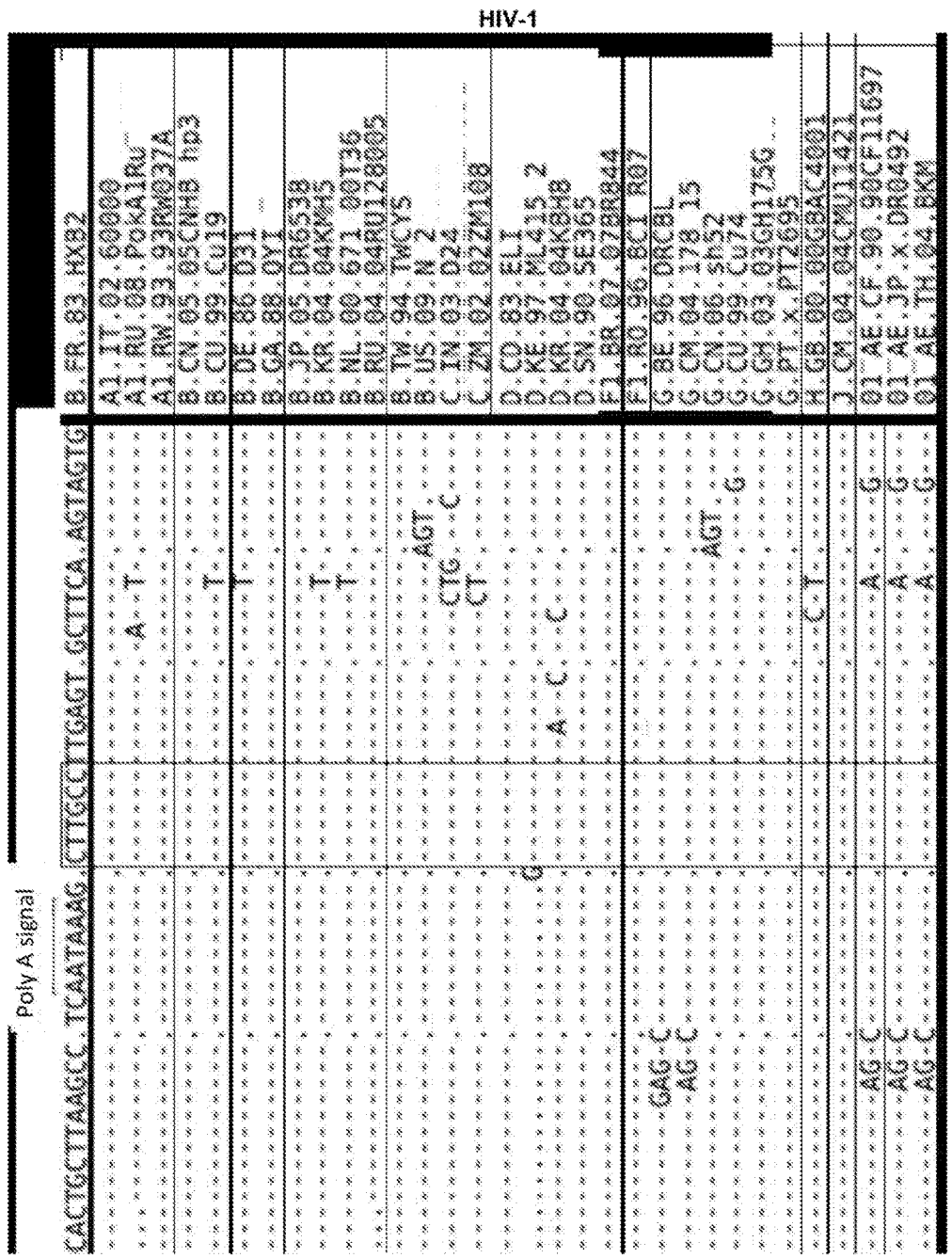
Figure 1:
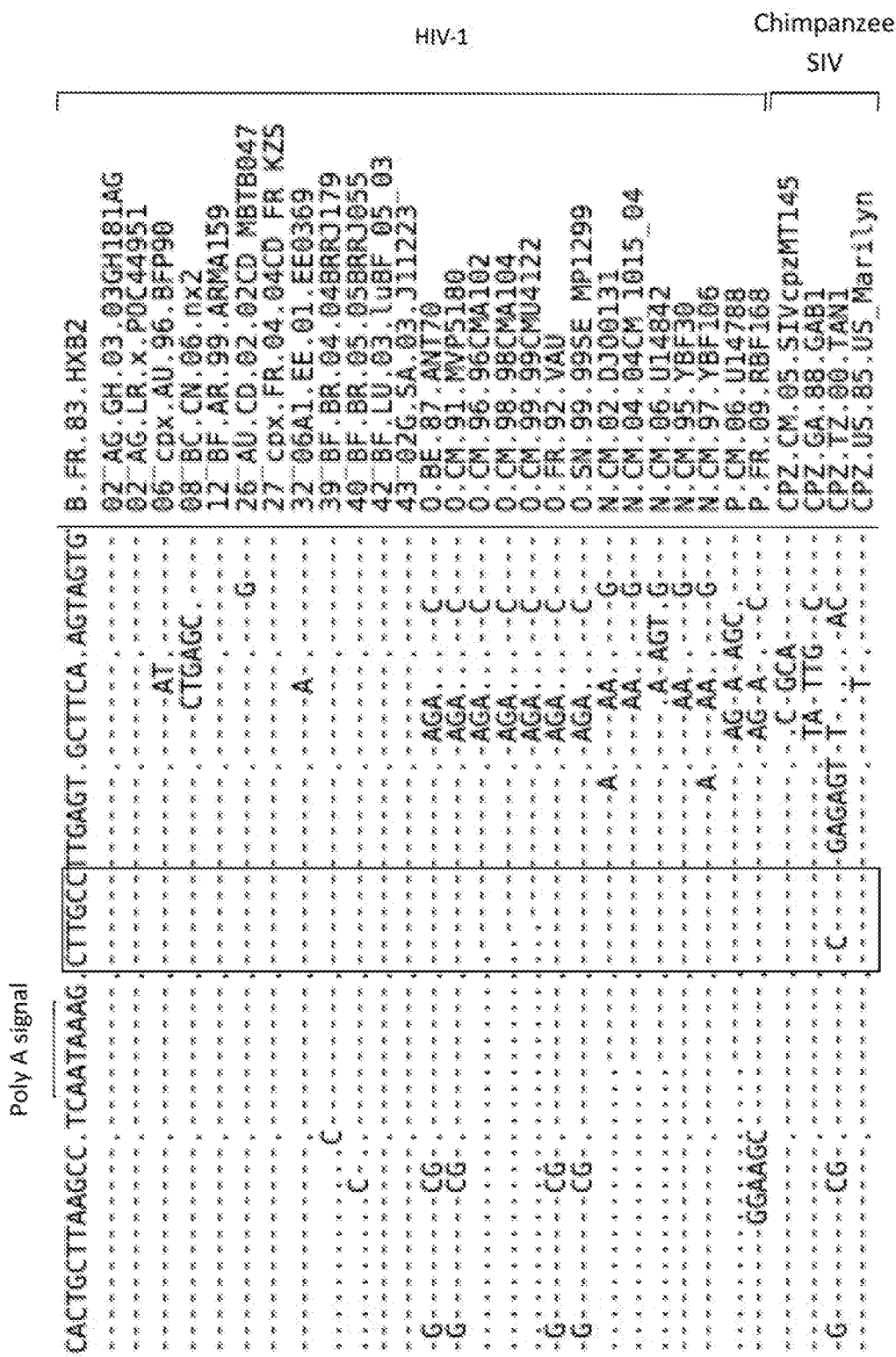

Carothers et al., Ed., "A hepatitis C virus (HCV) internal ribosome entry site (IRES) domain III-IV-targeted aptamer inhibits translation by binding to an apical loop of domain IIId", Nucleic Acids Research, vol. 33, No. 2, 2005, pp. 683-692.
Klussmann et al., "In Vitro Selection of Functional Oligonucleotides and the Origins of Biochemical Activity", The Aptamer Handbook, pp. 1-490.
Kolb et al., "Endogenous Expression of an Anti-TAR Aptamer Reduces HIV-1 Replication", RNA Biology, vol. 3, Issue 4, 2006, pp. 150-156.
Kuiken et al., Ed., HIV Sequence Compendium 2011, National Institutes of Health, pp. 1-438.
Lauridsen et al., "Enzymatic Recognition of 2'-Modified Ribonucleoside 5'-Triphosphates: Towards the Evolution of Versatile Aptamers", Chem Bio Chem, vol. 13, 2012, pp. 19-25.
Mathews et al., "Expanded Sequence Dependence of Thermodynamic Parameters Improves Prediction of RNA Secondary Structure", J. Mol. Biol., vol. 288, 1999, pp. 911-940.
Pinheiro et al., "Synthetic Genetic Polymers Capable of Heredity and Evolution", Science, vol. 336, Apr. 20, 2012, pp. 341-344.
Romero-López et al., "Interfering with hepatitis C virus IRES activity using RNA molecules identified by a novel in vitro selection method", Biol. Chem., vol. 386, Feb. 2005, pp. 183-190.
Sánchez-Luque et al., "Inhibition of HIV-1 Replication and Dimerization Interference by Dual Inhibitory RNAs", Molecules, vol. 15, 2010, pp. 4757-4772.
Tuerk et al., "Systematic Evolution of Ligands by Exponential Enrichment: RNA Ligands to Backeriophage T4 DNA Polymerase", Science, New Series, vol. 249, No. 4968, Aug. 3, 1990, pp. 505-510.
International Search Report dated Feb. 25, 2014 in International (PCT) Application No. PCT/ES2013/070809.
Boucard et al., "Bimodal Loop-Loop Interactions Increase the Affinity of RNA Aptamers for HIV-1 RNA Structures", Biochemistry, vol. 45, Jan. 12, 2006, pp. 1518-1524.
Reyes-Darias et al., "HIV RNA dimerisation interference by antisense oligonucleotides targeted to the 5' UTR structural elements", Virus Research, vol. 169, Jul. 20, 2012, pp. 63-71.
Berkhout et al., "RNA: Structure Metabolism and Catalysis: In Vitro Evidence That the Untranslated Leader of the HIV-1 Genome Is an RNA Checkpoint That Regulates Multiple Functions through Conformational Changes", J. Biol. Chem., vol. 277, No. 22, May 31, 2002, pp. 19967-19975.
Parkash et al., "Inhibition of 5'-UTR RNA Conformational Switching in HIV-1 Using Antisense PNAs", PLOS One, vol. 7, Issue 11, e49310, Nov. 2012, pp. 1-12.
John J. Turner et al., "Targeting the HIV-1 RNA leader sequence with synthetic oligonucleotides and siRNA: Chemistry and cell delivery", Biochimica et Biophysica Acta (BBA), 2006, vol. 1758, No. 3, pp. 290-300.
Sequence 5094 from Patent EP 2402463 from Database EMBL.
Sequence 366983 from Patent EP 1572962 from Database EMBL.
NaldimiR-206 AS preparation method related PCR reverse primer, SEQ: 13, from Database GENESEQ.

* cited by examiner

FIG. 6

| | |
|---|---|
| IX03-1 | GGGAAUUCAAGACAACGACAUAGUGGCAAGGACUAUGGAGUGAUCUGAUACUACGAGCUCGAC |
| IX24-1 | GGGAAUUCAAGACAGAGCUCCAUGUGGCAAGGUGCAUGGAGUGAUCUGAUAUCUACGAGCUCGAC |
| IX36-1 | GGGAAUUCAACACCACUAUGUGUGGCAAGCAUGGAGUGGAUCUGAUACUACGAGCUCGAC |
| X02-1 | GGGAAUUCAACAUUCAAGCAGUGGCAGCAUGGAGCAAUGGAGUAAUGGAGCAAUCUGAUACUACGAGCUCGAC |
| X04-2 | GGGAAUUCAAGACUACGGCAGUGGCAAGGACUAUGGAGCAAUCGAUACUACGAGCUCGAC |
| X09-1 | GGGAAUUCAACACCACUAUUGUUGGCAAGGAGUACAAUGGAGUGAUGGAUACUACGAGCUCGAC |
| X10-7 | GGGAAUUCAAGACUAGUGCAAGGUAGCAAUGCGUAGCAAUGCGUAGCAAUGGAUCAACUACGAGCUCGAC |
| X13-1 | GGGAAUUCAAGACUAUACCAUGGUGGCAAGCAACAAUGGAGUGAUCUGAUAUCUACGAGCUCGAC |
| X36-1 | GGGAAUUCAAGUACGCAAGGAGUACAAUGGAGUGAUCUGAUACUACGAGCUCGAC |
| X41-2 | GGGAAUUCAAGACUACUGCAUGCGUGGCAAGGACGAUGGAGUGAUCUGAUACUACGAGCUCGAC |
| XI1-17 | GGGAAUUCAACACCACUAUGUGUGGCAAGGAAGCAAUGGAGUGAUCUGAUAUACUACGAGCUCGAC |
| XI21-7 | GGGAAUUCAAGACCAAGGAGUACAAUGGAGUGAUCUGAUACUACGAGCUCGAC |
| XI23-3 | GGGAAUUCAAGACUACGUGGCAAGGACGAAUGGAGUGAUCUGAUACUACGAGCUCGAC |
| XII41-2 | GGGAAUUCAACACAACCUGGUGGCAAGGAACCCAAUGGAGAACAAUGGAGUGAUCUGAUACUACGAGCUCGAC |
| XII13-1 | GGGAAUUCAAGACACAGAAUAAGCACAUACUACCUGGGUGGCAAGGUGUGGAUGAUCUGAUAUCUACGAGCUCGAC |
| XI101-1 | GGGAAUUCAACAACUACUACCUGGUGGCAAGGAACCCAAUGGAGUGAUCUGAUAUACUACGAGCUCGAC |
| XI149-1 | GGGAAUUCAACACAACCACCUGAUUGGCAAGGACGAAACAAUGGAGUACAAUGGAGUGAUCUGAUAUACUACGAGCUCGAC |
| XI107-1 | GGGAAUUCAAGACUAGUGUGGCAAGGACUAAUGGAGUGAUCUGAUAUACUACGAGCUCGAC |
| XI129-1 | GGGAAUUCAAGACUACGUGUGGCAAGGAGUACAAUGGAGUGAUCUGAUAUCUACGAGCUCGAC |
| XIV22-23 | GGGAAUUCAACACCACUAUUGUGUGGCAAGGAAGCAAUGGAGCAAUGGAUGAUCUGAUAUACUACGAGCUCGAC |
| XIV26-6 | GGGAAUUCAACACAACACCUAUGGCAAGGAGUACCCAAUGGAGUGAUCUGAUAUCUACGAGCUCGAC |
| XIV1-2 | GGGAAUUCAACACCUGGGUGCAGGCAAGGAAGUAAAUGGAGUACAAUGGAGUGAUCUGAUAUCUACGAGCUCGAC |
| XIV32-1 | GGGAAUUCAAGACUACGGCAGUGGCAAGGACGUACAAUGGAGUACAAUGCGCAGUGAUCUGAUAUCUACGAGCUCGAC |
| XIV5-1 | GGGAAUUCAAGACUACGGCAGUGGCAAGGACGAAUGGAGCAAUGGAGUGAUCUGAUAUCUACGAGCUCGAC |
| XIV12-1 | GGGAAUUCAACACCGCUAUUGUUGGCAAGGAAGCAAUGGAGUGAUCUGAUAUACUACGAGCUCGAC |

Consensus motif: NNDYGCARGGARNNN
((((............))))

MOLECULES INHIBITING THE HUMAN IMMUNODEFICIENCY VIRUS TYPE 1 (HIV-1), METHOD FOR THE PRODUCTION THEREOF AND APPLICATIONS OF SAME

FIELD OF THE ART

The present invention relates to the field of aptamers (nucleic acid molecules obtained by selection or evolution in vitro, possessing the ability to specifically bind to a certain molecular target) and their use for the treatment of infections caused by the human immunodeficiency virus type 1 (HIV-1). Therefore, the present invention is framed in the field of biotechnology, and specifically in the field of development and manufacture of pharmaceutical compositions for the treatment of diseases caused by HIV-1. The present invention may also result in a product of interest in the field of gene therapy, as well as in the development of diagnostic systems for HIV-1.

STATE OF THE ART

HIV is the causative agent of acquired immunodeficiency syndrome (AIDS), a disease that affects the immune system of humans and causes inactivation thereof. Of the two different species of HIV, the so-called "human immunodeficiency virus type 1 (HIV-1)" is more virulent than the "type 2" (HIV-2), and is, in fact, the most widespread in the world. HIV infection is already described as pandemic. According to data from the World Health Organization, in 2010 about 34 million people worldwide were HIV-positive, around 2.7 million new infections were detected and there were approximately 1.8 million deaths as a consequence of HIV infection (www.who.int/hiv/data/2011_epi_core_en.png). Of all HIV-positive people, only 6.6 million were receiving antiretroviral therapy.

HIV is a retrovirus and is characterized, as all members of the family Retroviridae, by an alternation between phases with RNA and DNA genome in its viral cycle. The genomic RNA of HIV-1 has three major coding regions called gag, pol and env (in a 5' to 3' order) flanked by two untranslated regions or UTRs. The gag gene encodes the proteins of the viral nucleocapsid and the matrix (called p17, p24 and p7); pol encodes enzymes for processing the viral genetic material and their gene products (reverse transcriptase or RT, protease or PR, and integrase or IN); and env encodes the glycoproteins gp120 (surface protein) and gp41 (transmembrane), responsible for the infection and viral tropism. HIV also has a number of accessory genes (tat, rev, nef, vpr, vif and vpu) typical of lentiviruses and exerting regulatory roles allowing, among other things, the infection of non-proliferative cells. The 5'UTR of the viral RNA is particularly relevant because it has a number of highly conserved structural domains among the different viral isolates. These domains are actively involved in key processes such as transcription, reverse transcription, messenger RNA processing or packaging of the viral genomic RNA into the infectious particles. The 5'UTR can be folded in two alternative conformations, called LDI and BMH (Huthoff and Berkhout, 2001). A fact relevant to the present invention is that, depending on the folding adopted by the 5'UTR, other genomic structural domains are or are not exposed. Said domains perform essential functions for the virus, such as the case of the poly-A or DIS domains. This structural transition may play a role in the regulation of viral processes.

The highly active antiretroviral therapy (HAART) has emerged as the most effective treatment of the disease: no cure is achieved but the reduction in viral load is evident in a high percentage of infected patients, allowing some restoration of the immune function. It has also been shown that HAART reduces the spread of the virus from the sick treated individual and prevents the spread to healthy treated individuals at risk. This therapy consists of a combination of two or more antiretroviral drugs, which are chemical compounds of a different nature usually designed to inhibit viral enzymes (RT, PR or IN), or to interfere with the adhesion phase between the proteins of the viral envelope and the receptors of its target cell (mainly macrophages and T lymphocytes). The appropriate treatment recommendations are published annually, along with an indication of which of the combinations of drugs are most appropriate in each case (aidsinfo.nih.gov/guidelines). Major pharmaceutical companies such as Roche, Merck or GlaxoSmithKline currently distribute several of these drugs.

Another field of research relevant to the present invention is that of aptamers which are nucleic acid molecules obtained by selection or evolution in vitro and possessing the ability to specifically bind to a certain molecular target. In 1990 the development of the technology of in vitro selection of RNA, in which the ability of RNA to specifically bind to a target molecule was used as selective pressure, was reported in two separate papers. The process based on cycles of selection and amplification was designated "Systematic Evolution of Ligands by EXponential Enrichment" or SELEX (Tuerk and Gold, 1990), and the term "aptamer" (from the Latin word aptus, which means fit) was coined to denote the RNA molecules generated by this method (Ellington and Szostak, 1990).

Nowadays, the starting point of an experiment of in vitro selection of nucleic acids (RNA or DNA) is a large population of DNA molecules (typically, from $10^{12}$ to $10^{16}$) with a central region (usually, of between 20 and 100 nucleotides, nt, in length) with a random or highly mutagenized sequence. Said central region is flanked by two binding regions to specific primers (of between 12 and 20 nt in length each of them) the sequence of which is known and which will allow the enzymatic reactions required in each round: reverse transcription (RT) which carries out the passage of RNA to DNA, DNA amplification by polymerase chain reaction (PCR), and in vitro transcription (IVT) of the amplified DNA to RNA. The selection is introduced into the process allowing to pass to the next round only the nucleic acid molecules capable of binding (aptamers) to their target immobilized on a support (typically, affinity columns or nanoparticles of different type), or the molecules capable of performing a specific biochemical function. In the latter case, the molecules with catalytic capacity obtained are called "ribozymes" if they are made of RNA, or "deoxyribozymes" or "DNAzymes" if they are made of DNA. Non-functional molecules are eliminated in each round, whereas functional subpopulations can be analyzed by means of cloning and sequencing. The successive rounds of selection and amplification (usually between 6 and 15) increase the ratio between active and inactive nucleic acids present in the population until it becomes enriched in molecules having the sought phenotype (ability to bind to a target or biochemical activity). The entire process takes place in vitro, and the experimental variables can be controlled in detail. Subsequently the process of "in vitro evolution" was developed, which is distinguished from "in vitro selection" in that a source of genetic variability is continuously introduced into the population by means of mutation (usually by mutagenic PCR) and/or recombination (Joyce, 2004) in the evolution process. Thus, in vitro evolution generates new molecules in each round, whereas during in vitro selection each round deals with an active subpopulation from the previous population (having as the only source of variability the mutation rate inherent to the enzymes used).

Numerous RNA and DNA aptamers have been obtained using these systems, the affinity of which for their target sometimes exceeds that of the antibodies for their antigens. The targets recognized by the aptamers cover a wide range of molecular size and complexity from ions to full cells including small molecules (such as amino acids, nucleotides, antibiotics or metabolites), peptides, proteins, nucleic acids, macromolecular aggregates, virus or cell organelles. An additional advantage of aptamers is that their production is performed in vitro (and therefore the use of experimental animals is not required, as it is with antibodies) and the resulting nucleic acids can be modified to increase their stability or resistance to nuclease degradation. This increase in the stability of the aptamers can be achieved by means of the addition of certain chemical groups (fluoro, methyl or methoxy among them) at different positions of the nitrogenous base or nucleotide sugar, or by replacing some nucleotides of the aptamer for other units typical of nucleic acid analogue molecules (described below). Thus, in no case the nucleotide sequence of the aptamer and its functionality are altered, but an increase of the stability of the same is indeed achieved. Moreover, since they are nucleic acids, aptamers can be amplified enzymatically and are also capable of modification to incorporate different types of labeling (radioactive, fluorescent or other) and various functional groups. The experimental strategy of in vitro selection of aptamers imposes a minimum size of the molecule, which is determined by the need to incorporate fixed sequences flanking the randomized central region, and that are necessary for the binding of primer oligonucleotides required for the amplification process. This has traditionally led to the need to experimentally test the reduction of the size of the molecule, removing expendable parts and thus leading to identify, in the best case, the minimum domain with aptameric capacity. As shown below, we provide a novel aspect in this regard in the present invention, by combining classic methods of in vitro selection of nucleic acids with a bioinformatic analysis, which allows identifying potentially active domains without the need for an experimental shortening of the aptamer.

Finally, aptamers are designed to specifically bind with high affinity to its target molecule being able to, depending on the case, inducing conformational changes in the same as a result of said binding. They can also be covalently linked to ribozymes or DNAzymes to generate "catalytic aptamers" or "aptazymes" capable of performing certain biochemical functions once bound to their target (for example, cutting the target in the case that this is another RNA molecule). Thanks to all this, during the last two decades, aptamers have been gaining popularity in the field of biotechnology and biomedicine, and we are currently witnessing a steady growth in the number of applications of aptamers in diagnosis (using aptamers in dissolution or rather immobilized on various types of biosensors) and in therapy (Klussmann, 2006).

In the field of therapy, one of the applications of aptamers has been their development against targets of viral RNA. Viral genomic RNAs, mainly single stranded RNAs (ssRNA), acquire varying degrees of structural and functional complexity in their biological environments. In particular, some of its most invariant functional domains regarding the sequence and stable domains regarding the structure can be used as targets for generating aptamers against them. These aptamers have been disclosed as a powerful antiviral tool against RNA viruses such as hepatitis C (Kikuchi et al., 2005; Romero-López et al., 2005) or HIV-1 itself (Kolb et al., 2006). In the case of HIV-1, the TAR domain present in the 5'UTR (responsible for the activation of transcription and highly conserved) is a very attractive target for the use of aptamers selected against it (Duconge and Toulme, 1999; Watrin et al., 2009). The RNA aptamer "R06", with 24 nucleotides, selected against the isolated TAR domain, has been subsequently modified for its nucleolar localization and has shown an inhibition of replication of HIV-1 greater than 90% in cell culture when expressed intracellularly (Kolb et al., 2006). However, although aptamers against specific domains or subdomains of the HIV-1 5'UTR have been developed, the production process has not contemplated the fact that the proper assembly and exposition of the same in the RNA of the 5'UTR is subject to the existing balance between the two conformers described for said region (BMH and LDI; Huthoff and Berkhout, 2001) and to possible interactions with neighboring subdomains of the 5'UTR. These phenomena could be affecting the binding capacity of any aptamer, even those who behave optimally against an isolated subdomain of the 5'UTR.

Therefore, the need to develop aptamers against functional domains of the genome of HIV-1 in an environment closer to that in the genomic RNA molecule is evident. In the present invention aptamers against one or several specific subdomains of the HIV-1 5'UTR have been obtained by means of a process of in vitro selection wherein the target used was the complete 5'UTR. This approach represents a significant advantage over prior patents and publications as the aptamers obtained in the present invention recognize accessible binding areas in the complete folding of the 5'UTR in one of the two possible conformers, in both, or in the kinetic interface of the balance between them. Thus, the aptamers that have been selected are capable of binding without being affected by steric hindrance caused by adjacent regions and/or other subdomains of said 5'UTR and under the kinetic conditions necessary for this. Another advantage of these aptamers compared to those described by other authors is that, as previously indicated, the combined approach between experimentation and computer simulation (in vitro/in silico approach) has allowed defining the active minimum aptamer without multiplying experimental assays.

BRIEF DESCRIPTION OF THE INVENTION

The present invention is related to the field of aptamers, nucleic acid molecules obtained by in vitro selection or evolution having the ability to specifically bind to a specific molecular target. Specifically, the aptamers to which this invention relates are RNA molecules, DNA molecules or nucleic acid analogues that bind certain genomic regions of human immunodeficiency virus type 1 (HIV-1), more specifically RNA domains present in the 5' untranslated region (5' UTR) of the viral genome, and that had not been described previously as aptamer binding targets. In fact, in the present invention an RNA molecule containing the first 308 nt of the HIV-1 genome was used as target, a remarkably longer fragment than those used hitherto in assays of aptamer selection against HIV-1.

Said target contains the first 308 nt (SEQ ID No: 1) of the total of 336 nt (SEQ ID No: 2) constituting the 5'UTR of the genomic RNA of HIV-1, with the first 290 nt being common (SEQ ID No: 3) to the genomic RNA and the majority of the subgenomic RNAs of the virus (all these numerical data are applied in the case of NL4-3 strain with accession number in GenBank database: AF324493). Although isolated structural elements have been characterized in the 5'UTR (such as TAR, against which the aptamers described in the section on the State of the art have been isolated), as stated the structure of TAR itself and of the other elements is influenced by the presence of the rest of the 5'UTR. Depending on the folding adopted by the 5'UTR (complete, and also in the case of using its first 308 nt) distinct structural domains that perform essential functions for the virus, such as Poly-A or DIS domains, are exposed or not. Depending on the size of the 5'UTR fragment used, the existence of one of the conformers can be favored or not and in any case the stability of one relative to another can be promoted by shifting the balance among both of them towards the more stable structure. In this case, the use of a fragment of 308 nt of HIV-1 5'UTR as a target for selection of aptamers is a closer situation to that in the complete viral genome, so that the system used in the present invention, unlike that used in the previously published cases, allows to identify structural elements on the target molecule that are non-existent when small molecules derived from the 5'UTR are used. Thus, the aptamers obtained experimentally in this invention were found to be specifically targeted to the Poly-A domain, which was found to be the most efficient target within the HIV-1 5'UTR. The frequency with which aptamers that contain a complementary binding sequence to this Poly-A target appear is much higher than that of aptamers with complementary sequence to motifs in TAR (the sequence and structure of which had been described as effective for binding of nucleic acids, both aptamers and antisense RNAs, Kolb et al., 2006) or in DIS (domain selected by nature to perform a function that involves binding to another molecule of viral genomic RNA). Thus, the present invention is based on the experimental demonstration that aptamers can be targeted to a new and unexpected target within the 5'UTR when their length is sufficiently large: the Poly-A site.

The method followed for obtaining these aptamers involves the use of classic strategies of in vitro selection of nucleic acids, in combination with a novel bioinformatic analysis or in silico that allows identifying new molecules capable of binding to the target. The developed aptamers have a sequence common to all of them, the octanucleotide 5'-GGCAAGGA-3' or 5'-GGCAGGGA-3', forming a single-stranded terminal loop closing a double-stranded stem of at least three pairs of nucleotides, in both cases. Aptamers containing these sequences can have flanking regions both at their 5' and 3' end, preferably with lengths comprised between 1 and 75 nucleotides. Said flanking regions may form any structure or provide any additional functionality. In particular, aptamers with a total length of 64 nucleotides have been developed in the present invention, all of which containing the abovementioned octanucleotides in different positions within their sequence. Moreover, thanks to the aforementioned in vitro/in silico combined approach, it has been possible to define a specific RNA molecule of just 16 nucleotides, with the sequence 5'-CCCCG-GCAAGGAGGGG-3' (SEQ ID NO:39), which maintains the stem-loop structure shown and that has demonstrated having a functionality similar to that of 64 nucleotide long aptamers. The ability of these molecules to bind the HIV-1 5'UTR, and preferably the Poly-A domain, through the octanucleotide common to all of them is exploited, both in in vitro assays and in cell culture. The binding of these aptamers to the HIV-1 genome results in the inhibition of virus replication in cell culture as determined by means of specific assays. Interestingly, it should be noted that the binding target of the octanucleotide present in the aptamers to the Poly-A domain is conserved across the entire spectrum of sequences of analyzed viral isolates (FIG. 1). It is therefore expected that the aptamers of the present invention, which specifically bind to the Poly-A domain, will be active against HIV-1 isolates corresponding to the M (and within this its different subtypes and recombinant forms), N, O and P groups.

DESCRIPTION OF THE INVENTION

The present invention is based on the fact that the inventors have identified, thanks to the combination of in vitro nucleic acid selection systems with a novel bioinformatic analysis or in silico, a number of new aptamers containing a minimum common motif and specifically binding to genomic regions of HIV-1, more specifically to RNA domains present in the 5'UTR of the viral genome. Such binding between the aptamer and the HIV-1 genome inhibits viral replication. Therefore, these molecules are useful for the development of new pharmaceutical compositions for the treatment of infections caused by this virus.

A first aspect of the present invention is related to an aptamer, or any of their derivatives and enantiomers, able to specifically bind accessible areas in the complete folding of the 5'-UTR region of the genome of the human immunodeficiency virus HIV type 1 (HIV-1), being useful for example for inhibiting the replication of HIV-1, comprising a structure with the sequence:

$Mon^1-Mon^2-Mon^3-Mon^4-Mon^5-Mon^6-Mon^7-Mon^8$,
wherein Mon1 to $Mon^8$ are monomers of a nucleic acid or of a chemical analogue of nucleic acid.

According to the present invention, the term "nucleic acid monomer" refers to a nucleotide in which its nucleotide base is adenine (A), guanine (G), cytosine (C), thymine (T) or uracil (U). According to the present invention, the term "monomer of a chemical analogue of nucleic acid" refers to the minimum unit which forms a chemical analogue of nucleic acid when polymerizes, each of these minimum units containing a nitrogenous base (A, G, C, T or U) covalently bound to the analogue backbone component of ribose-phosphate or deoxyribose-phosphate typical of nucleic acids. In the present description, the term "chemical analogue of nucleic acid" may also be referred to by synonymous terms such as "nucleic acid analogous molecule", "nucleic acid analogue" or "nucleic acid synthetic analogue."

Thus, in the aptamers of the present invention the nitrogenous base of $Mon^1$ is a G, the nitrogenous base of $Mon^2$ is a G, the nitrogenous base of $Mon^3$ is a C, the nitrogenous base of $Mon^4$ is an A, the nitrogenous base of $Mon^5$ is an A or a G, the nitrogenous base of $Mon^6$ is a G, the nitrogenous base of $Mon^7$ is a G and the nitrogenous base of $Mon^8$ is an A. Thus the sequence of the aptamers of the present invention can also be represented as GGCAAGGA or GGCAGGGA, defined based on the sequence of nitrogenous bases capable of producing the specific binding to the 5'UTR region of the HIV-1 genome.

In the scope of the present invention, HIV-1 refers to a human infectious virus with preferential tropism for cells of the immune system (preferably CD4+ T cells, macrophages and microglia) and with the potential to produce immunodeficiency in individuals infected by it. The productive viral particles thereof must contain two molecules of positive polarity RNA of genome length (approx. 9.7 kb) with a coding region comprised of nine genes, three of them structural (gag, pol and env) and the other six regulatory (tat, rev, nef, vpu, vif, vpr and vpu), flanked by untranslated regions called 5'UTR and 3'UTR according to their position. Structural genes should encode the structural proteins of the virion (capsid and structural proteins present in the lipid envelope) and the enzymes for reverse transcription of the genetic material (reverse transcriptase), the integration into the cell genome of copy DNA (integrase) and the proteolytic maturation of the gene products of the virus expression (protease). The life cycle of the virus should alternate between a virion phase RNA genetic material and an intracellular phase with DNA genetic material.

In the official taxonomy of HIV-1 species, four groups have been defined so far: M (which in turn contains 9 subtypes: A—with subsubtypes A1 and A2—, B, C, D, F—subsubtypes F1 and F2—, G, H, J and K; and at least 49 recombinant forms between different subtypes), N (with 5 subtypes: I, II, III, IV and V), O and P. Within each subtype strains, variants, and isolates are distinguished. The high mutation rate of HIV-1 means that there is considerable variability among the sequences of isolates from patients, even within a single infected individual. In any event, said inter- and intra-isolate variability is grouped within the HIV-1 species, since the viruses that belong to it have their own replicative lineage, occupy a particular ecological niche, and are at lower genetic distance (that is, they have greater sequence similarity) from each other than from isolates belonging to the next closest species (in this case SIV-1, the simian immunodeficiency virus infecting the chimpanzee, and then HIV-2, the second species that infects humans within the genus Lentivirus). Therefore, when the term HIV-1 is used herein, it refers to any virus or virus population the sequence or sequences of which have greater sequence similarity to the total of isolates sequenced to date for HIV-1 than to isolates corresponding to any other species of virus. In the scope of the present invention, and without limitation, examples of HIV-1 are those indicated in FIG. 1 or any other known to the person of average skill in the art such as those disclosed in document "Kuiken C, et al. 2011" included herein by reference.

Generally, HIV-1 presents high sequence conservation in the 5'UTR of its genome (Kuiken C, et al. 2011). In the scope of the present invention, 5'UTR refers to the 5' untranslated region of different viral RNAs, and which generally has a high degree of structure. The 5'UTR region is also known in the state of the art as "5'-leader" region of the HIV-1 messenger RNA. Similarly, the 5'UTR contains a portion of the long terminal repeat sequence or LTR, which is present at both ends of the viral genomic DNA, specifically the R (repeat, see region between positions 1 to 98, both included, in SEQ ID No: 1, SEQ ID No: 2 and SEQ ID No: 3) and U5 regions (single in 5', see region between positions 99 to 180, both included, in SEQ ID No: 1, SEQ ID No: 2 and SEQ ID No: 3). In this regard, it is worth to note that the region R is also found in the 3' end of all viral RNAs, and contains in its sequence the binding area expected for aptamers protected in the present invention (see region between positions 81 and 86, both included, in SEQ ID No: 1, SEQ ID No: 2 and SEQ ID No: 3).

The 5'UTR is different in different families of subgenomic viral RNAs and in unprocessed genomic RNA, with the region comprised by the first 290 nt being common to all of them. In the present invention, 5'UTR refers preferably to the first 308 nt of the unprocessed viral genomic RNA, containing said common region and 18 additional nucleotides, necessary to complete the SL domain (interrupted by splicing in subgenomic RNAs). The 308 nucleotide 5'UTR, referred to herein as $UTR_{308}$ contains the structural domains described above: TAR, Poly-A, PBS, DIS (see, respectively, regions between positions 1 to 58, 59 to 105, 117 to 237 and 244 to 278, including initial and end positions, in SEQ ID No: 1, SEQ ID No: 2 and SEQ ID No: 3) and SL (see region between positions 283 to 301, both included, in SEQ ID No: 1 and SEQ ID No: 2). However, it should be noted that, as mentioned above, these numerical data should be taken as indicative due to the variability among viral isolates. They have been calculated using the sequence of the laboratory strain NL4-3. Without limitation, examples of HIV-1 5'UTR regions according to the invention are the sequences of nucleotides of 5'UTR regions known to the person with average skill in the field such as those that can be found in document "Kuiken C, et al. 2011", included herein by reference.

In the scope of the present invention, the term "aptamer" refers to an RNA molecule, DNA molecule or any chemical analogue of nucleic acid comprising a sequence of a succession of nitrogenous bases, wherein said succession of nitrogenous bases is responsible for their activity independent of the polymeric backbone onto which they are anchored (which will determine whether it is a natural nucleic acid such as DNA or RNA, or a chemical analogue thereof). As indicated above, the principle of action of any of nucleic acid analogue is, in the context of this invention, exactly the same as that of DNA or RNA, and is defined by the sequence of the nitrogenous bases it contains. However, these analogues generally have higher stability than natural nucleic acids. Indeed, in various areas of biotechnology the use of analogue molecules of natural nucleic acids has proved very useful for various diagnostic and therapeutic applications (reviews in: Geyer et al., 2003; Briones and Moreno, 2012). In the current state of the art various types of chemical analogues of nucleic acids are known, such as for example, and without limitation, those defined in the present description.

Within said analogues of nucleic acids, the case of locked nucleic acids (abbreviated as LNA) characterized by being polymers of nucleotides of β-D-ribofuranose modified with a 2'-O, 4'-C methylene connector is particularly interesting. This type of bond restricts or "locks" the ribofuranose in its 3'-endo conformation. LNA forms hybrids with DNA and with RNA that are much more stable than DNA-DNA, DNA-RNA or RNA-RNA dimmers themselves. Another interesting feature of LNAs is that nucleotides with this conformation can bind to DNA or RNA conventional nucleotides to form hybrid molecules in which interaction with another nucleic acid through the places occupied by the LNA monomers is promoted.

Nucleic acid analogues called "peptide nucleic acids" (PNA) are also very useful. The PNA is a polymer with a peptide nature, unlike the backbone of sugars and phosphates typical of natural nucleic acids. The PNA backbone is formed by units of N-(2-aminoethyl) glycine linked by peptide bonds, is achiral, electrically neutral and lacks phosphorus atoms. The purine (A and G) and pyrimidine (C and T) nucleotide bases are attached to the backbone of the PNA by means of methylenecarbonyl connectors in a conformation such as to allow interaction by means of hydrogen bonds with the nucleotide bases of natural nucleic acids, just as it occurs naturally among them in DNA and RNA. PNA forms extremely stable dimers both with DNA and RNA. Related to the PNA, a new analogue of nucleic acids has recently been synthesized called "thioester peptide nucleic acid" or thioester PNA (tPNA).

Other analogues of nucleic acids are as follows: i) "glycerol-derived nucleic acids" (GNA), the backbone of which consists of glycerol acyclic units linked by phosphodiester bonds; ii) pyranosyl-RNA (p-RNA), containing rings of six atoms of β-D-ribopyranoside type instead of ribofuranosyl like RNA, linked by 4'→2' phosphodiester bonds; iii) "threose nucleic acids" (TNA), based on α-L-threofuranosyl units linked by 3'→2' phosphodiester bonds; iv) "phosphoroamidate morpholino oligomers" (PMO), the monomers of which are composed of morpholino rings linked together by phosphorodiamidate bonds.

Therefore, in chemical analogues of nucleic acids, each of the monomeric units comprising them is one selected from the following group:

- β-D-ribofuranoside modified with a 2'-O, 4'-C methylene connector, with a nitrogenous base bound by means of N-glycosidic bond between nitrogen 9 of purines or 1 of pyrimidines and carbon 1', in the case of LNA analogues; said monomer is capable of being polymerized by means of 5'→3' phosphodiester bond;
- N-(2-aminoethyl) glycine, with a nitrogenous base bound by means of a methylenecarbonyl connector between nitrogen 9 of purines or 1 of pyrimidines and the amino group of glycine backbone, in the case of PNA analogues; said monomer is capable of being polymerized by means of peptide bond between the carbon of the carboxyl group of the glycine backbone and the terminal nitrogen of the aminoethylene group;
- Amino acid cysteine, with a nitrogenous base bound by means of a methylenecarbonyl connector between nitrogen 9 of purines or 1 of pyrimidines and the sulfur in the cysteine skeleton, in the case of tPNA analogues; said monomer is capable of being polymerized by means of conventional peptide bond;
- 1,2,3-propanetriol (also called glycerol), with a nitrogenous base bound by means of N-glycosidic bond between nitrogen 9 of purines or 1 of pyrimidines and the carbon 1', in the case of GNA analogues; said monomer is capable of being polymerized by means of 3'→2' phosphodiester bond;
- δ-D-ribopyranoside, with a nitrogenous base bound by means of N-glycosidic bond between nitrogen 9 of purines or 1 of pyrimidines and the carbon 1', in the case of p-RNA analogues; said monomer is capable of being polymerized by means of 4'→2' phosphodiester bond;
- α-L-threofuranoside, with a nitrogenous base bound by means of N-glycosidic bond between nitrogen 9 of purines or 1 of pyrimidines and the carbon 1', in the case of TNA analogues; said monomer is capable of being polymerized by means of 3'→2' phosphodiester bond;
- Tetrahydro-1,4-oxazine (also called morpholino), with the nitrogenous base bound by means of an N-glycosidic bond between nitrogen 9 of purines or 1 of pyrimidines and the carbon 1' of the morpholino ring, in the case of PMO analogues; said monomer is capable of being polymerized by means of phosphoroamidate connectors linked by amide bonds with nitrogen 4' and ester with oxygen 1'.

So far, the synthesis of many of the chemical analogues of nucleic acids is carried out by chemical synthesis procedures similar to those used for the chemical synthesis of conventional nucleic acids such as, for example and without limitation, the solid phase synthesis using, as monomers for polymerization, phosphoramidite protected derivatives (Horvath et al., 1987). Additionally, the possibility of polymerizing certain nucleic acid analogues by means of enzyme systems using genetically modified variants of the natural polymerases has been described (Pinheiro et al., 2012).

In the scope of the present invention, aptamer derivatives refer to RNA or DNA aptamers, wherein at least one of the nucleic acid monomers of said aptamer has a chemical modification. The person with average skill in the field may find that the introduction of chemical modifications which do not alter the nucleotide sequence and the spatial arrangement of the nitrogenous bases does not change the functionality of the molecule of the aptamers described in the present invention, which mainly depends on the sequence complementarity principle between the aptamer and its target molecule. However, such modifications have a positive effect because they increase the stability and the half-life of the aptamer. The increase in stability results in an increase in the overall efficiency of the aptamer as its increased resistance to degradation involves an increase in the intracellular availability of the inhibitor. By way of example and without limitation, this modification may be useful to increase resistance to degradation by nucleases enzymes (DNases or RNases) in biological media. The modifications in nucleotides that produce such increase in resistance to enzymatic degradation comprise a substituent selected, without limitation, from the following list: a fluorine atom, an amino group, a methyl group, a methoxy group and any combination thereof. An increase in resistance of aptamers to degradation by exonucleases is also achieved by blocking their 5' or 3' ends using different types of molecules or substituents, such as for example introducing as a substituent a molecule blocking the phosphate group of the 5' end of the nucleic acid, or the hydroxyl group of its 3' end.

As understood in the invention, the modifications in the nucleotides to produce resistance to enzymatic degradation of the aptamer comprising fluorine atoms refer to the substitution of at least one of the chemical groups of the nucleotide molecule by a chemical group containing at least one fluorine atom, as it occurs and without limitation in the (2'-deoxy-2'-fluoro)-nucleotides.

As understood in the invention, the modifications in the nucleotides to produce resistance to enzymatic degradation of the aptamer comprising an amino group refer to the substitution of at least one of the chemical groups of the nucleotide molecule by a chemical group containing at least one amino group, as it occurs and without limitation in the 2'-O-(3-aminopropyl)-nucleotides.

As understood in the invention, the modifications in the nucleotides to produce resistance to enzymatic degradation of the aptamer comprising a methyl group refer to the substitution of at least one of the chemical groups of the nucleotide molecule by a chemical group containing at least one methyl group, as it occurs and without limitation in the 2'-O-methyl-nucleotides.

As understood in the invention, the modifications in the nucleotides to produce resistance to enzymatic degradation of the aptamer comprising a methoxy group refer to the substitution of at least one of the chemical groups of the nucleotide molecule by a chemical group containing at least one methoxyethyl group, as it occurs and without limitation in the 2'-O-methoxyethyl-nucleotides.

As understood in the invention, the modifications in the nucleotides to increase resistance of the aptamer to degradation by exonucleases by blocking the phosphate group of the 5' end refer to the covalent bonding of an atom or an organic or inorganic molecule to said phosphate group, as it can be and without limitation the bonding by means of an ester bond in a molecule of α-α'-[4,12-dioxo-6-[[[5-(fosfonooxy) pentyl]amine]carbonyl]-3,13-dioxa-5,11-diaza-1,15-pentadecanediyl]bis[ω-methoxypoly(oxy-1,2-ethanediyl)].

As understood in the invention, the modifications in the nucleotides to increase resistance of the aptamer to degradation by exonucleases by blocking the hydroxyl group of the 3' end refer to the covalent bonding of an atom or an organic or inorganic molecule to said 3'-hydroxyl group, as it can be and without limitation the bonding by means of a phosphodiester connector 3'→3 of a thymine deoxyribonucleoside.

Likewise, other modifications of aptamers covered by the present invention are those in which at least one of the nucleic acid monomers in RNA aptamers is replaced by an LNA monomer (described above), resulting in a molecule analogue to said RNA, that may optionally be also modified, as explained above, with fluorine atoms or amino, methoxy or methyl groups. On the other hand, in order to increase the resistance of aptamers to nuclease degradation, enantiomeric forms of DNA or RNA aptamers, which may optionally have any of the modifications described herein, are also useful. Thus, the present invention also contemplates the protection of enantiomers of any of the RNA or DNA aptamers described in the present invention. So far, the synthesis of these modified nucleic acids is carried out by means of the inclusion of the modified monomeric precursor at an appropriate stage of the chemical synthesis, or by means of direct incorporation of the modified precursor nucleotide during an enzymatic synthesis reaction either by the tolerance of the polymerase enzyme to the incorporation of modified nucleotides or by means of the use of enzymes artificially modified for this purpose (reviews in Klussmann, 2006; Lauridsen et al. 2012).

In a preferred embodiment, the aptamer or any derivatives and enantiomers thereof defined above in this aspect of the invention, in addition to the structure with sequence $Mon^1$-$Mon^2$-$Mon^3$-$Mon^4$-$Mon^5$-$Mon^6$-$Mon^7$-$Mon^8$, also comprises an anterior flanking region bound to the monomer $Mon^1$ and a posterior flanking region bound to the monomer $Mon^8$ of said structure. According to the invention, each flanking region comprises a sequence the length of which is of at least 4 nucleic acid monomers and/or chemical analogue of nucleic acid, preferably of between 4 and 75 monomers, wherein the nitrogenous bases of at least 3 of the 4 monomers (preferably all 4 monomers) of the anterior flanking region closest to $Mon^1$, contiguous or not, are paired with the nitrogenous bases of at least 3 of the 4 first monomers (preferably all 4 monomers) of the posterior flanking region closest to $Mon^8$, such that the sequence structure $Mon^1$-$Mon^2$-$Mon^3$-$Mon^4$-$Mon^5$-$Mon^6$-$Mon^7$-$Mon^8$ forms a single-stranded terminal loop closing a double-stranded stem formed by the flanking regions with said paired nucleotides. This means that when the aptamer comprises both flanking regions with four monomers, the structure of the aptamer comprises a structure with the sequence $Mon^{a4}$-$Mon^{a3}$-$Mon^{a2}$-$Mon^{a1}$-$Mon^1$-$Mon^2$-$Mon^3$-$Mon^4$-$Mon^5$-$Mon^6$-$Mon^7$-$Mon^8$-$Mon^{b1}$-$Mon^{b2}$-$Mon^{b3}$-$Mon^{b4}$, wherein $Mon^{a1}$ to $Mon^{a4}$ are the monomers of the anterior region bound to $Mon^1$, and $Mon^{b1}$ to $Mon^{b4}$ are the monomers of the posterior region bound to $Mon^8$. Similarly, in the case where the aptamer has flanking sequences of between 4 and 75 monomers, said aptamer comprises a structure with the sequence $Mon^{a\ (i+4)}$-$(Mon^{ax})$-$Mon^{a3}$-$Mon^{a2}$-$Mon^{a1}$-$Mon^1$-$Mon^2$-$Mon^3$-$Mon^4$-$Mon^5$-$Mon^8$-$Mon^7$-$Mon^8$-$Mon^{b1}$-$Mon^{b2}$-$Mon^{b3}$-$(Mon^{bx})$-$Mon^{b(j+4)}$, wherein i and j are independently selected from a value comprised between 0 and 71, wherein $Mon^{a1}$, $Mon^{a2}$, $Mon^{a3}$, $Mon^{ax}$ and $Mon^{a\ (i+4)}$ are the nucleic acid or chemical analogue of nucleic acid monomers of the anterior flanking region and $Mon^{b1}$, $Mon^{b2}$, $Mon^{b3}$, $Mon^{bx}$ and $Mon^{b(j+4)}$ are the nucleic acid or chemical analogue of nucleic acid monomers of the posterior flanking region. And in addition, the fragment $Mon^{a\ (i+4)}$-$(Mon^{ax})$-$Mon^{a3}$-$Mon^{a2}$-$Mon^{a1}$ with the fragment $Mon^{b1}$-$Mon^{b2}$-$Mon^{b3}$-$(Mon^{bx})$-$Mon^{b\ (j+4)}$ form a double-stranded stem by pairing of at least 3 of the monomers of the group consisting of: $Mon^{a1}$, $Mon^{a2}$, $Mon^{a3}$, $Mon^{ax}$ and $Mon^{a(i+4)}$; with at least 3 of the monomers of the group consisting of: $Mon^{b1}$, $Mon^{b2}$, $Mon^{b3}$, $Mon^{bx}$ and $Mon^{b(j+4)}$.

According to the present invention, the complementarity rules to which these respective pairings of $Mon^{a1}$ to $Mon^{a4}$ with $Mon^{b1}$ to $Mon^{b4}$ are subjected are: A with T or U; C with G; G with C or U; T with A; U with A or G.

The flanking regions in addition to serving to form the structure anterior to the loop closing the double-stranded stem, may be defined by sequences that serve to stabilize and direct the aptamer to a subcellular compartment such as e.g., and without limitation, by means of the use of snRNA U6 hairpins such as SEQ ID No: 4 and/or SEQ ID No: 5, such that the aptamer may be located in the cell nucleus. In that sense, such hairpins are but an example of the "flanking regions" described above, whatever structure they may form and additional functionality they may provide. Another possible example would be the one described for the nucleolar localization of an aptamer directed against TAR by means of the incorporation of the respective terminal regions of snRNA U16 (as described in Kolb et al., 2006).

According to the invention, the length of the flanking region may vary depending on the size of the regions (be they functional or not, and naturally occurring or artificial) to be added to the aptamer to confer any additional property. By way of example and without limitation, in order to achieve nuclear localization of the aptamers while its resistance to degradation by exonucleases is increased in the present invention, the flanking hairpins of the snRNA U6 were added, since it is known that they confer said properties. Specifically these hairpins, at 5' and 3' of the aptamer have lengths of 25 and 24 nucleotides respectively.

In another preferred embodiment, the aptamer, or any of its derivatives and enantiomers, comprises a structure with the sequence $Mon^{a4}$-$Mon^{a3}$-$Mon^{a2}$-$Mon^{a1}$-$Mon^1$-$Mon^2$-$Mon^3$-$Mon^4$-$Mon^5$-$Mon^6$-$Mon^7$-$Mon^8$-$Mon^{b1}$-$Mon^{b2}$-$Mon^{b3}$-$Mon^{b4}$, on wherein $Mon^{a1}$ to $Mon^{a4}$ and $Mon^{b1}$ to $Mon^{b4}$ are monomers of a nucleic acid or of a chemical analogue of nucleic acid such that:

i. the nitrogenous bases from $Mon^{a1}$ to $Mon^{a4}$ are independently selected from the following group: an A, a C, a G, a T and a U (wherein $Mon^{a3}$ is preferably A, G, T or U, and/or wherein $Mon^{a4}$ is preferably C, T or U.);
ii. the nitrogenous base of $Mon^{b1}$ is complementary to the nitrogenous base of $Mon^{a1}$;
iii. the nitrogenous base of $Mon^{b2}$ is complementary to the nitrogenous base of $Mon^{a2}$;
iv. the nitrogenous base of $Mon^{b3}$ is complementary to the nitrogenous base of $Mon^{a3}$;
v. the nitrogenous base of $Mon^{b4}$ is complementary to the nitrogenous base of $Mon^{a4}$;

and wherein $Mon^1$ to $Mon^8$ are the monomers as previously defined. In this embodiment, the anterior flanking region comprises the sequence of monomers $Mon^{a4}$-$Mon^{a3}$-$Mon^{a2}$-$Mon^{a1}$ and the posterior flanking region comprises the sequence of monomers $Mon^{b1}$-$Mon^{b2}$-$Mon^{b3}$-$Mon^{b4}$. Moreover, the monomer $Mon^{a1}$ is paired or hybridized with Mon$^{b1}$, the monomer Mon$^{a2}$ is paired with Mon$^{b2}$, the monomer Mon$^{a3}$ is paired with Mon$^{b3}$ and the monomer Mon$^{a4}$ is paired with Mon$^{b4}$.

In a preferred embodiment of the aptamer, or of any derivatives and enantiomers thereof, the monomers forming it are nucleotides, and they can be ribonucleotides (RNA aptamer) or deoxyribonucleotides (DNA aptamer). In a more preferred embodiment of the above, the aptamer is an RNA molecule.

In another preferred embodiment of the aptamer, or of any derivatives and enantiomers thereof, when the structure Mon$^1$-Mon$^2$-Mon$^3$-Mon$^4$-Mon$^5$-Mon$^6$-Mon$^7$-Mon$^8$ consists of nucleic acid monomers, said structure consists of an octanucleotide with the sequence 5'-GGCARGGA-3', wherein R represents a nucleotide selected from an A nucleotide or a G nucleotide.

In another preferred embodiment of the aptamer, or of any derivatives and enantiomers thereof, when the structure Mon$^1$-Mon$^2$-Mon$^3$-Mon$^4$-Mon$^5$-Mon$^6$-Mon$^7$-Mon$^8$ consists of nucleic acid monomers, the structure Mon$^{a4}$-Mon$^{a3}$-Mon$^{a2}$-Mon$^{a1}$-Mon$^1$-Mon$^2$-Mon$^3$-Mon$^4$-Mon$^5$-Mon$^6$-Mon$^7$-Mon$^8$-Mon$^{b1}$-Mon$^{b2}$-Mon$^{b3}$-Mon$^{b4}$ consists of a polynucleotide with sequence selected from SEQ ID No: 6 and SEQ ID No: 7. SEQ ID No: 6 and SEQ ID No: 7 correspond to nucleic acids with the same sequence of nitrogenous bases, SEQ ID No: 6 being a DNA molecule and SEQ ID No: 7 an RNA molecule. the sequence of SEQ ID No: 6 is 5'-N$^1$N$^2$N$^3$N$^4$GGCARGGAN$^5$N$^6$N$^7$N$^8$-3', wherein N$^1$, N$^2$, N$^3$ and N$^4$ are independently selected from A, C, G or T (and preferably N$^3$ is A, G or T, and/or N$^4$ is T or C, SEQ ID No: 8); R is independently selected from A and G; N$^5$ is the nucleotide complementary to N$^4$; N$^6$ is the nucleotide complementary to N$^3$; N$^7$ is the nucleotide complementary to N$^2$; and N$^8$ is the nucleotide complementary to N$^1$. the sequence of SEQ ID No: 7 is 5'-N$^1$N$^2$N$^3$N$^4$GGCARGGAN$^5$N$^6$N$^7$N$^8$-3', wherein N$^1$, N$^2$, N$^3$ and N$^4$ are independently selected from A, C, G or U (and preferably N$^3$ is A, G or U, and/or N$^4$ is U or C, SEQ ID No: 9); R is selected from A and G; N$^5$ is the nucleotide complementary to N$^4$; N$^6$ is the nucleotide complementary to N$^3$; N$^7$ is the nucleotide complementary to N$^2$; N$^8$ is the nucleotide complementary to N$^1$. The complementarity rules to which these pairings are subject are: A with T or with U, C with G, G with C or with U, T with A, U with A or with G.

In another preferred embodiment of the aptamer, or of any derivatives and enantiomers thereof, when the structure Mon$^1$-Mon$^2$-Mon$^3$-Mon$^4$-Mon$^5$-Mon$^6$-Mon$^7$-Mon$^8$ or the structure Mon$^{a4}$-Mon$^{a3}$-Mon$^{a2}$-Mon$^{a1}$-Mon$^1$-Mon$^2$-Mon$^3$-Mon$^4$-Mon$^5$-Mon$^6$-Mon$^7$-Mon$^8$-Mon$^{b1}$-Mon$^{b2}$-Mon$^{b3}$-Mon$^{b4}$ consists of nucleic acid monomers, the aptamer or its derivative comprises a nucleotide sequence selected from the group consisting of: SEQ ID No: 10 (IX03-1), SEQ ID No: 11 (IX24-1), SEQ ID No: 12 (IX36-1), SEQ ID No: 13 (X02-1), SEQ ID No: 14 (X04-2), SEQ ID No: 15 (X09-1), SEQ ID No: 16 (X10-7), SEQ ID No: 17 (X13-1), SEQ ID No: 18 (X36-1), SEQ ID No: 19 (X41-2), SEQ ID No: 20 (XI1-17), SEQ ID No: 21 (XI21-7), SEQ ID No: 22 (XI23-3), SEQ ID No: 23 (XI141-2), SEQ ID No: 24 (XI13-1), SEQ ID No: 25 (XI101-1), SEQ ID No: 26 (XI149-1), SEQ ID No: 27 (XI107-1), SEQ ID No: 28 (XI129-1), SEQ ID No: 29 (XIV22-23), SEQ ID No: 30 (XIV26-6), SEQ ID No: 31 (XIV1-2), SEQ ID No: 32 (XIV32-1), SEQ ID No: 33 (XIV5-1), SEQ ID No: 34 (XIV12-1), SEQ ID No: 35 [RNA16(+)], SEQ ID No: 36 [RNA16(+)var-G], SEQ ID No: 37 (L-XIV22-23) and SEQ ID No: 38 (L-XIV26-6). In another preferred embodiment such as the previous one, the nucleotide sequence of the aptamer or its derivative is selected from the consensus SEQ ID No: 39 [generic RNA16(+)], this is SEQ ID No: 35 [RNA16(+)] or SEQ ID No: 36 [RNA16(+) var-G], and more preferably is SEQ ID No: 35 [RNA16(+)].

Throughout the present disclosure, the aptamers defined in this aspect of the invention, or any of its derivatives and enantiomers, can appear also referred to as "aptamers of the invention".

A second aspect of the invention is related to a DNA genetic construct useful for the synthesis by transcription, in vitro (IVT) or intracellular, of an RNA aptamer of the invention, characterized in that it comprises a DNA nucleotide sequence encoding the nucleotide sequence of the RNA aptamer.

A third aspect of the invention is related to a method for the production of an aptamer of the invention, comprising combining experimental techniques of in vitro selection of nucleic acids with computational optimization that allow analyzing both the sequences generated by in vitro selection and their corresponding secondary structures. Without limitation, an example of the method used is detailed below in Examples 1 and 2. In these cases, the experimental techniques involve:

i. Generating a DNA template for obtaining a population of RNA molecules by in vitro transcription. This double-stranded DNA template was obtained by hybridization and enzymatic extension of two partially complementary DNA oligonucleotides designed for that purpose. These oligonucleotides were obtained commercially and were generated by chemical synthesis of DNA. One of said oligonucleotides contains the promoter sequence of the T7 phage RNA polymerase at its 5' end, followed by a 25 nt region with random sequence. An example of suitable oligonucleotides is the pair 5'EcoRIK (SEQ ID No. 40) and 3'RANDOMK (SEQ ID No. 41).

ii. Obtaining a population of RNA molecules consisting of a random sequence region with 25 nt in length and flanked by anterior and posterior regions of constant and known sequence of 10 and 29 nt in length respectively. This population was generated by IVT using as a template the one obtained in step "i";

iii. Selecting aptamers against the RNA target molecule containing the first 308 nt of the HIV-1 5'UTR (SEQ ID No: 1) immobilized on a streptavidin-sepharose solid support, controlling variables such as binding temperature, binding time and aptamer: target molecular ratio;

iv. Recovering the aptamers bound to the target molecule;

v. Reverse transcription of the RNA molecules corresponding to the selected aptamers by means of enzymatic reaction using the reverse transcriptase activity of the Tth enzyme from *Thermus thermophilus*. In this manner, a population of single-stranded copy DNA molecules (cDNA) complementary to the sequence of the starting RNA molecules is obtained;

vi. Amplifying the cDNA obtained in step "v" by means of PCR, using as DNA synthetic oligonucleotide primers and the DNA-dependent DNA polymerase activity also present in the Tth enzyme. One of these should contain the sequence of the promoter of the phage T7 RNA polymerase so that it is included within the amplified product at an position equivalent to the one it has in the DNA template generated in step "i";

vii. Cloning the PCR product from step "vi" in a commercial plasmid vector, using competent bacteria from *Escherichia coli* strains;

viii. Repeating successive experimental rounds or cycles defined by steps "ii" to "vi", preferring 14 repeated rounds such as described, for example, in the case of the present invention;

viii. Sequencing a minimum of 30 molecular clones, product of step "vii" of each round of selection.

The computational techniques used after the experimental techniques consist of:

ix. Aligning the sequences corresponding to all aptamers obtained in the selection process, determining their lengths and the sequence repeats produced at each round, or between different rounds;

x. Quantifying the difference or "distance" existing between the sequence of all molecules measured as the number of mutations among them (Hamming distance);

xi. Analysing the sequences by means of multiple alignment and clustering programs based on nucleotide distances, and characterization of groups and subgroups of sequences having greater sequence similarity;

xii. In silico folding of all the RNA molecules generated during the selection process in their minimum energy structure or "MFE structure" using for this the RNAfold program of the "Vienna RNA package";

xiii. Representing the structures in dot-bracket notation (wherein the unpaired nucleotides are indicated by dots, and the ones that form part of base pairs by brackets) and aligning said structures represented in such notation;

xiv. Quantifying the distance between the structures in the dot-bracket notation, using for this three complementary approaches called "Hamming", "Base pair" and "Tree edit", as described in detail in Example 2 of the present invention;

xv. Analysing the structures aligned by means of multiple alignment and grouping or clustering programs based on the distances obtained, and characterizing groups and subgroups of sequences having greater structural similarity;

xvi. Analysing all structures and in particular those that are part of the groups identified in item xv, searching for common structural motifs;

xvii. Analysing the sequences present in the molecules that share said common structural motifs;

xviii. Characterizing the minimum structural motif (or "minimal aptamer") shared by the aptamers identified in item xvii, and analysing the possibility of designing synthetic RNA molecules to ensure the presence of the sequences detected in the unpaired regions of said domains, making the regions that form their double stranded stems more stable;

xix. Analysing possible interactions between the selected aptamers and the RNA target used during the selection process, and also the interaction between the "minimum aptamer" and the target, considering both the position of the target in which said interaction occurs and the thermodynamic stability of each aptamer-target pairing;

xx. Designing a molecule useful as interaction "negative control", the structure of which is the same as that in the "minimal aptamer", but the sequence of which has the lowest probability of interaction with the target RNA in its unpaired region.

In essence, and in general, the experimental techniques of in vitro selection of nucleic acids for the production of the aptamers of the invention include:

a. Obtaining by in vitro transcription RNA molecules with random sequence, of at least 25 nucleotides in length, flanked by anterior and posterior regions of constant and known sequence preferably by transcription of a double stranded DNA template previously obtained by hybridization and extension of the two oligonucleotides 5'EcoRIK (SEQ ID No. 40) and 3'RANDOMK (SEQ ID No. 41);

b. Selecting and isolating the RNA molecules obtained in the above step with higher affinity for the target molecule that corresponds to the 5'UTR region of HIV-1 (SEQ ID No 1). Preferably this process is achieved by affinity column purification with said molecule immobilized on a sepharose-streptavidin solid support;

c. Obtaining and amplifying a cDNA obtained from the RNA molecules isolated in the preceding step, preferably with the two oligonucleotides 5'EcoRIK (SEQ ID No: 40) and 3'XhoIK (SEQ ID No: 42).

d. Sequencing the amplified cDNA, preferably by cloning and sequencing of clones;

e. Repeating successive cycles defined by the steps "a-d", using as a transcription template of step "a" the product amplified in step "c", to obtain a progressive enrichment of molecules with higher binding capacity to the target in the resulting population.

As for the optimization computational techniques of the aptamers sequences generated by the above in vitro selection techniques, they basically comprise:

f. Classifying the cDNA sequences sequenced in the different "a-d" repeated cycles, comprising quantifying the nucleotide difference existing between said sequences, multiple aligning and sequence grouping or clustering of said cDNA, folding of the RNA sequence derived from the cDNA to the minimum energy structure, characterizing the minimum structural motif between sequences and analysing interactions between DNA sequences and the RNA 5'UTR target of HIV-1 (SEQ ID No: 1). In preferred embodiments, this sequence classification comprises the steps ix to xx defined above.

A fourth aspect of the invention refers to the use of an aptamer of the invention as molecule with the ability to specifically bind to the 5'UTR region of the genome of HIV-1. The aptamers of the invention are therefore useful as interference agent of a function and/or activity of the 5'UTR region of the genome of HIV-1.

Within the scope of the present invention, the term "function and/or activity of the 5'UTR region" refers to the set of physiological processes in which the complete 5'UTR region, any of its subregions (R or U5) or any of its functional elements (TAR, Poly-A, PBS, DIS, SD and Psi) are implicated. These functions include the activation of the transcription, the polyadenylation of the genomic and subgenomic viral RNAs, the recruitment of the primer for reverse transcription, the change of template strand during reverse transcription, the dimerization of genomic RNAs and their packaging in viral particles, the splicing or differential processing of different populations of genomic RNA and the translation of viral RNAs.

A fifth aspect of the invention refers to the use of an aptamer of the invention as an inhibitor of the replication of HIV-1 in a cell culture.

A sixth aspect of the invention refers to the use of an aptamer of the invention for detecting, characterizing and/or quantifying HIV-1 in vitro. In this case, the binding of the aptamer to its target would indicate the presence of HIV-1, preferably from isolates with the binding target of the aptamer conserved, so that the amount of aptamer bound can be directly relatable with the number of units of the HIV-1 genome. Similarly, in another related application the location of the aptamer once internalized into a cell susceptible to be infected may indicate the location of the HIV-1 genome (or of subgenomic fragments thereof which retain their 5'UTR) by means of the use of fluorescent in situ hybridization techniques (FISH), immunofluorescence, immunohistochemistry or the like. In these cases, the unmodified aptamer may be detectable and quantifiable by means of techniques of reverse transcription and quantitative PCR. The aptamer may also be modified in order to provide it with a directly or indirectly detectable property, also allowing determining its location in a biological sample. Thus, the aptamer can be detected, quantified and located directly if it has been synthesized using radioisotopes incorporated into the structural components of the nucleic acid or nucleic acid analogue. The detection and quantification may be carried out by means of direct (for example, Geiger Müller) or indirect (for example, scintillation counter) measuring instruments and the location by means of radiography or phosphorescence storage systems. Additionally, the aptamer can be indirectly detected, quantified and localized by means of the detection, quantification and localization of a component covalently bonded to the aptamer for this purpose, which could consist, without this list limiting the possibilities, of: a fluorophore detectable by its fluorescence radiation emission in a wave length range determined after specific excitation by means of radiation in a different wave length range; avidin or biotin, molecules capable of binding the protein streptavidin conveniently labeled; an inorganic or organic compound capable of being detected by specific antibodies and detectable by techniques such as immunofluorescence or immunohistochemistry; a molecule with detectable enzymatic capacity because it specifically catalyzes a colorimetric or luminescent reaction. Finally, the aptamer could be indirectly detected by means of the detection, by the techniques mentioned above, of another nucleic acid with ability to specifically hybridize with it.

A seventh aspect of the invention refers to the use of an aptamer of the invention as biosensor molecule for the detection and/or quantification of HIV-1 in a biological sample such as, for example and without limitation, plasma, blood, semen, saliva, tissue, histological preparations, cell extracts or others. In these cases, the aptamer could be detected, quantified and located similarly to as described in the above aspect of the invention.

An eighth aspect of the invention refers to the use of an aptamer of the invention for the manufacture of a pharmaceutical composition.

In a ninth aspect, the invention relates to said pharmaceutical composition. The pharmaceutical composition according to the present invention comprises at least one aptamer, or any of its derivatives and enantiomers. Said composition may be also referred to in the present description as "pharmaceutical composition of the invention" or "composition of the invention", and can simultaneously comprise more than one aptamer of any of those defined in the first aspect of this invention. Additionally, it may comprise other enhancer or therapeutic molecules together with, optionally, one or more pharmaceutically acceptable adjuvants and/or vehicles.

In accordance with the present invention, the pharmaceutical compositions of the invention can be administered to humans or may be used in veterinary medicine, particularly with other mammals. The administration is carried out with a "therapeutically effective dose", being sufficient to demonstrate a benefit for the patient, usually associated with the decrease in the replicative capacity of the virus in the infected organism. Such benefit may involve the improvement of at least one symptom associated with the HIV-1 infection. The prescription of treatment, that is, the decisions on the dose, frequency, duration, etc., shall fall under the responsibility of the general practitioner or the specialist who treats the infected patient.

In the scope of the present invention, the term "therapeutically effective dose" refers to an amount (or amount per mass unit of the individual to whom it is administered) of a drug or compound that causes a detectable therapeutic effect on an individual or a group of individuals to whom it is administered, causing minimal side or toxic effects. The term "therapeutically effective dose-50" or "therapeutically effective dose-95" includes a statistical value in which the therapeutic effect should be detectable in 50% or 95% of the individuals to whom it is administered. With regard to the toxic effects of the drug or compound, it is preferable for the effective therapeutic dose to not cause any. However, although sometimes there can be toxic effects, a compromise can be reached in which it is considered that they are preferable to the normal development of the disease, infection or condition without the administration of the drug or compound, and these can in turn be treated by means of additional therapies. Such is the case of current drugs in the treatment of HIV.

Pharmaceutical compositions, in accordance with the present invention, may comprise, in addition to the active ingredient, one or more pharmaceutically acceptable adjuvants and/or vehicles and known to those skilled in the field. Such materials should be non-toxic and they should not interfere with the effectiveness of the active ingredient (the aptamer, in the case of the present invention). The precise nature of the carrier or coadjuvant material will depend on the route of administration, which may be, for example and without setting a criterion for exclusion, oral, by inhalation, by dermal or mucosa absorption, or by injection, for example cutaneous, subcutaneous or intravenous. The pharmaceutical compositions in which the active molecule is in a usual form to make it available within a cell (in this case, a cell infected with HIV-1) are especially preferred, such as for example inside a vesicle consisting of fatty acids, a liposome consisting of lipids, a nanostructure formed by proteins or other molecular components known for such purposes by those skilled in the field. Dosage forms for oral administration may be in the form of tablets, capsules, powder or liquid solution. A tablet may include a solid carrier such as gelatin or an adjuvant. Generally the liquid pharmaceutical compositions comprise a liquid carrier such as water, animal, vegetable or synthetic oils. Physiological saline solutions may contain dextrose or other saccharide or glycol solution such as ethylene glycol, propylene glycol or polyethylene glycol. For intravenous, cutaneous or subcutaneous injection or injection in the place of the affliction, the active ingredient will be in the form of a parenterally acceptable aqueous solution which is pyrogen-free and have a suitable pH, tonicity and stability. Those skilled in the art will be able to prepare suitable solutions using, for example, isotonic vehicles such as saline injection, Ringer's injection solution and Ringer's injection solution with lactate. When required, preservatives, stabilizers, buffering systems, antioxidants and/or other additives may be included.

Another aspect of the invention refers to the use in medicine of the aptamers of the invention, and therefore also to the use of at least one aptamer of the invention for the manufacture of a pharmaceutical composition for the treatment and/or prevention of a disease (preferably a disease caused by HIV, such as an HIV-1 infection or AIDS) or for inhibiting the replication of HIV in a patient infected with the same. It should be understood that this aspect of the invention also protects a method of treatment and/or prevention of a disease caused by HIV (preferably HIV-1) in a subject, comprising administering a therapeutically effective amount of an aptamer of the invention.

DESCRIPTION OF THE FIGURES

FIG. 1.—Alignment of sequences corresponding to the Poly-A domain present in the 5'UTR of different viral isolates of HIV-1 and chimpanzee SIV. The figure shows an adaptation of a sequence compendium alignment published in Kuiken C, et al. (2011) comprising the sequence of the Poly-A domain. The upper part shows a sequence consensus of the reference isolate B.FR.83.HXB2 (positions 59-105 of SEQ ID NOs. 1 2 or 3) and below the sequences of the different HIV-1 isolates (corresponding to groups M—with different subtypes and recombinant forms—, N, O and P of the virus) of which there is a register of the sequence of the Poly-A domain, as well as, by way of comparison, different isolates of the simian immunodeficiency virus (SIV) affecting chimpanzee are aligned. The dots (.) mean that there is no record of that position in the sequenced fragment of the isolate; the dashes (-) mean that the position sequenced in the isolate has the same nucleotide base as in the sequence of the reference isolate; any modification of the sequence of an isolate with respect to the sequence of the reference isolate is indicated with the letter (A, C, G or T) representing the corresponding nucleotide. The binding sequence of the octanucleotide 5'-GGCARGGA-3' present in the aptamers described in this invention is framed in the box (more details in the text, and in FIG. 8).

FIG. 2.—Analysis of sequence variability, by means of clustering and phylogenetic programs based on distances. Sequence groups 1 to 3 are marked with rectangles. The sequences that have the conserved motif are marked with black circles.

FIG. 3.—Progression of distance between sequences (Hamming) and structures (base pair) within each round throughout the in vitro selection process. The overall trend of the average values is decreasing in both cases with the exception of an increase in intra-round distances between structures when passing from round III to V, and from VIII to IX. This increase may be due to the simultaneous selection of two or more groups the mutual differences in sequence and/or structure of which are greater than the ones that would be obtained in average in comparison with random sequences.

FIG. 4.—Classification of structures from their base pair distances using the same programs as in the classification of sequences of FIG. 2. Sequence groups 1 to 3 are marked with rectangles, as in FIG. 2. The sequences that have the conserved motif are marked with black circles. The MFE structures characteristic of the groups 1, 2a and 2b are shown.

FIG. 5.—MFE Structures corresponding to the aptamers of round XIV; the loop 5'-GGCAAGGA-3' (5'-GGCA-GGGA-3' on XIV32) forming part of the conserved motif with structure in dot-bracket notation is marked with a rectangle ((((........))). The number of repetitions N of each sequence is shown as a suffix "_N". The upper left box shows the structures corresponding to the sequences of group 2, the upper right box structures correspond to those of group 1, and the lower box represents the structures for the other three sequences of round XIV that are not part of these groups. In FIG. 5, XIV22_23 corresponds to SEQ ID NO:29, XIV1_2 corresponds to SEQ ID NO:31, XIV32_1 corresponds to SEQ ID NO:32, XIV12_1 corresponds to SEQ ID NO:34, XIV26_6 corresponds to SEQ ID NO:30, XIV5_1 corresponds to SEQ ID NO:33, XIV48_1 corresponds to SEQ ID NO:54, XIV25_1 corresponds to SEQ ID NO:55, and XIV37_1 corresponds to SEQ ID NO:56. It is observed that the sequences belonging to groups 1 and 2 also have a clear structural relationship. The folding free energies corresponding to each sequence (Kcal/mol) are ΔG[XIV22]=−10.80; ΔG[XIV1]=−11.80; ΔG[XIV32]=−10.80; ΔG[XIV12]=−10.90; ΔG[XIV26]=−15.70; ΔG[XIV5]=−11.10; ΔG[XIV48]=−9.80; ΔG[XIV37]=−7.32; ΔG[XIV25]=−11.50. More details in the text.

FIG. 6.—Sequences of rounds IX to XIV containing the sequence motif 5'-GGCARGGA-3' with structure in dot-bracket notation ((((........))). By aligning the sequences around said motif, the great degeneracy in the nucleotides that make up the 4 bp stem that closes the loop of conserved sequence is shown. In FIG. 6, IX03-1 corresponds to SEQ ID NO:10, IX24-1 corresponds to SEQ ID NO:11, IX36-1 corresponds to SEQ ID NO:12, X02-1 corresponds to SEQ ID NO:13, X04-2 corresponds to SEQ ID NO:14, X09-1 corresponds to SEQ ID NO:15, X10-7 corresponds to SEQ ID NO:16, X13-1 corresponds to SEQ ID NO:17, X36-1 corresponds to SEQ ID NO:18, X41-2 corresponds to SEQ ID NO:19, XI1-17 corresponds to SEQ ID NO:20, XI21-7 corresponds to SEQ ID NO:21, XI23-3 corresponds to SEQ ID NO:22, XI141-2 corresponds to SEQ ID NO:23, XI13-1 corresponds to SEQ ID NO:24, XI101-1 corresponds to SEQ ID NO:24, XI149-1 corresponds to SEQ ID NO:26, XI107-1 corresponds to SEQ ID NO:27, XI129-1 corresponds to SEQ ID NO:28, XIV22-23 corresponds to SEQ ID NO:29, XIV26-6 corresponds to SEQ ID NO:30, XIV1-2 corresponds to SEQ ID NO:31, XIV32-1 corresponds to SEQ ID NO:32, XIV5-1 corresponds to SEQ ID NO:33, and XIV12-1 corresponds to SEQ ID NO:34. Further, the Consensus motif shown corresponds to SEQ ID NO:8.

FIG. 7.—Secondary structure corresponding to the RNA16(+) molecule with the sequence 5'-CCCCG-GCAAGGAGGGG-3' (SEQ ID No. 35), considered the minimum motif to specifically interact with the HIV-1 5'UTR. The free energy associated with that MFE is −6.50 kcal/mol, and the frequency of said MFE within the structural repertoire (ED) of this sequence is 91.82%.

FIG. 8.—Bioinformatics prediction of interactions between the target $UTR_{308}$ (SEQ ID No: 1) and four of the molecules generated in the present invention: aptamers XIV22-23 (example of group 2a), XIV1-2 (group 2b), XIV26-6 (group 1), and the RNA16(+) molecule. (A) and (B) graphically show the total free energy of the possible interactions of regions of the $UTR_{308}$ molecule (SEQ ID No: 1) with the four molecules studied. The positions (nt) of the regions of the $UTR_{308}$ are depicted on the X axis and the value of total free energy of binding on the Y axis. The six valleys that correlate with potential binding areas of $UTR_{308}$ to the aptamers are marked from (a) to (f). (C) shows, marked from (a) to (e) as in panels (A) and (B), the five possible interaction regions of the aptamers with the $UTR_{308}$ molecule folded in BMH shape. Region (a), located on the Poly-A domain, is the one that generates the most stable interaction: the pairing with the motif 5'-GGCAAGGA-3' (framed) is shown for it, identified in the four molecules studied XIV22-23 (SEQ ID No: 29), XIV1-2 (SEQ ID No: 31), XIV26-6 (SEQ ID No: 30) and RNA16(+) (SEQ ID No: 35).

FIG. 9.—Scheme of inhibitory RNAs L-XIV22-23 (SEQ ID No: 37) and L-XIV26-6 (SEQ ID No: 38) used in the in vitro binding assays to the $UTR_{308}$ region (SEQ ID No: 1) and in the assays of inhibition of HIV-1 in cell cultures. Aptamers XIV22-23 and XIV26-6 were cloned between the KpnI and ApaI sites of vector pU6 (Sánchez-Luque et al., 2010). The empty construct was used as control RNA (called L-empty).

Figure 10:
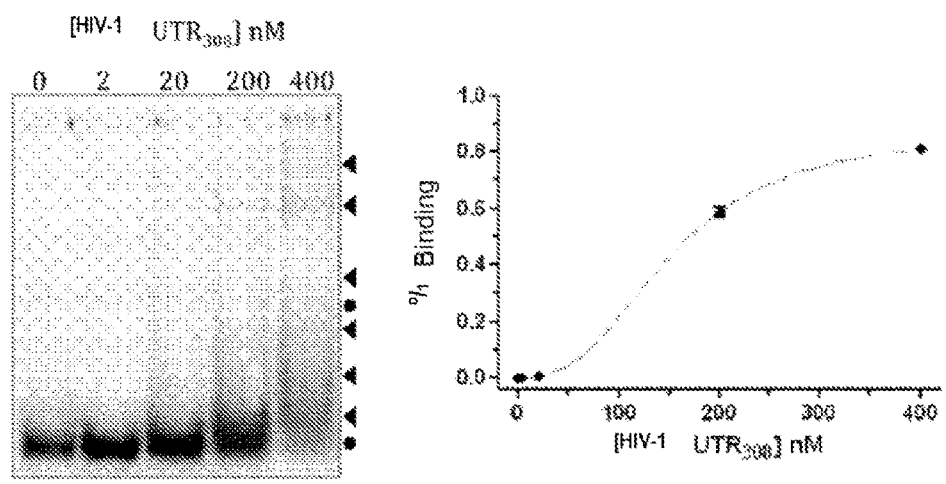

FIG. 10.—Example of binding of molecule L-XIV22-23 (SEQ ID No: 37) to the $UTR_{308}$ molecule (SEQ ID No: 1). An autoradiograph of the result of the native gel electrophoresis of the binding reactions of the molecule L-XIV22-23 (SEQ ID No: 37) at increasing concentrations of $UTR_{308}$ molecule (SEQ ID No: 1) is shown to the left. The dots that appear to the right of the gel indicate the different conformers of the unbound molecule L-XIV22-23 (SEQ ID No: 37), since they are already detected in the first lane (where there is no target molecule). Arrowheads indicate binding complexes between the two molecules. Total quantification of the binding complexes divided by the total quantification of complexes and free molecule result in per unit ($°/_1$) binding. The graph to the right shows the mean and the standard error of three independent experiments. The curve to which the binding of this molecule fits follows the model of cooperative binding with a single binding site and is shown as a dotted line.

Figure 11:
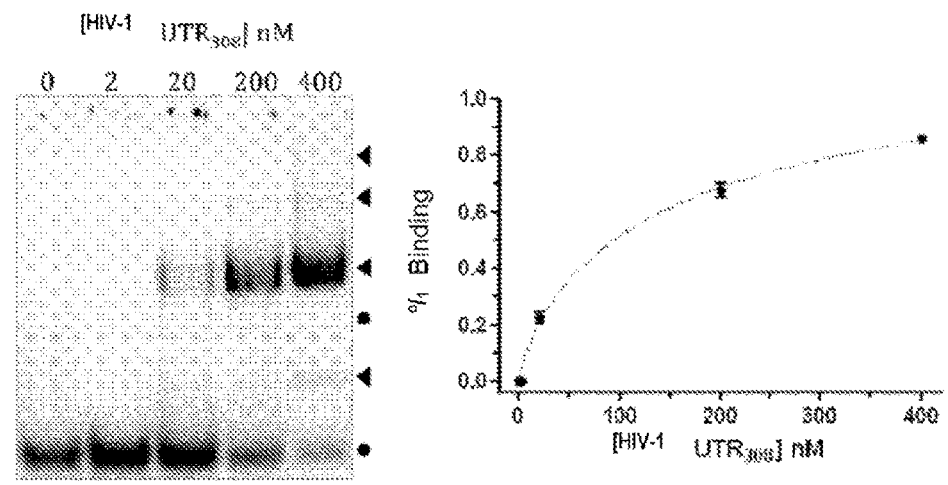

FIG. 11.—Example of binding of molecule L-XIV26-6 (SEQ ID No: 38) to the $UTR_{308}$ molecule (SEQ ID No: 1). An autoradiograph of the result of the native gel electrophoresis of the binding reactions of the molecule L-XIV26-6 (SEQ ID No: 38) at increasing concentrations of $UTR_{308}$ molecule (SEQ ID No: 1) is shown to the left. The dots that appear to the right of the gel indicate the different conformers of the unbound molecule L-XIV26-6 (SEQ ID No: 38), since they are already detected in the first lane (where there is no target molecule). Arrowheads indicate binding complexes between the two molecules. Total quantification of the binding complexes divided by the total quantification of complexes and free molecule result in per unit ($°/_1$) binding. The graph to the right shows the mean and the standard error of three independent experiments. The curve to which the binding of this molecule fits follows a hyperbolic model and is shown as a dotted line.

Figure 12:
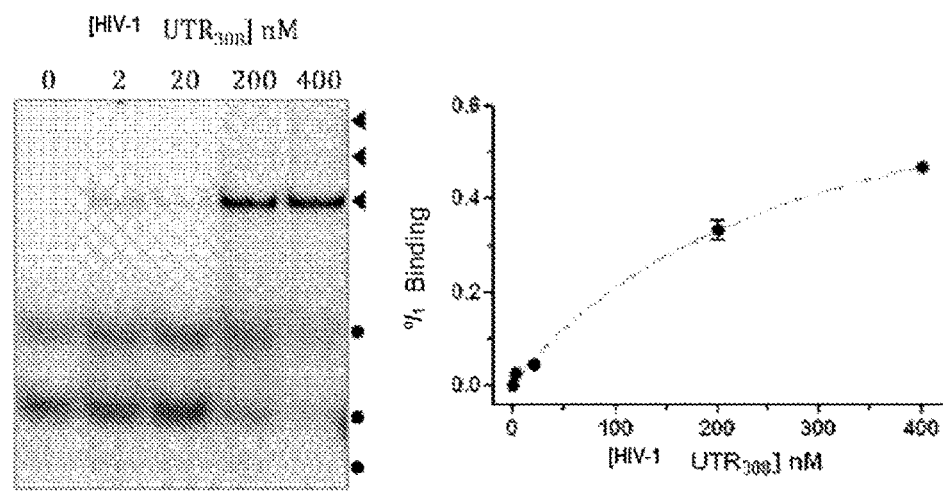

FIG. 12.—Example of binding of RNA16(+) molecule (SEQ ID No: 35) to the $UTR_{308}$ molecule (SEQ ID No: 1). An autoradiograph of the result of the native gel electrophoresis of the binding reactions of the RNA16(+) molecule (SEQ ID No: 35) at increasing concentrations of $UTR_{308}$ molecule (SEQ ID No: 1) is shown to the left. The dots that appear to the right of the gel indicate the different conformers of the unbound RNA16(+) molecule (SEQ ID No: 35), since they are already detected in the first lane (where there is no target molecule). Arrowheads indicate binding complexes between the two molecules. Total quantification of the binding complexes divided by the total quantification of complexes and free molecule result in per unit ($°/_1$) binding. The graph to the right shows the mean and the standard error of three independent experiments. The curve to which the binding of this molecule fits follows a hyperbolic model and is shown as a dotted line.

Figure 13:
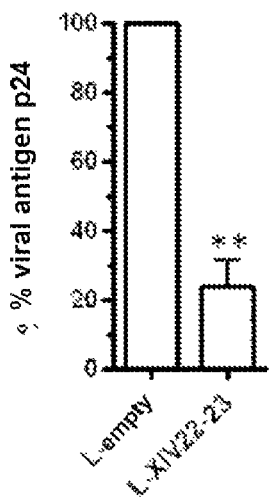

FIG. 13.—Example of inhibition of replication of HIV-1 in cell cultures by molecule L-XIV22-23 (SEQ ID No: 37). The figure shows the result of the quantification of viral antigen p24 in the cell supernatant of HEK293T cell cultures cotransfected with 100 ng of pNL4-3 and 500 ng of inhibitory RNA 48 hrs prior to measurement. The graph shows the mean and the standard error in three independent experiments of the percentage of antigen p24 with respect to the one registered with the L-empty control RNA in each triplicate. ANOVA analysis shows that differences are statistically significant (** reflects p-value <0.01).

Figure 14:
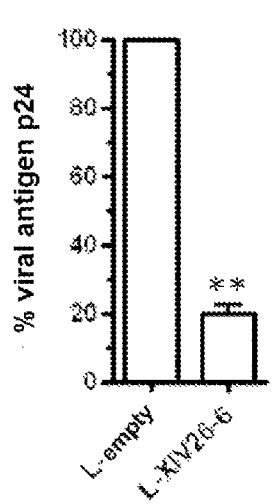

FIG. 14.—Example of inhibition of replication of HIV-1 in cell cultures by the molecule L-XIV26-6 (SEQ ID No: 38). The figure shows the result of the quantification of viral antigen p24 in the cell supernatant of HEK293T cell cultures cotransfected with 100 ng of pNL4-3 and 500 ng of inhibitory RNA 48 hrs prior to measurement. The graph shows the mean and the standard error in three independent experiments of the percentage of antigen p24 with respect to the one registered with the L-empty control RNA in each triplicate. ANOVA analysis shows that differences are statistically significant (** reflects p-value <0.01).

Figure 15:
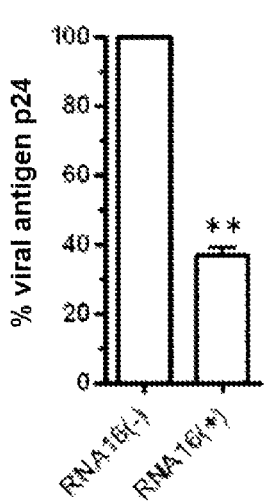

FIG. 15.—Example of inhibition of replication of HIV-1 in cell cultures by the RNA16(+) molecule (SEQ ID No: 35). The figure shows the result of the quantification of viral antigen p24 in the cell supernatant of HEK293T cell cultures cotransfected with 100 ng of pNL4-3 and 500 ng of inhibitory RNA 48 hrs prior to measurement. The graph shows the mean and the standard error in three independent experiments of the percentage of antigen p24 with respect to the one registered with the control RNA RNA16(−) in each triplicate. ANOVA analysis shows that differences are statistically significant (** reflects p-value <0.01).

Figure 16:
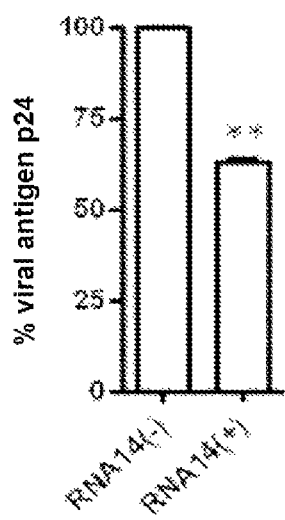

FIG. 16.—Example of inhibition of replication of HIV-1 in cell cultures by the molecule RNA14(+) (SEQ ID No: 50). The figure shows the result of the quantification of viral antigen p24 in the cell supernatant of HEK293T cell cultures cotransfected with 100 ng of pNL4-3 and 500 ng of inhibitory RNA 48 hrs prior to measurement. The graph shows the mean and the standard error in three independent experiments of the percentage of antigen p24 with respect to the one registered with the control RNA RNA14(−) (SEQ ID No: 51) in each triplicate. ANOVA analysis shows that differences are statistically significant (* reflects p-value <0.01).

Figure 17:
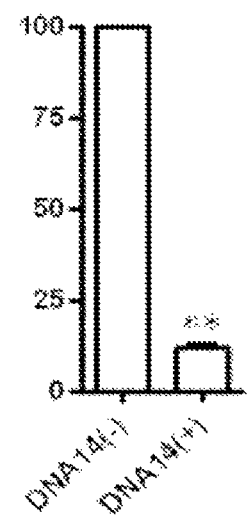

FIG. 17.—Example of inhibition of replication of HIV-1 in cell cultures by the molecule DNA14(+) (SEQ ID No: 52). The figure shows the result of the quantification of viral antigen p24 in the cell supernatant of HEK293T cell cultures cotransfected with 100 ng of pNL4-3 and 500 ng of Inhibitory DNA 48 hrs prior to measurement. The graph shows the mean and the standard error in three independent experiments of the percentage of antigen p24 with respect to the one registered with the control RNA DNA14(−) (SEQ ID No: 53) in each triplicate. ANOVA analysis shows that differences are statistically significant (** reflects p-value <0.01).

EXAMPLES OF EMBODIMENT OF THE INVENTION

The aptamers developed have as minimum common sequence to all of them the octanucleotide 5'-GGCARGGA-3' (IUB notation for degenerate nt: R corresponds to A or G), that is, 5'-GGCAAGGA-3' or 5'-GGCAGGGA-3'. In both cases, this sequence forms a single-stranded terminal loop closing a double-stranded stem of at least three pairs of nucleotides. The aptamers containing these minimum sequences can have flanking regions both at their 5' and 3' ends with lengths comprised between 1 and 75 nucleotides. Said flanking regions may form any structure or provide any additional functionality. In particular, aptamers of a total length of 64 nucleotides have been developed in the present invention, all of which contain the indicated octanucleotides (Examples 1 and 2).

Based on this knowledge and on the aforementioned in vitro/in silico combined approach, it has been possible to define a specific RNA molecule of only 16 nucleotides, called "RNA16(+)", with the sequence SEQ ID No: 35 (5'-CCCCGGCAAGGAGGGG-3'). This molecule contains the motif 5'-GGCAAGGA-3' in a terminal loop closing a very stable stem of 4 base pairs G-C (Example 3). Said RNA16(+) molecule was synthesized and it was subjected to the same assays as the aptamers of 64 nucleotides obtained by in vitro selection.

It has been observed by means of bioinformatic analysis that the aptamers obtained in vitro and the RNA16(+) molecule specifically bind to the Poly-A domain of the HIV-1 5'UTR (Example 4).

The specific interaction between the selected aptamers or the RNA16(+) molecule and the HIV-1 5'UTR has been verified in vitro (Examples 5.1 to 5.3). Moreover, it has been demonstrated that the aptamer-ligand binding, or RNA16 (+)-ligand binding, inhibits the replication of HIV-1 in cell culture, as determined by means of specific assays (Examples 5.4 a 5.6).

Example 1.—Process for Obtaining Aptamers by In Vitro Selection

A process of in vitro selection of RNA aptamers with the ability to specifically bind to the HIV-1 5'UTR was carried out. The starting population used, called "Round 0" was generated by in vitro transcription (IVT) using the T7 RNA polymerase enzyme and a synthetic template. This template consisted of a set of DNA molecules of 84 nucleotides (nt) in length obtained by hybridization and extension of the oligonucleotides 5'EcoRIK (SEQ ID No: 40, 5'-GGA-TAATACGACTCACTATAGGGAATTCAA-3'), which incorporates the promoter of the T7 RNA polimerase, and 3'RANDOMK (SEQ ID No: 41, 5'-GTCGAGCTCGTAG-TATCAGATCACTC-CATNNNNNNNNNNNNNNNNNNNNN NNNNTT-GAATTCCCTATAGTG-3'), wherein N indicates each of the 25 random positions. Thus, the result is a population of RNA molecules (Round 0) of 64 nt in length which vary from each other only in the central region of 25 nt with random sequence, flanked by two fixed sequence regions, to which the primer oligonucleotides or primers used during the process will bind.

The target molecule used for the selection of aptamers was a fragment of 308 nt that corresponds to the 5'UTR of the HIV-1 genome cloned into plasmid pNL4-3 HIV-1 (abbreviated $UTR_{308}$), and with the sequence SEQ ID No: 1. Said target was obtained by IVT from a DNA molecule generated by PCR using the oligonucleotides 5'T7pNL4-3 (SEQ ID No: 43, 5'-TAATACGACTCAC-TATAGGGTCTCTCTGGTTAG-3') and 3'T7pNL4-3 (SEQ ID No: 44, 5'-AATTTTTGGCGTACTCACCAGT-3'). The use as a target of a fragment containing the first 308 nucleotides out of the total 336 nucleotides of the 5'UTR allows the selection of aptamers against said region in a structural environment that represents the natural situation in the genome of the virus, which had not been previously achieved by other authors who have used isolated structural elements of the 5'UTR as a target, for example the element TAR (Ducongé and Toulmé, 1999; Kolb et al., 2006; Watrin et al., 2009).

The process of synthesis of a target molecule of this type, described in detail in (Romero-López et al., 2005), included the internal biotinylation during the IVT process, through the addition of biotinylated UTP to the reaction mixture at a final concentration of 0.106 mM. On average, the inclusion of one UMP biotinylated nucleotide per target molecule can be obtained. IVT reaction was conducted at 37° C. for 2 hours, and the DNA template was removed using DNase RQ1 (Promega) at 1 U/μg DNA, by means of a reaction at 37° C. for 30 minutes. The transcription product was purified by polyacrylamide gel electrophoresis.

The biotinylated $UTR_{308}$ molecule was bound to a Sefarose HiTrap™ Streptavidine HP (GE Healthcare) column. For this, all the product of the transcription of the target was precipitated using ethanol and resuspended in 1 ml of binding buffer recommended by the manufacturer of the columns. The target molecule population was renatured by means of an incubation at 64° C. for 10 minutes, followed by an additional incubation at 37° C. for 10 minutes. Finally, this population was introduced into a Sepharose column previously equilibrated with the passage of 10 ml of binding buffer. After this, the column was washed with 10 ml more of binding buffer and equilibrated with 10 ml of 1×TMN (20 mM TRIS-acetate; 10 mM magnesium acetate; 100 mM sodium chloride).

To begin the process of in vitro selection, the population of 64 nt RNA known as "Round 0" was precipitated using ethanol and resuspended in 1 ml of 1×TMN buffer. The RNA was renatured in this buffer by means of incubation at 64° C. for 10 minutes, followed by an additional incubation at 37° C. for 10 minutes. In order to eliminate the population of those RNA molecules that could nonspecifically bind to the Sepharose present in the columns, a negative selection was performed by coupling a streptavidin-sepharose column in tandem over the one containing the bound target molecule. This empty column was also equilibrated with 10 ml of 1×TMN. The renatured RNA that corresponds to the Round 0 was introduced in the tandem columns and a second volume of 1×TMN was passed such that it moved forward to the column with the immobilized target molecule. After an incubation time of 30 minutes at 25° C., the negative selection column was removed and the molecules unbound to the column with the target were removed by washing at the same temperature with 10 ml of 1×TMN. Those molecules that bound to the sepharose or the streptavidin and not to the target would have been retained by the first column. For its part, the RNA molecules of Round 0 bound to the $UTR_{308}$ target were eluted from the column by denaturation, by passing 10 ml of 1×TMN at 95° C. through it. The first 4 fractions of 1 ml recovered were bound and concentrated using the Centricon Ultracel YM-3 system (Amicon Bio-separations, Millipore), and precipitated with ethanol.

Half of the population of bound RNA was stored at −80° C., and the rest was retrotranscribed to cDNA using the RT activity of the enzyme Tth DNA polimerase (Promega) and the primer 3'XhoIK (SEQ ID No: 42, 5'-GTCGAGCTCG-TAGTATCAGATCACTCCAT-3'). Subsequently, the cDNA obtained was amplified by PCR using the same enzyme and using the primers 3'XhoIK (SEQ ID No: 42) and 5'EcoRIK (SEQ ID No: 40, the latter including the sequence of the T7 promoter). The amplified DNA was purified with phenol, precipitated with ethanol and used as a template for an IVT reaction with which the RNA called "Round I" was obtained.

This process was repeated over 14 rounds of amplification-selection, increasing the selective pressure throughout the process. This increase in the stringency of the aptamer-target interaction was achieved by increasing the binding temperature (which was 25° C. for rounds I-III and 37° C. for IV-XIV). On its part, the aptamer-target ratio was 1:1 for rounds I-X and 1000:1 for XI-XIV. In each round, half of the amplified DNA was cloned into pGEM-T easy vector (Promega), and over 30 molecular clones obtained were sequenced.

Example 2.—Analysis of the Structure and Sequence of Aptamers Obtained by In Vitro Selection An analysis of sequence (by means of molecular cloning and sequencing) and structure (through programs for in silico folding) of 299 individual molecules corresponding to Round 0 and the 14 rounds of selection was carried out, in the amounts indicated below: Round 0, 30 seqs; Round I, 30; Round III, 31; Round V, 24; Round VIII, 28; Round IX, 32; Round X, 35; Round XI, 52; Round XIV, 37. Of the 299 molecules, 216 were unique, with the other being repeated sequences. It was found that among the 216 molecules, 188 had the expected length of 64 nt while the rest had deletions of 1 or more nucleotides in the variable region. Sequence analysis by means of alignment and comparison programs showed that in several cases some of the sequences were repeated, both within a single round and in different rounds. The repeated sequences obtained are shown in Table 1.

The distance between sequences of each round, measured as number of mutations among them (Hamming distance) was estimated. Although the total length of the sequence is 64 nt, the maximum distance is 25 (variable region). It was noted that from round IX groups of clearly differentiated sequences started to be defined, indicating that the selection process was being efficient.

All the complete sequences (64 nt) were folded in their minimum energy structure or "MFE structure" using the RNAfold program of the "Vienna RNA package" version 1.5, with the energy parameters described in (Mathews et al., 1999), without allowing the presence of isolated base pairs, and defining as minimum length for a double-stranded stem 2 base pairs (bp). These folded and aligned structures, represented by the dot-bracket notation (in which the unpaired nucleotides are indicated by dots, and the ones forming part of base pairs by brackets), are likely to be compared with each other and thus calculate the distance between them. Said distance between structures was measured using three different methods:

i) Hamming: The symbol between two aligned structures is compared position to position [".", "(" or ")"], and when they are different the distance for that position is computed as 1. The total distance between the two structures will be the sum of the distances for each position.

ii) Base pair. The distance between two structures is equal to the number of base pairs that must be broken and formed again later to pass from one structure to the other.

iii) Tree edit: It is calculated using the representation of the structures as trees (where a pair becomes a node) and allowing some kind of operations, such as inser-

TABLE 1

Repeated sequences present throughout the process of in vitro selection, free energy associated to the MFE in each case and group to which they belong

| $0^a$ | I | III | V | VIII | $IX^b$ | X | XI | XIV | ΔG of the MFE (Kcal/mol) | Group$^c$ |
|---|---|---|---|---|---|---|---|---|---|---|
| 016-2 | | | | | | | | | −10.70 | |
| 029-2 | | | | | | | | | −8.60 | |
| | | III45B-2 | | | | | | | −5.10 | |
| | | | | | IX05-3 | X05-12 | XI73-3 | | −4.03 | Gr. 3 |
| | | | | | IX08-2 | | | | −11.10 | |
| | | | | | IX36 | X10-7 | XI1-17 | XIV22-23 | −10.80 | Gr. 2a |
| | | | | | | X04-2 | XI23-3 | | −20.20 | Gr. 1 |
| | | | | | | X11-2 | | | −6.61 | |
| | | | | | | | XI21-7 | XIV26-6 | −15.70 | Gr. 1 |
| | | | | | | | XI141-2 | XIV1-2 | −11.80 | Gr. 2b |
| | | | | | | X41-2 | | | −15.20 | |

Note:
$^a$equal sequences present in different rounds are shown on the same line; repeated sequences within each round are indicated with the notation "Seq-R", where R is the number of repetitions (for example, XIV22-23 means that of the sequence exemplified by the aptamer XIV22 there are 23 equal molecules in round XIV);
$^b$sequences including the motif 5'-GGCARGGA-3' are highlighted in bold;
$^c$groups are described in the text.

Figure 2:
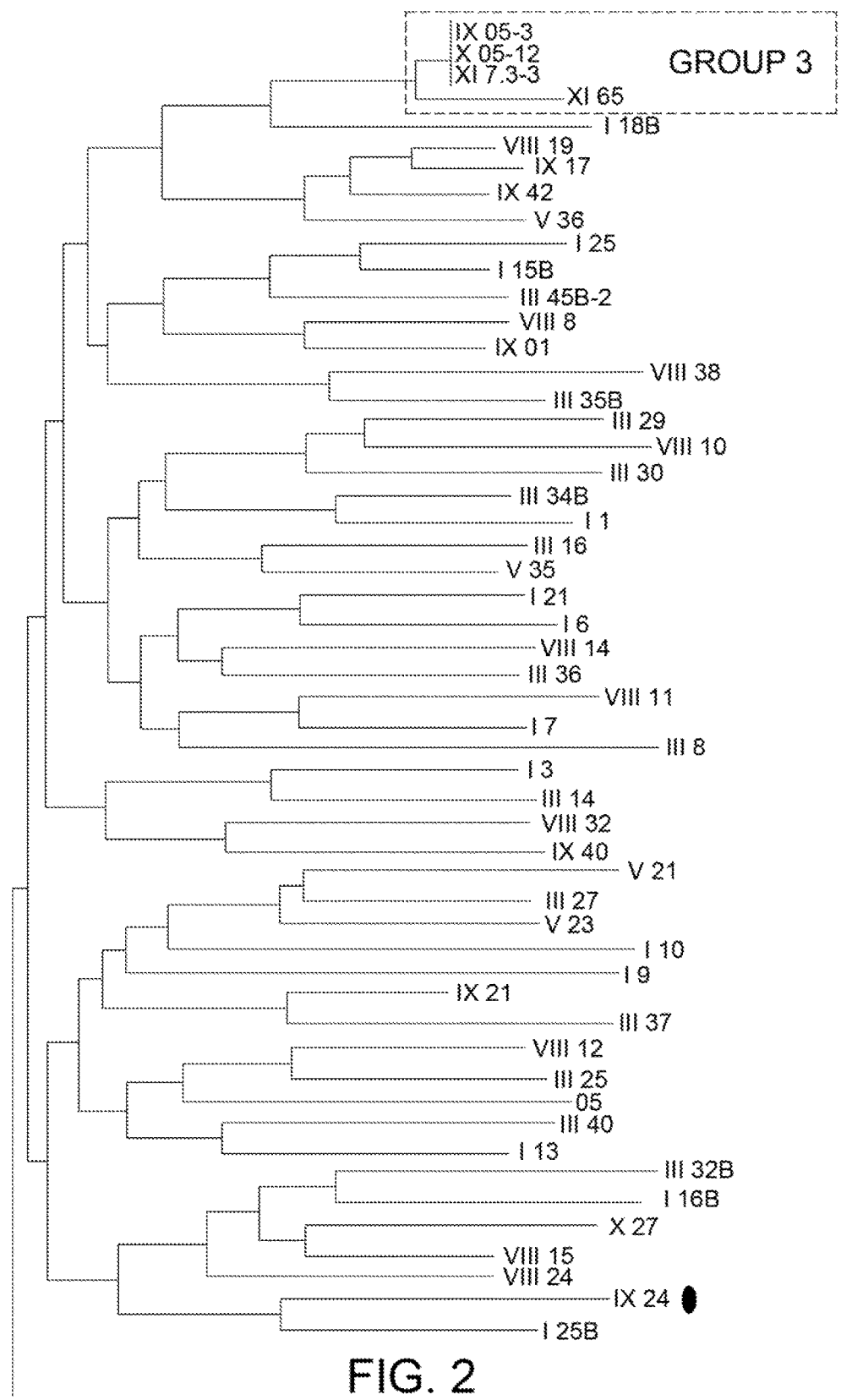
Figure 2:
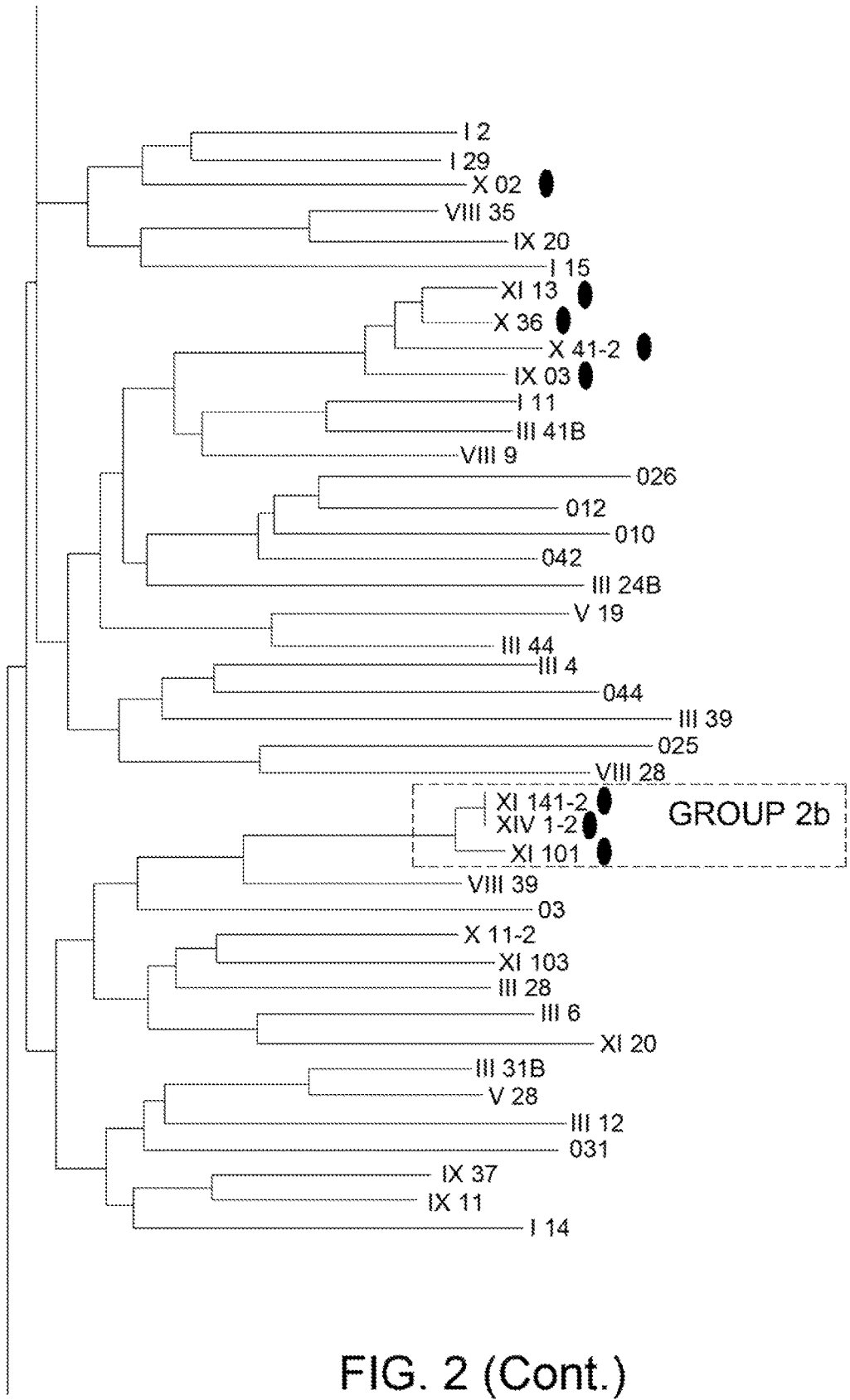
Figure 2:
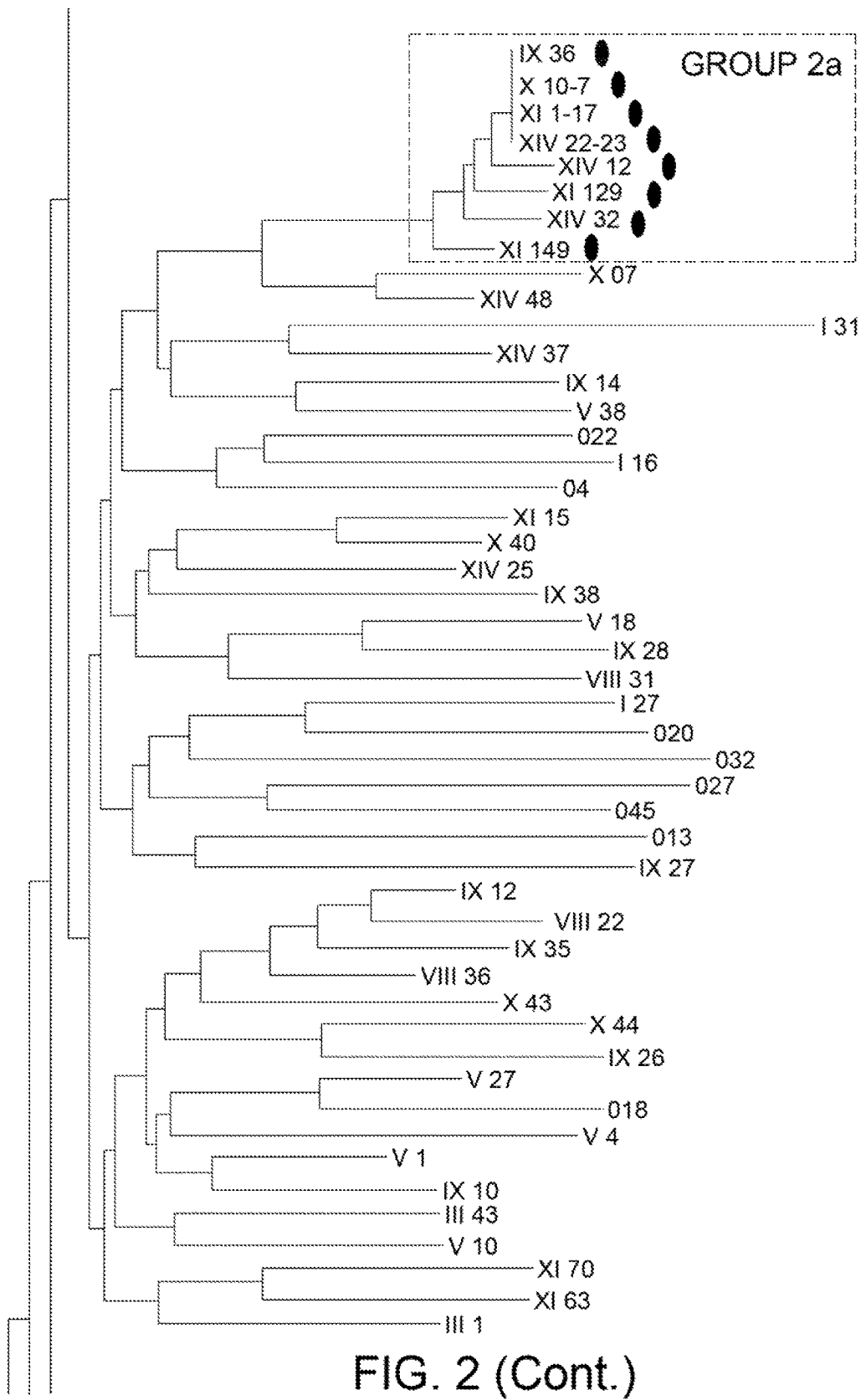
Figure 2:
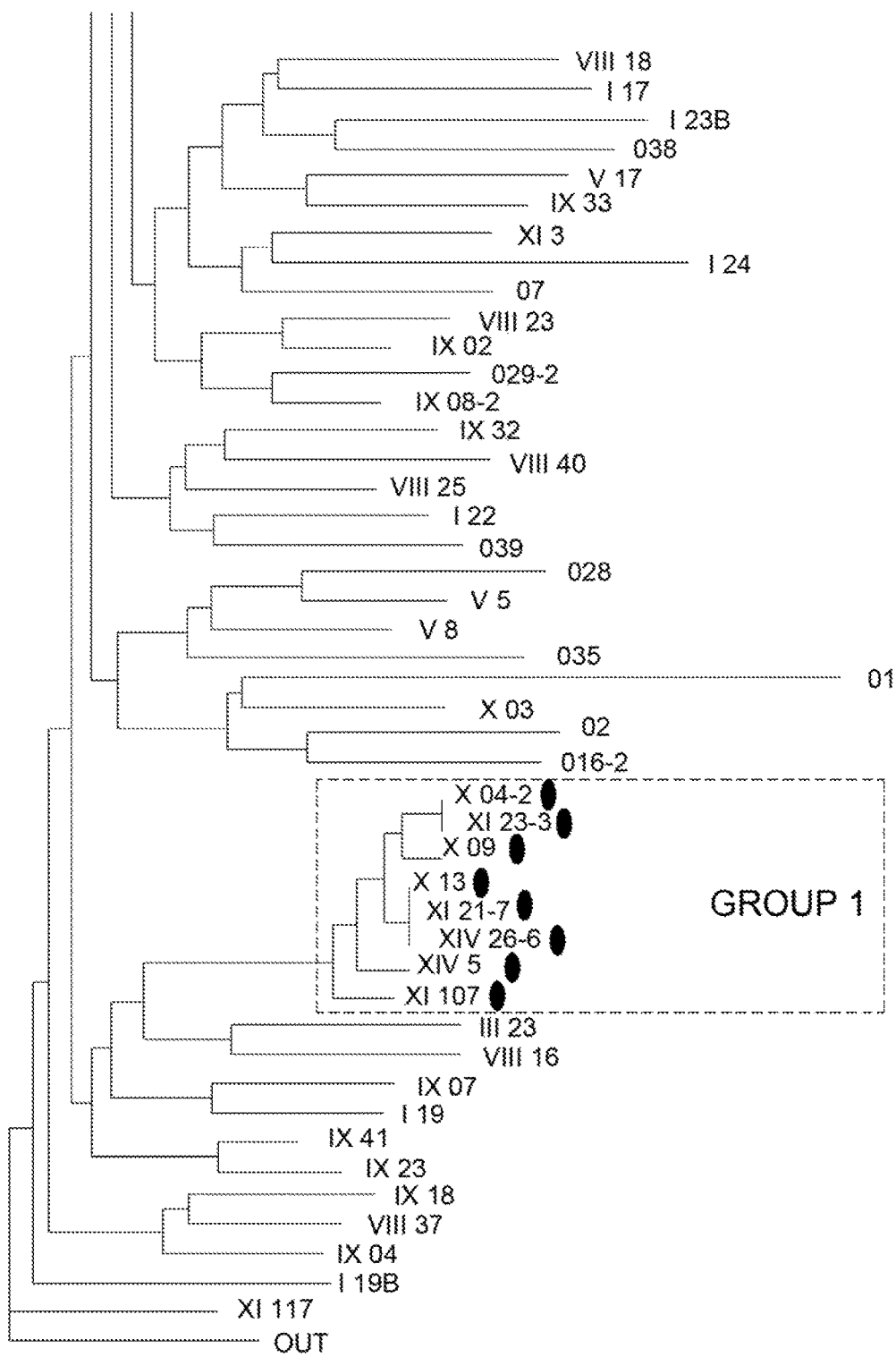

The sequences were analyzed by means of multiple alignment and clustering programs based on distances. The result of sequence clustering is shown in FIG. 2, and allowed to define three groups of sequences (the notation system is indicated in Table 1):

i) Group 1: X04-2, X09, X13, XI23-3, XI107, XI21-7, XIV5, XIV26-6 ii) Group 2:
Subgroup 2a: IX36, X10-7, XI1-17, XI129, XI149, XIV12, XIV22-23, XIV32
Subgroup 2b: XI101, XI141-2, XIV1-2 iii) Group 3: IX05-3, X05-12, XI65, XI73-3

Thus it was observed that the two groups of sequences that reached round XIV (Groups 1 and 2) had begun to be selected in round IX. On the other hand, Group 3 appeared between rounds IX and XI, but it was not represented in round XIV.

tions, deletions and substitutions. A tree edit distance is always equal or greater than a base pair distance.

Figure 3:
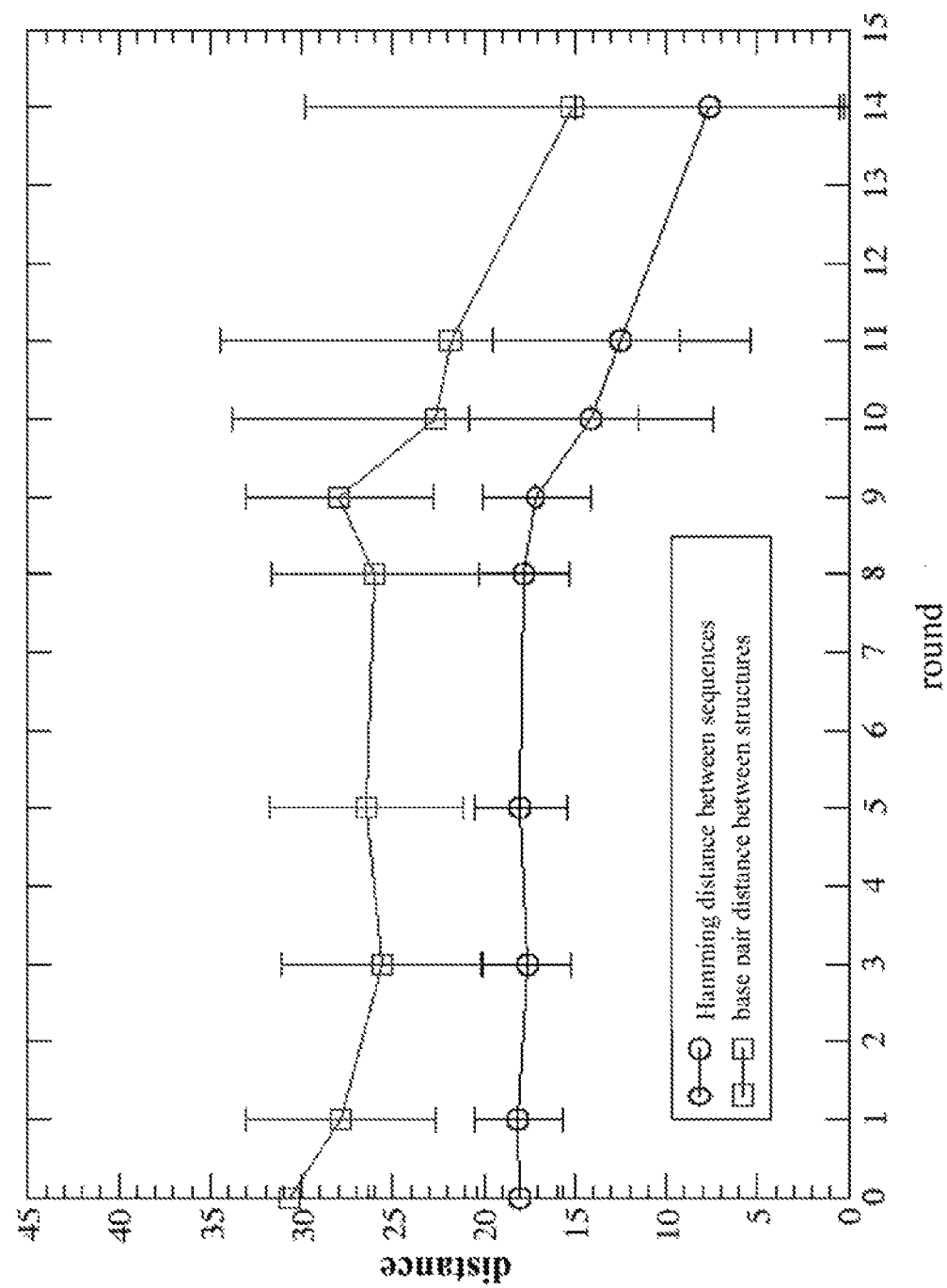

For the data set, results obtained by the three systems were qualitatively equivalent. FIG. 3 shows the progression throughout the process of in vitro selection of the distance between sequences (Hamming) and structures (base pair) within each round. A generally decreasing trend was detected in both cases, indicating the occurrence of a bias in the composition which probably reflects the presence of sequences and structures most favored for binding to the $UTR_{308}$ target (SEQ ID No: 1).

Figure 4:
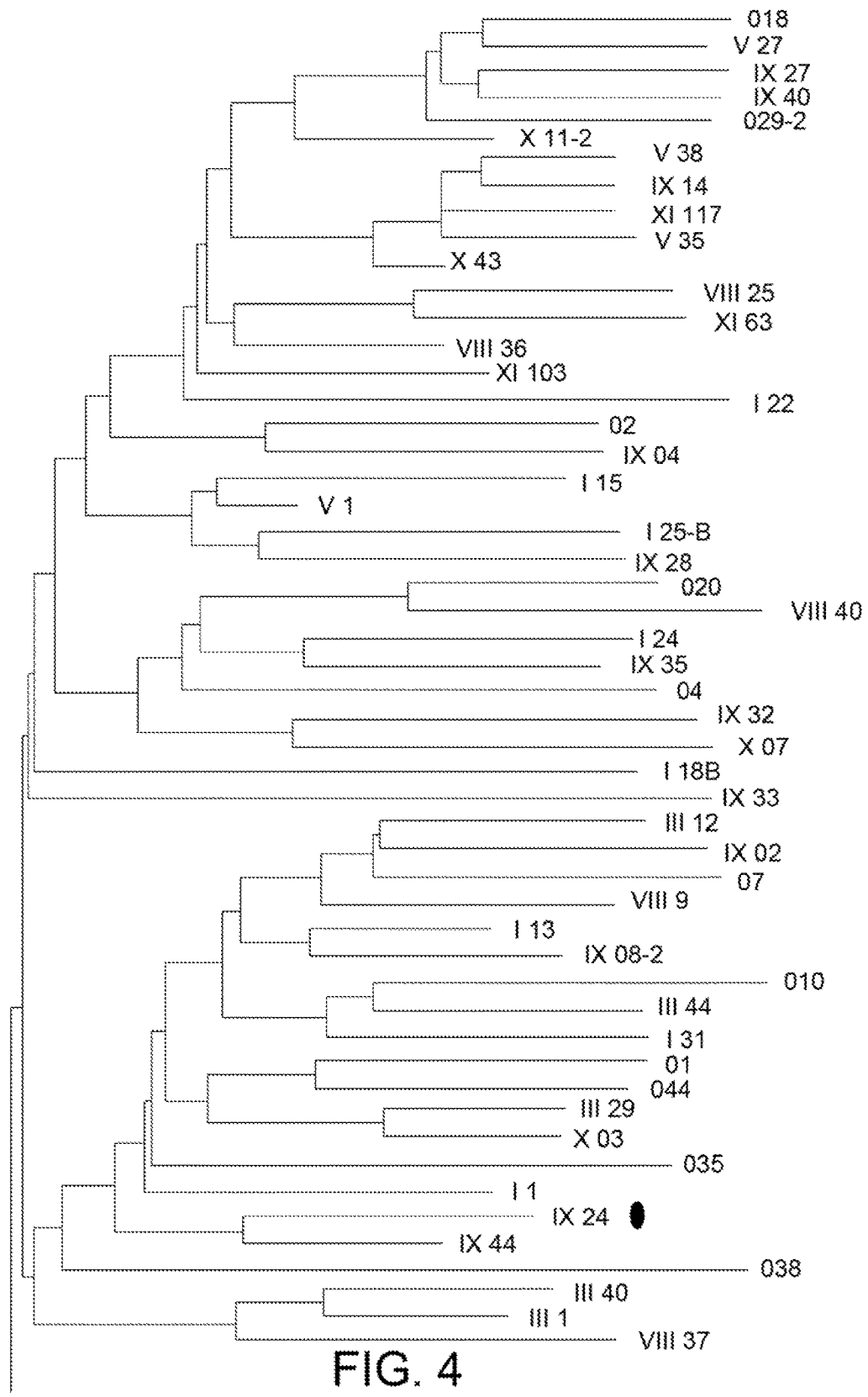
Figure 4:
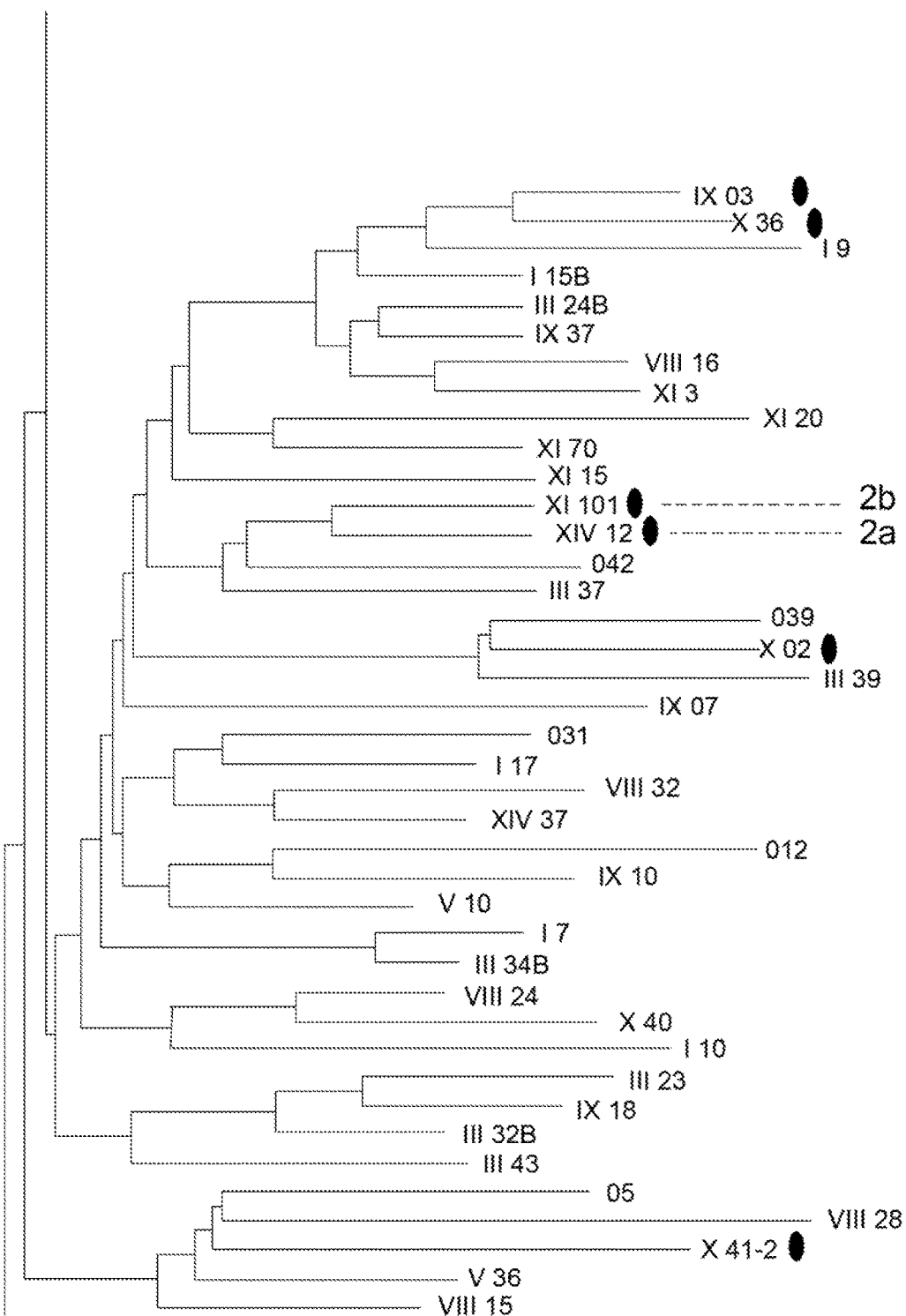
Figure 4:
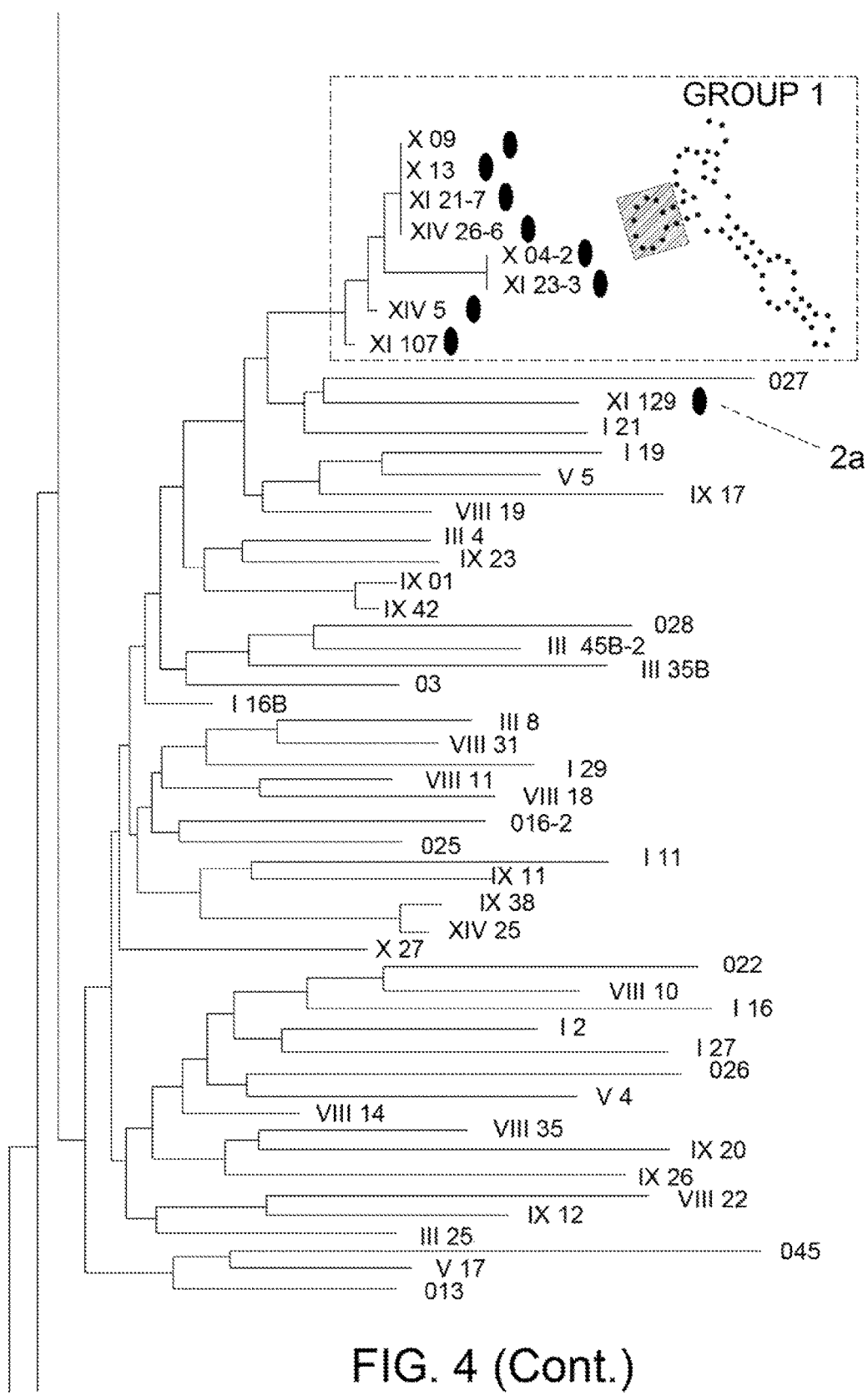
Figure 4:
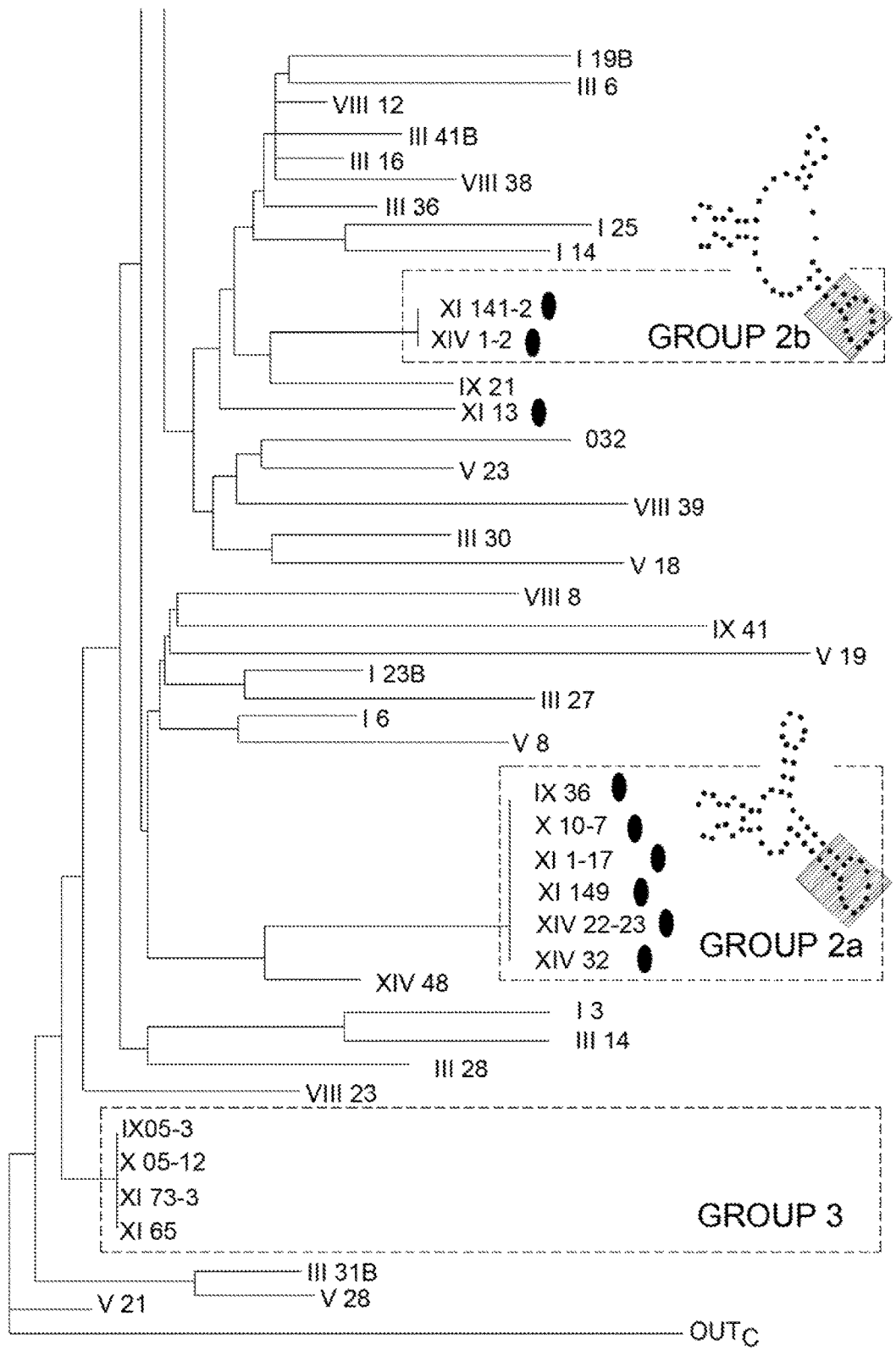

The distances between structures were analyzed by means of the same grouping or clustering programs used with the 188 sequences. The classification results obtained (for base pair distances between structures) are shown in FIG. 4. The resulting topology (equivalent to the one generated when using Hamming distances between structures) showed the presence of groups already identified in FIG. 2, which are more compact compared to the sequence groups or clusters due to the degeneracy between the spaces of sequences and structures (since different sequences fold into the same structure). Thus, Group 1 appears to form a compact cluster or grouping, with the structures equal to those displayed by XIV26-6 and those at distances of between 1 and 6 from it. In Groups 2a and 2b, the majority of the structures are identical, although three of them (XI101, XI129 and XIV12) showed folds very different from others in their group.

When jointly analyzing the sequences and their folds it was observed that there is a motif of 8 nucleotides, with the sequence 5'-GGCAAGGA-3', appearing in 25 different sequences of rounds IX, X, XI and XIV (not in the previous ones), which are the ones marked with blue dots in FIGS. 2 and 4: iv) Round IX: 03, 24, 36 v) Round X: 02, 04-2, 09, 10-7, 13, 36, 41-2 vi) Round XI: 1-17, 13, 21-7, 23-3, 101, 107, 108, 129, 141-2, 149 vii) Round XIV: 1-2, 5, 12, 22-23, 26-6

Therefore, that motif appeared in 25/216 different sequences and 86/299 total sequences. Among them, the sequence XI108 was not considered for clustering as it had a deletion of 1 nt in the variable region. It was critical to the present invention to verify that in the final round of the process (XIV), all but three of the sequences (XIV25, XIV37 and XIV48) possess this motif and belong to Groups 1 or 2 (Table 1 and FIGS. 2 and 4). Therefore, the presence of said motif (not previously described in the literature) seemed important in order for the aptamer to be selected during the process. In other words, said motif was essential for the aptamer-ligand interaction. Sequence XIV32 (Group 2a) had this same motif but with a point mutation (transition A→G in position 5 of the motif): 5'-GGCAGGGA-3'. It was found that the mutant sequence of the motif appeared exclusively in this molecule, and not in others in either this or other rounds.

It was found that all the sequences (belonging to rounds IX, X, XI and XIV) forming part of Groups 1 and 2 have the motif 5'-GGCARGGA-3' (IUB notation for degenerate nt: R corresponds to A or G). The sequences including that motif but that are not part of Groups 1 or 2 are: IX03, IX24, X02, X36, X41-2, XI13. Of these six sequences, IX03, X36, X41-2 and XI13 formed in turn a cluster well defined in FIG. 4.

Figure 5:
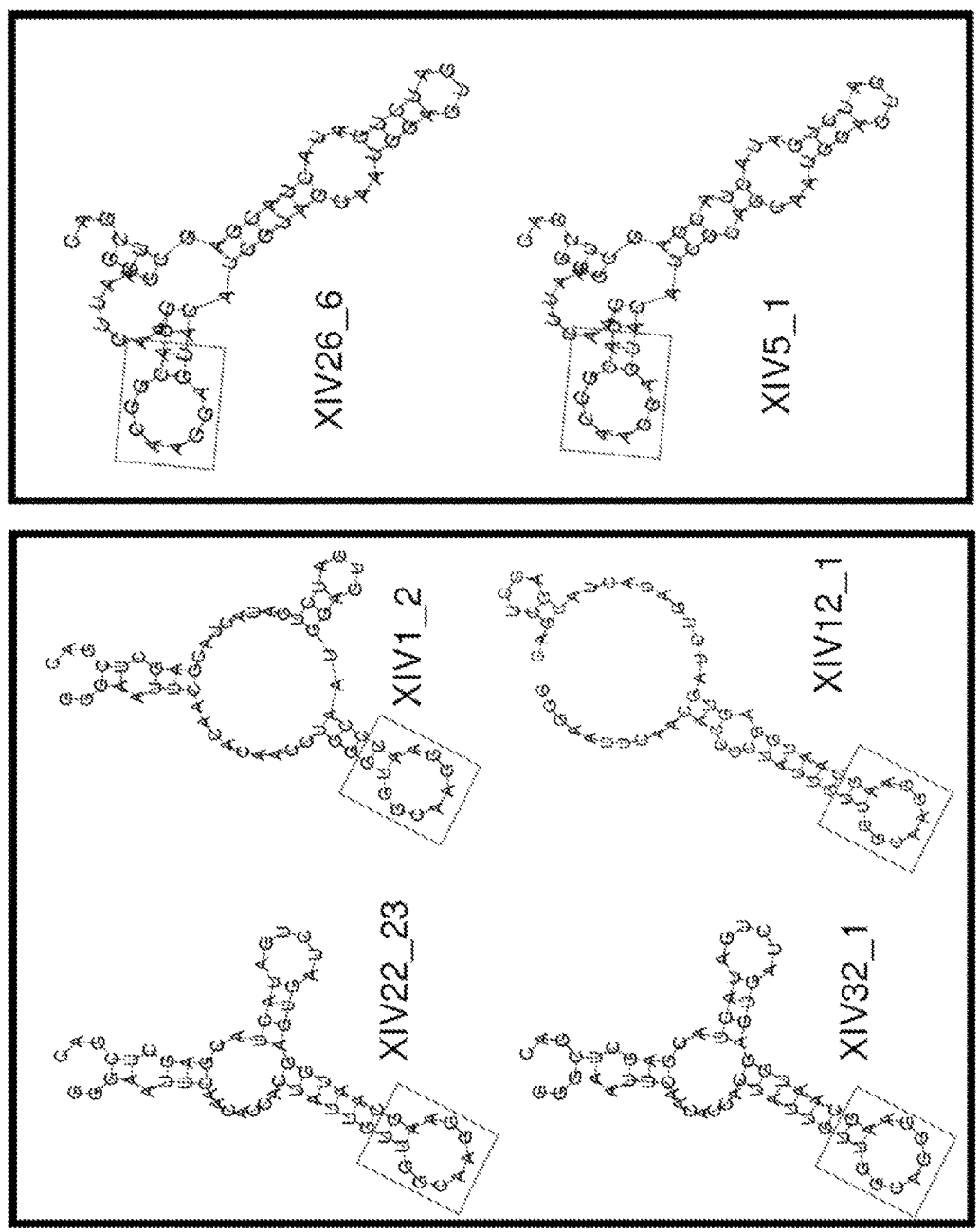
Figure 5:
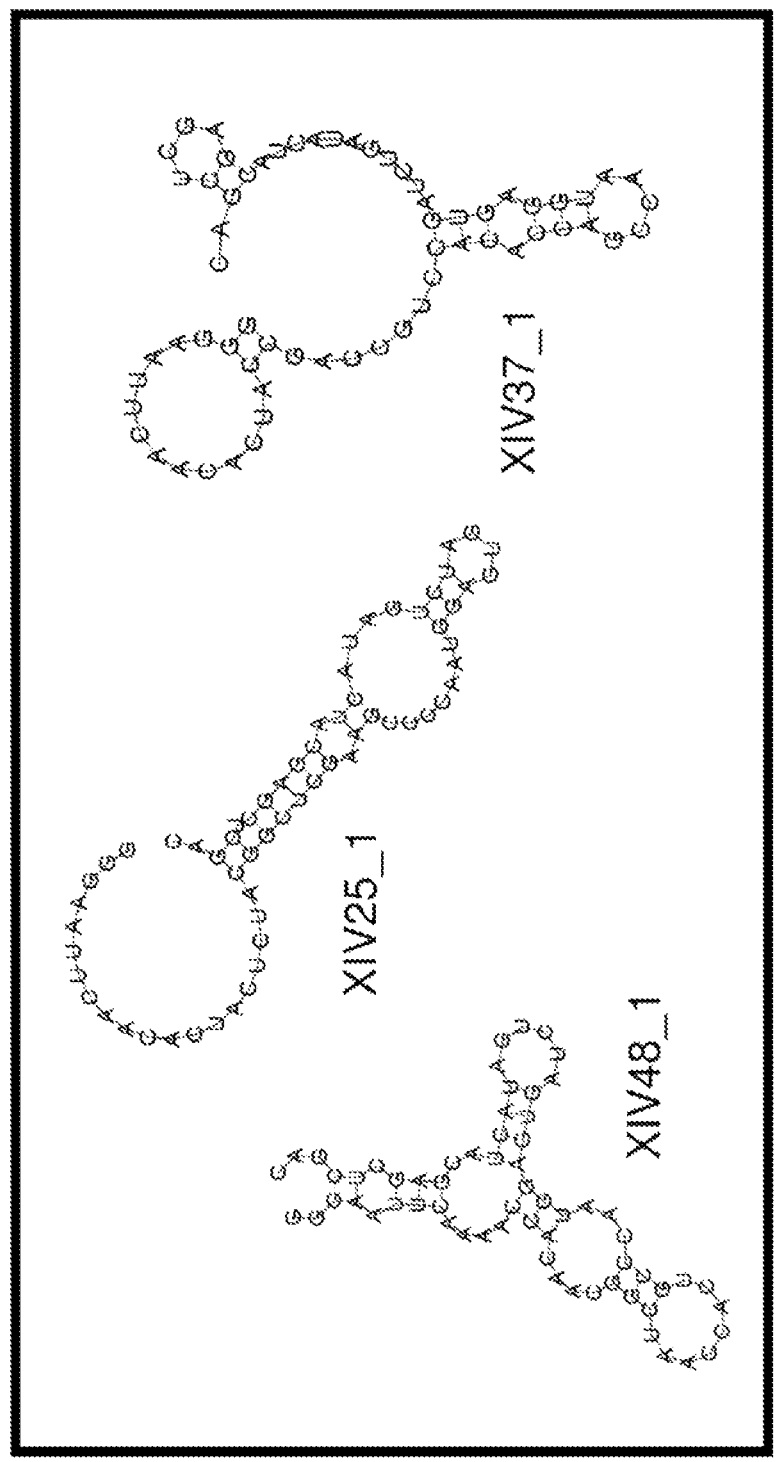

When this sequence appeared in the MFE structures in which the sequences present in round XIV (FIG. 5) folded, it was always forming an unpaired loop of 8 nt closing a stem of at least four base pairs [structure in dot-bracket ((((........))) notation]. It is worth to note that the mutation present in XIV32 does not alter the structure of this motif. The nt forming the flanking pairs of the stem closed said loop are variable. The alignment of the sequences that contain this motif (FIG. 6) showed a consensus sequence "NNDYGGCARGGARNNN" (D=A, G, U; Y=C, U; R=A, G; N=A, C, G, U) (SEQ ID NO:8).

The conserved motif NNDYGGCARGGARNNN with structure in dot-bracket ((((........)))) notation, present in the selected aptamers, was of great interest because of the following:

i) Its presence was clearly increasing in rounds IX (3 out of 32 sequences, 9.4%), X (15/35, 42.9%), XI (35/52, 67.3%) and XIV (34/37, 91.9%), and it could be correlated with the time at which the selective pressure began to increase during the experiments.

ii) The sequence of the unpaired loop present in this motif (8 nt common in a variable region of 25, that is, nearly a third of the sequence) could not have been selected randomly. The probability of a randomly selected sequence of 25 nt containing a specific motif of 8 nt is 2 in 10,000. Considering that the motif is in two sequences independently selected in round XIV: if one were to ask what the probability of obtaining the repeated motif by randomly choosing two random sequences is, the answer is once every 25 million. Furthermore, the requirement of having to form a loop at the end of a 4 bp stem considerably lowers this probability.

iii) In the sequences in which this motif appears, their common structure suggested that the 8 nt loop may interact with an unpaired region of the target molecule.

Furthermore, despite the large difference between the two structures reached in round XIV (Groups 1 and 2), it was noteworthy that this domain was present in both. Therefore, this may indicate that in the selection process molecules containing this motif were selected first (already in round IX, see Table 1 and FIG. 6) and, once that requirement was set, the motif was allowed to be surrounded by two different structural contexts: i) XIV26-6 and the rest of sequences in Group 1; ii) XIV22-23 and the rest of sequences in Group 2. Thus, a complementarity interaction of sequences between the aptamer and the target molecule UTR$_{308}$ (SEQ ID No: 1) was probably being promoted at first, and a "structural" interaction that could be of two different types would occur later.

Figure 7:
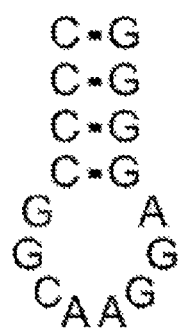

Example 3.—Process for Obtaining a Synthetic RNA Molecule of 16 nt Object of the Invention from Aptamers Obtained by In Vitro Selection According to what has been described in Example 2, we decided to use our bioinformatic analysis to design a synthetic RNA molecule of 16 nt containing the consensus motif in a terminal loop defined by a very stable 4 bp stem. Thus, the molecule called "RNA16(+)" with the sequence SEQ ID No: 35 (5'-CCCCGGCAAGGAGGGG-3') was designed and synthesized, in which four consecutive C-G pairs guaranteed the structure in dot-bracket notation ((((.......)))) as shown in FIG. 7. If the working hypothesis was correct, this RNA16(+) molecule should bind the target UTR$_{308}$ (SEQ ID No: 1) with great affinity, and eventually it may be able to inhibit the replication of HIV-1 with an efficiency similar to that shown by the aptamers of Round XIV containing the motif 5'-GGCAAGGA-3'. An interesting and novel aspect of the RNA16(+) molecule, in addition to the fact that such sequence has never been described as an HIV inhibitor, is that it was obtained by means of an in vitro/in silico combined approach. Indeed, without this combination of detailed experimental work and bioinformatic analysis the selection of the RNA16(+) molecule would not have been possible, due to the size constraints imposed by in vitro selection procedures.

Likewise, RNA and DNA molecules of 14 nucleotides, respectively called RNA14(+), the sequence of which consists of SEQ ID No: 50, and DNA14(+), the sequence of which consists of SEQ ID No: 52, were also designed and synthesized from the sequence of 16 nucleotides.

Example 4.—Bioinformatic Study of the Aptamer-Target and RNA16(+)-Target Molecule Interaction First a bioinformatic study was performed to test whether both the aptamers selected in Round XIV and the generic RNA16(+) molecule (SEQ ID No: 39) had regions of interaction mediated by base complementarity between unpaired loops with the target molecule. For this purpose, the RNAup program of the "Vienna RNA package" was used in its 1.5 version. Using this program, RNA-RNA interaction was assessed by calculating firstly the probability of a sequence interval (in this case, the unpaired loop of 8 nt) not binding anywhere in the target molecule (UTR$_{308}$, SEQ ID No: 1). Next, the binding energy corresponding to all possible cases of interaction between the two molecules was calculated. This parameter was then optimized to find the most favored interactions, that is, those that generated structures with a more negative value of free energy. The same parameters chosen for RNAfold were used. Additionally, to further explore the possible regions of interaction of the target, the pKiss and pknotsRG programs, provided by the "RNA Studio package" of the University of Bielefeld were used (bibiserv.techfak.uni-bielefeld.de), which allowed evaluating, respectively, the presence of kissing loop-type motifs and of pseudoknots of different types.

Figure 8A:
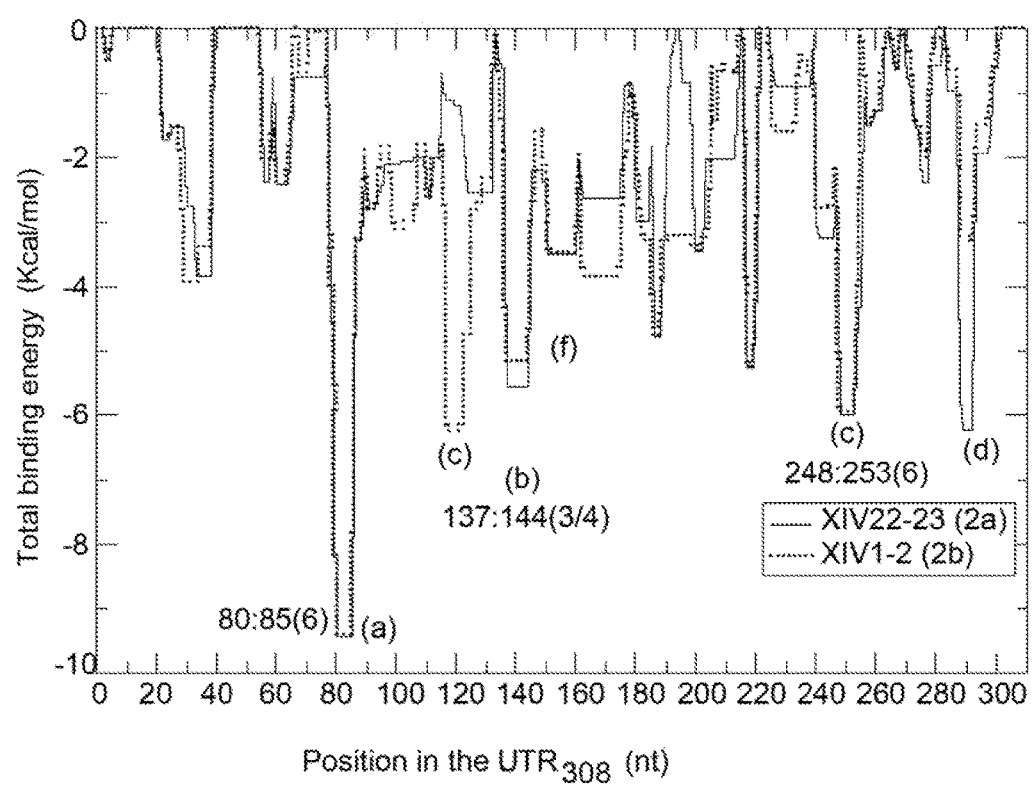
Figure 8B:
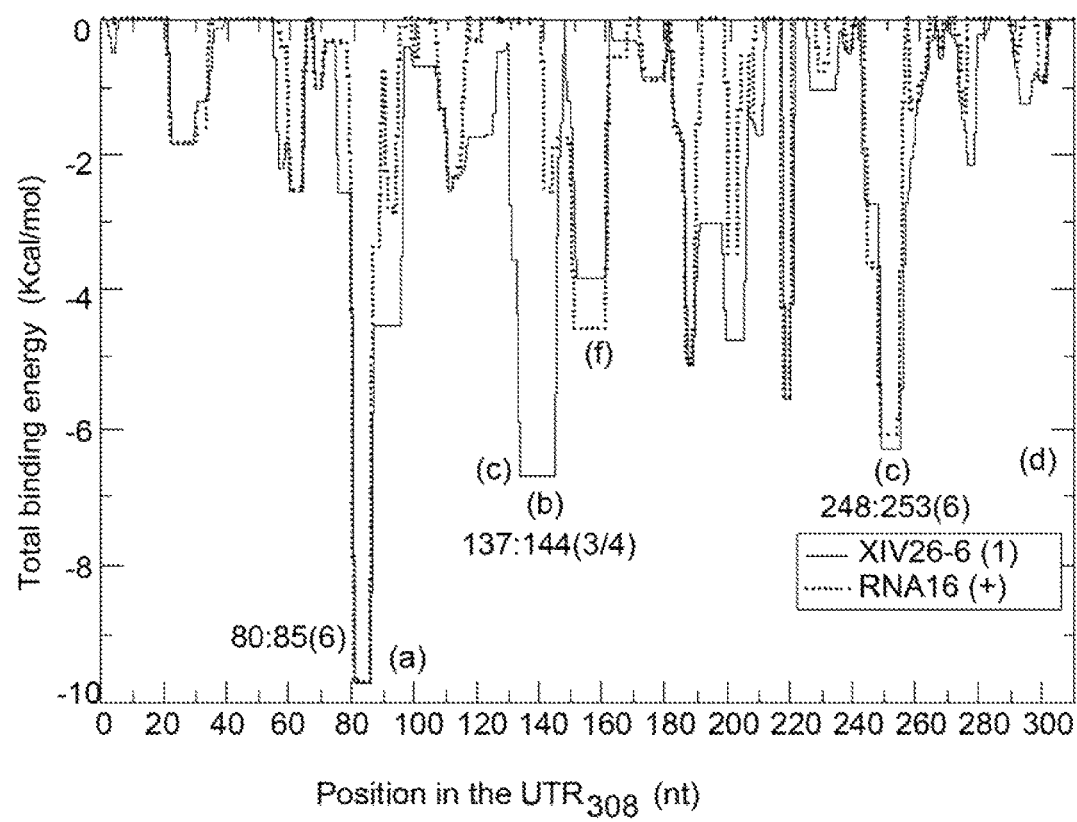
Figure 8C:
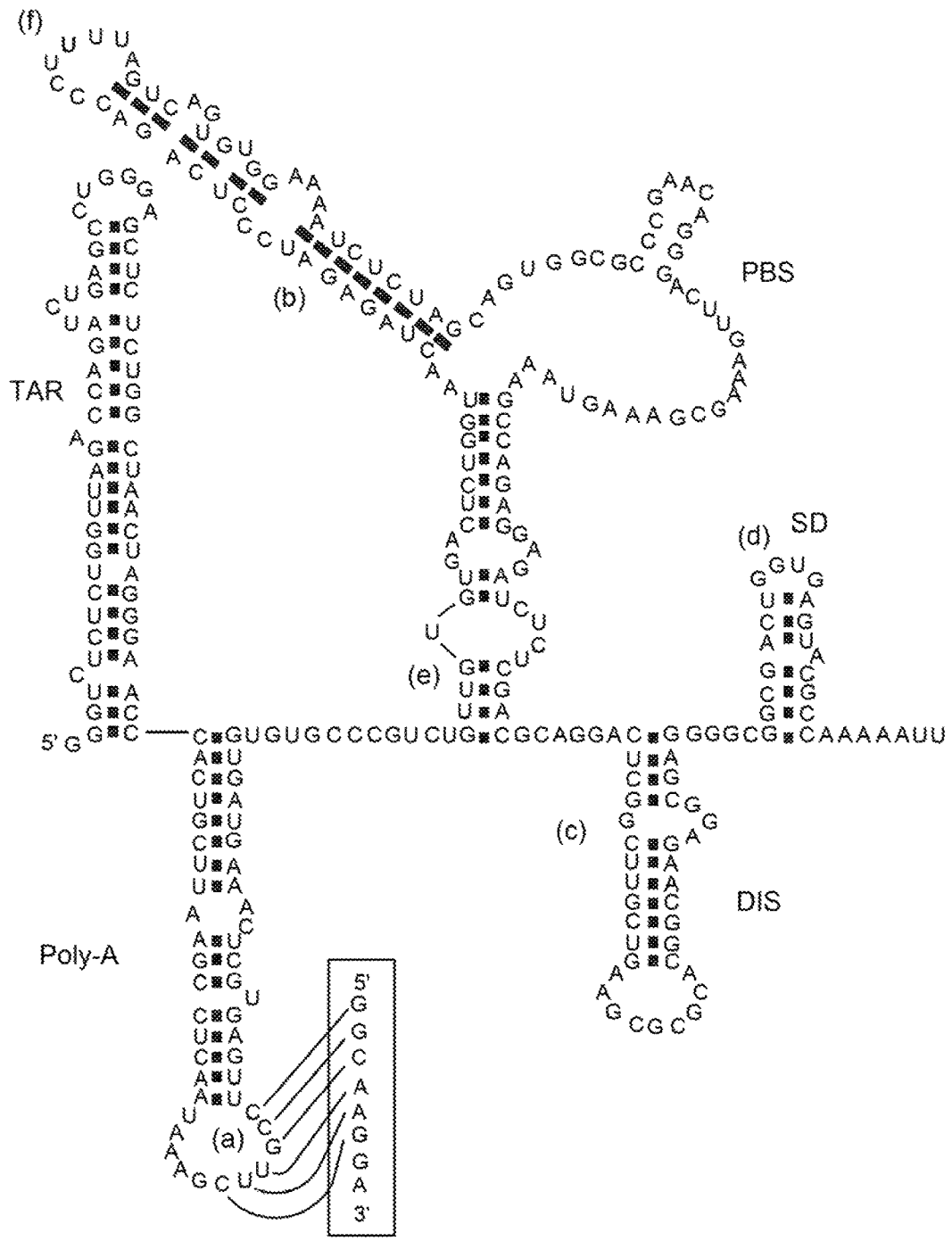

The results of this bioinformatics study for aptamers XIV22-23 (SEQ ID No: 29), XIV26-6 (SEQ ID No: 30) and XIV1-2 (SEQ ID No: 31), as well as with the RNA16(+) molecule (SEQ ID No: 39), are shown in FIG. 8. The results given by this analysis are the possible interactions between regions of both molecules (aptamer and UTR$_{308}$ target) and are represented as the total free energy of the bond between respective regions of the molecules involved. It is, therefore, a reciprocal study of which only the part that corresponds to the UTR$_{308}$ molecule (FIGS. 8A and 8B) is shown. The curves of this graph show the various valleys transposable to the sequence of the labeled target in the X axis. Those marked (a) to (f) correspond to interaction sites involving the motif 5'-GGCAAGGA-3' in the aptamers and the RNA16(+) molecule (SEQ ID No: 35). The curves for each molecule do not match globally because the sequence context in which the motif is located at each aptamer is different. All these regions of interaction can be identified in the eBMH-type folding of the UTR$_{308}$ molecule (SEQ ID No: 1) shown in FIG. 8C. A priori, the region (a) of interaction (located on the Poly-A domain) would be the most likely target for interaction and is proposed as having the primary responsibility for the binding with the motif 5'-GGCAAGGA-3' of the aptamer of the invention based on three criteria: i) the same valley (FIGS. 8A and 8B) coincides in the interaction of the UTR$_{308}$ (SEQ ID No: 1) with the four molecules [aptamers XIV22-23 (SEQ ID No: 29), XIV26-6 (SEQ ID No: 30), XIV1-2 (SEQ ID No: 31) and RNA16(+) (SEQ ID No: 35)]; ii) it has greater stability in the interaction as it has a lower total free energy of binding; and iii) 6 contiguous nucleotides in both molecules are involved in said interaction.

Additionally, both the binding and inhibition experiments that involved the RNA16(+) molecule (SEQ ID No: 35) required comparative analysis of a molecule useful as a negative control. As such negative control, it was necessary to use a molecule which, having also 16 nt in length and the same structure in dot-bracket notation ((((........)))) was the least favored for binding to the target molecule UTR$_{308}$ (SEQ ID No: 1). For this purpose, all molecules of sequence 5'-CCCCNNNNNNNNGGGG-3' were extensively folded in silico using the RNAfold program, and those generating the structure in dot-bracket notation ((((........)))) as most stable were selected. Thus, of the 65,536 initial sequences ($4^8$), it was found that 19,087 were folded preferably in the structure in dot-bracket notation ((((........)))). Next, by means of systematic comparison of sequences, it was evaluated which of them had fewer complementary nucleotides in the target molecule UTR$_{308}$ (SEQ ID No: 1), both in their single-stranded regions and in their double-stranded regions, in any of the two orientations and allowing G-C, A-U and G-U pairs. This resulted in a group of 112 sequences with the constraint that they would form a maximum of 5 base pairs between the molecule of 16 nt and the target, being consecutive a maximum of 4 of these base pairs. Using the program RNAup the interaction energy is calculated for all these molecules of 16 nt, taking into account the structure of the target. The results showed interaction free energies of between −0.40 and −7.20 kcal/mol. All in all, the molecule with sequence SEQ ID No: 45 (5'-CCCCGAAAACAAGGGG-3'), called "RNA16(−)", was chosen as a negative control. Its properties are as follows: i) it has the lowest (in absolute value) free energy of binding with the target (−0.40 kcal/mol) of all tested molecules; ii) the interaction with the target takes place in only one region; iii) such interaction involves only 2 base pairs: positions 22 and 23 of the target UTR$_{308}$ (SEQ ID No: 1) and positions 5-6 of the RNA16(−) molecule (SEQ ID No: 45).

Figure 9:

Example 5.—Binding Assays and Functional Inhibition Assays of the Replication of HIV-1 by the Aptamer of the Invention Inhibition of the replication of HIV-1 in cell cultures by different aptamers of the invention proved to be productive by means of the use of chimeric molecules consisting of the corresponding aptamer (XIV22-23—SEQ ID No: 29 or XIV26-6—SEQ ID No: 30) flanked by the 5' and 3' hairpins of the U6 small nuclear RNA (U6 snRNA). It has been reported that these hairpins confer greater stability to the RNA and provide it with a nuclear localization (Good et al., 1997). The HIV-1 inhibition assays and in vitro aptamer-UTR$_{308}$ binding assays were carried out with these chimeric molecules. A scheme of the structure of said molecules is shown in FIG. 9. The negative control for this inhibition consisted of the RNA molecule formed by these two hairpins without aptamer located therebetween. These new RNAs were called L-XIV22-23 (SEQ ID No: 37) and L-XIV26-6 (SEQ ID No: 38), and the negative control was called L-empty. The RNA16(+) (SEQ ID No: 35) and RNA16(−) (SEQ ID No: 45) molecules were used for both assays without modification or covalent binding to the hairpins.

The DNAs cloned in pGEM-T easy corresponding to aptamers XIV22-23 and XIV26-6 were used as a template for PCR with the primers 5'KpnIC3 (SEQ ID No: 46, 5'-CGACTCGGTACCGGGAATTCAA-3') and 3'ApaIC3 (SEQ ID No: 47, 5'-TCTGGGCCCGTCGAGCTCGTAG-TATC-3'). The amplification products consisted of DNAs containing the sequences of the selected RNA aptamers, flanked by the restriction targets KpnI and ApaI at their 5' and 3' ends, respectively. The cloning vector pU6 (Sanchez-Luque, F J. et al. 2010) and the amplification products were digested with the enzymes KpnI and ApaI. Both amplification products were cloned into the vector digested by means of ligation with T4 DNA ligase (Roche) and competent *Escherichia coli* bacteria of the strain DH5a were transformed with the ligation mixture for selection and conservation thereof.

For binding assays, all the molecules were transcribed in vitro as detailed in the section "process for obtaining aptamers", except for molecules RNA16(+) (SEQ ID No: 35) and RNA16(−) (SEQ ID No: 45), which were chemically synthesized (IBA GmbH). The template for the transcription of the aptamers was obtained by means of PCR amplification of the plasmid constructs containing the aptamer-hairpins conjugates of the U6 snRNA by means of oligonucleotides 5'T7U6 (SEQ ID No: 48: 5'-TAATACGACTCAC-TATAGGGGTCGTCGCTTCTGCACGACAT-3') and 3'ApaIU6 (SEQ ID No: 49: 5'-AGCGGGC-CCAAAAAGCGGACCGAAGTCCGC-3'). Furthermore, in this case, the UTR$_{308}$ molecule (SEQ ID No: 1) was not biotinylated. The aptamer molecules were dephosphorylated using calf intestinal alkaline phosphatase (CIAP, Roche) prior to labeling at 5' by phosphorylation by means of T4 polinucleotide kinase (T4PNK, New England Biolabs) and using $^{32}$PγATP as carbon source (Perkin Elmer). Molecules RNA16(+) (SEQ ID No: 35) and RNA16(−) (SEQ ID No: 45) were directly labeled at 5' since they were directly dephosphorylated after the chemical synthesis. All molecules were purified prior to use by means of acrylamide gel electrophoresis followed by phenol extraction and ethanol precipitation.

Traces of each aptamer were subjected to binding reactions at increasing amounts of UTR$_{308}$ molecule (SEQ ID No: 1). All molecules were denatured and renatured separately by means of incubation in 1×TMN at 65° C. for 10 minutes followed by incubation at 37° C. also for 10 minutes. Subsequently, aptamers and UTR$_{308}$ (SEQ ID No: 1) were mixed so that the final concentration of UTR$_{308}$ in each reaction was 0, 2, 20, 200 and 400 nM, respectively. Binding reactions were performed at 37° C. for 30 minutes and were stopped by adding a volume of 2× native load buffer (30% glycerol (v/v), 20% TMN 5× (v/v), 0'4% xylene-cyanol (w/v), 0'4% bromophenol (w/v) and 4% tRNA (w/v)) and incubation at 4° C. Reactions were resolved by electrophoresis in native gels of 6% polyacrylamide in 50 mM TRIS-acetic acid and 10 mM magnesium acetate as gel buffer and as electrophoresis buffer. Electrophoresis was performed at 4° C. and not more than 15 mA per gel. Gels were dried by a combination of vacuum and heat and incubated 10-16 hrs with radiation excitable screens (Storage phosphor screens, GE Healthcare). These screens were revealed in a scanner Typhoon 9400 (GE Healthcare).

The HIV-1 inhibition assays were carried out in cell cultures of the human embryonic kidney line 293T (HEK293T). Inhibition assays were performed simulating a post-integrative environment of the viral infection, that is, when the viral genome has been integrated into the cell genome as a proviral DNA. For this, cells were cotransfected with a plasmid DNA containing an integrated copy of the viral strain X4 NL4-3 and the corresponding inhibitory RNAs. RNAs were transcribed in vitro and directly purified by phenol extraction, and the DNA was purified from bacterial culture by means of Plasmid Mini Kt (Qiagen). 24-well culture plates were used and 24 hours before the transfection 250,000 cells were plated in 250 µl of DMEM with 10% fetal bovine serum (FBS) and 2 mM L-glutamine. For transfection, 1 µl of Lipofectamine 2000 reagent (Invitrogen) was diluted in 25 µl of Opti-MEM (PAA Laboratories GmbH) and incubated for 5 minutes at room temperature. At the same time, 500 ng of each inhibitory RNA and 100 ng of pNL4-3 were diluted in 25 µl Opti-MEM, mixed with the above and incubated at room temperature for 20 minutes. Next, 450 µl DMEM were added with 10% FBS and 2 mM L-glutamine and the medium of the culture well was replaced by this mixture. Viral activity in these cultures was measured after 48 hours by quantification of the amount of p24 viral antigen in the cell supernatant by enzyme immunoassay (Greenscreen HIV-1 Ag assay, BioRad).

Example 5.1: Binding of the Aptamer L-XIV22-23 (SEQ ID No: 37) to the Target Molecule UTR$_{308}$ (SEQ ID No: 1)

The binding assay of the aptamer L-XIV22-23 (SEQ ID No: 37) and the result of the quantification thereof are shown in FIG. 10. The binding curve of the aptamer to the target molecule UTR$_{308}$ fits a cooperative binding model with a single binding site. This curve follows the following equation:

$$Y = B_{max}X^h / (K_D^h + X^h),$$

wherein Y is the % of binding recorded; X is the concentration of UTR$_{308}$; Bmax is the predicted maximum binding according to the adjustment equation; $K_D$ is the dissociation constant, which is defined as the concentration of UTR$_{308}$ at which half maximum binding occurs (value of X for Y=B$_{max}$/2); and h is the Hill coefficient indicating the degree of cooperativity such that h<1 denotes negative cooperativity and h>1 positive cooperativity.

For the molecule L-XIV22-23 (SEQ ID No: 37) the expected maximal binding is B$_{max}$=87.59±1.26%; the dissociation constant is K$_D$=153.5±4.8 nM; and the Hill coefficient is h=2.60±0.86. The coefficient of adjustment to this graph is R$^2$=0.9987.

Example 5.2: Binding of the Aptamer L-XIV26-6 (SEQ ID No: 38) to the Target Molecule UTR$_{308}$ (SEQ ID No: 1)

The binding assay of the aptamer L-XIV26-6 (SEQ ID No: 38) and the result of the quantification thereof are shown in FIG. 11. The binding curve of the aptamer to the target molecule UTR$_{308}$ (SEQ ID No: 1) fits a hyperbolic binding model. This curve follows the following equation:

$$Y = B_{max}X / (K_D + X),$$

wherein is the % of binding recorded; X is the concentration of UTR$_{308}$; Bmax is the predicted maximum binding according to the adjustment equation; $K_D$ is the dissociation constant, which is defined as the concentration of UTR$_{308}$ at which half maximum binding occurs (X for Y=B$_{max}$/2).

For the molecule L-XIV26-6 (SEQ ID No: 38) the expected maximal binding is B$_{max}$≈100% and the dissociation constant is K$_D$=81.67±12.81 nM. The coefficient of adjustment to this graph is R$^2$=0.9912.

Example 5.3: Binding of the RNA16(+) Molecule (SEQ ID No: 35) to the Target Molecule UTR$_{308}$ (SEQ ID No: 1)

The binding assay of the RNA16(+) molecule (SEQ ID No: 35) and the result of the quantification thereof are shown in FIG. 12. The binding curve of the aptamer to the target molecule UTR$_{308}$ (SEQ ID No: 1) fits a hyperbolic binding model, with the same equation and parameters shown in Example 5.2.

For the RNA16(+) molecule (SEQ ID No: 35) the expected maximal binding is B$_{max}$≈79.35±8.20% and the dissociation constant is K$_D$=279.5±60.0 nM. The coefficient of adjustment to this graph is R$^2$=0.9908.

Example 5.4: Assay of Inhibition of the HIV-1 Replication Produced by Aptamer L-XIV22-23 (SEQ ID No: 37)

The molecule L-XIV22-23 (SEQ ID No: 37) achieves a post-integrative inhibition of HIV-1 replication in cell cultures of the HEK293T line of 76.77±7.48% compared to the control molecule L-empty. FIG. 13 shows the quantification of three independent experiments. The analysis by ANOVA statistical test shows that the inhibition is statistically significant with a p-value <0.01.

Example 5.5: Assay of Inhibition of the HIV-1 Replication Produced by Aptamer L-XIV26-6 (SEQ ID No.: 38)

The molecule L-XIV26-6 (SEQ ID No: 38) achieves a post-integrative inhibition of HIV-1 replication in cell cultures of the HEK293T line of 80.47±2.55% compared to the control molecule L-empty. FIG. 14 shows the quantification of three independent experiments. The analysis by ANOVA statistical test shows that the inhibition is statistically significant with a p-value <0.01.

Example 5.6: Inhibition of the HIV-1 Replication Produced by the RNA16(+) Molecule (SEQ ID No: 35)

The RNA16(+) molecule (SEQ ID No: 35) achieves a post-integrative inhibition of HIV-1 replication in cell cultures of the HEK293T line of 63.34±2.14% compared to the control molecule RNA16(-) (SEQ ID No: 45). FIG. 15 shows the quantification of three independent experiments. The analysis by ANOVA statistical test shows that the inhibition is statistically significant with a p-value <0.01.

REFERENCES

Briones C, Moreno M (2012). Applications of peptide nucleic acids (PNAs) and locked nucleic acids (LNAs) in biosensor development. Anal Bioanal Chem 402: 3071-3089.
Ducongé F, Toulmé J J (1999). In vitro selection identifies key determinants for loop-loop interactions: RNA aptamers selective for the TAR RNA element of HIV-1. RNA 5: 1605-1614.
Ellington A D, Szostak J W (1990). In vitro selection of RNA molecules that bind specific ligands. Nature 346: 818-822.
Geyer C R, Battersby T R, Benner S A (2003). Nucleobase pairing in Watson-Crick-like genetic expanded information systems. Structure 11: 1485-1498.
Good P D, Krikos A J, Li S X, et al. (1997). Expression of small, therapeutic RNAs in human cell nuclei. Gene Ther 4: 45-54.
Horvath S J, Firca J R, HunkapillerT, Hunkapiller M W, Hood L (1987). An automated DNA synthesizer employing deoxynucleoside 3'-phosphoramidites. Methods Enzymol. 1987; 154: 314-26.
Huthoff H, Berkhout B (2001). Two alternating structures of the HIV-1 leader RNA. RNA 7: 143-157.
Joyce G F (2004). Directed evolution of nucleic acid enzymes. Annu Rev Biochem 73: 791-836.
Kikuchi K, Umehara T, Fukuda K, Kuno A, Hasegawa T, Nishikawa S (2005). A hepatitis C virus (HCV) internal ribosome entry site (IRES) domain III-IV-targeted aptamer inhibits translation by binding to an apical loop of domain IIId. Nucleic Acids Res 33: 683-692.
Kolb G, Reigadas S, Castanotto D, et al. (2006). Endogenous expression of an anti-TAR aptamer reduces HIV-1 replication. RNA Biol 3: 150-156.
Klussmann S. (ed) (2006). The Aptamer Handbook. Wiley-VCH, Weinheim, Germany.
Kuiken C, Brian F, Leitner T, et al. (2011). HIV Sequence Compendium 2011. Los Alamos National Laboratory, Theoretical Biology and Biophysics, Los Alamos (NM), United States.
Lauridsen L H, Rothnagel J A, Veedu, R N (2012). Enzymatic Recognition of 2'-Modified Ribonucleoside 5'-Triphosphates: Towards the Evolution of Versatile Aptamers. Chem Bio Chem 13: 19-25.
Mathews D H, Sabina J, Zuker M, Turner H (1999). Expanded Sequence Dependence of Thermodynamic Parameters Provides Robust Prediction of RNA Secondary Structure. J Mol Biol 288: 911-940.
Pinheiro V B, Taylor A I, Cozens C, Abramov M, Renders M, Zhang S, Chaput J C, Wengel J, Peak-Chew S Y, McLaughlin S H, Herdewijn P, Holliger P (2012). Synthetic genetic polymers capable of heredity and evolution. Science 336: 341-344.
Romero-López C, Barroso-delJesus A, Puerta-Fernández E, Berzal-Herranz A (2005). Interfering with hepatitis C virus IRES activity using RNA molecules identified by a novel in vitro selection method. Biol Chem 386: 183-190.
Sánchez-Luque F J, Reyes-Darias J A, Puerta-Fernández E, Berzal-Herranz A (2010). Inhibition of HIV-1 replication and dimerization interference by dual inhibitory RNAs. Molecules 15: 4757-4772.
Tuerk C, Gold L. (1990). Systematic evolution of ligands by exponential enrichment: RNA ligands to bacteriophage T4 DNA polymerase. Science 249: 505-510.
Watrin M, Von Pelchrzim F, Dausse E, Schroeder R, Toulmé J J (2009). In vitro selection of RNA aptamers derived from a genomic human library against the TAR RNA element of HIV-1. Biochemistry 48: 6278-6284.

SEQUENCE LISTING

```
<160> NUMBER OF SEQ ID NOS: 56

<210> SEQ ID NO 1
<211> LENGTH: 308
<212> TYPE: RNA
<213> ORGANISM: Human immunodeficiency virus type 1
<220> FEATURE:
<221> NAME/KEY: source
<222> LOCATION: (1)..(308)
<223> OTHER INFORMATION: Nucleotides 1 to 308 "UTR308" from the genomic
      RNA of HIV-1 strain NL4-3 "HIV-1 vector pNL4-3"
<220> FEATURE:
<221> NAME/KEY: misc_feature
<222> LOCATION: (1)..(98)
<223> OTHER INFORMATION: /note="R region"
```

```
<220> FEATURE:
<221> NAME/KEY: misc_feature
<222> LOCATION: (1)..(58)
<223> OTHER INFORMATION: /note="TAR"
<220> FEATURE:
<221> NAME/KEY: misc_feature
<222> LOCATION: (59)..(105)
<223> OTHER INFORMATION: /note="Poly-A"
<220> FEATURE:
<221> NAME/KEY: misc_feature
<222> LOCATION: (81)..(86)
<223> OTHER INFORMATION: /note="RNA16(+) binding region"
<220> FEATURE:
<221> NAME/KEY: misc_feature
<222> LOCATION: (99)..(180)
<223> OTHER INFORMATION: /note="U5 region"
<220> FEATURE:
<221> NAME/KEY: misc_feature
<222> LOCATION: (117)..(237)
<223> OTHER INFORMATION: /note="PBS"
<220> FEATURE:
<221> NAME/KEY: misc_feature
<222> LOCATION: (244)..(278)
<223> OTHER INFORMATION: /note="DIS"
<220> FEATURE:
<221> NAME/KEY: misc_feature
<222> LOCATION: (283)..(301)
<223> OTHER INFORMATION: /note="SD"
<220> FEATURE:
<221> NAME/KEY: misc_feature
<222> LOCATION: (313)..(326)
<223> OTHER INFORMATION: /note="Psi"

<400> SEQUENCE: 1
gggucucucu gguuagacca gaucugagcc ugggagcucu cuggcuaacu agggaaccca      60
cugcuuaagc cucaauaaag cuugccuuga gugcucaaag uagugugugc ccgucuguug     120
ugugacucug guaacuagag aucccucaga cccuuuuagu caguguggaa aaucucuagc     180
aguggcgccc gaacagggac uugaaagcga aaguaaagcc agaggagauc ucucgacgca     240
ggacucggcu ugcugaagcg cgcacggcaa gaggcgaggg gcggcgacug gugaguacgc     300
caaaaauu                                                             308

<210> SEQ ID NO 2
<211> LENGTH: 336
<212> TYPE: RNA
<213> ORGANISM: Human immunodeficiency virus type 1
<220> FEATURE:
<221> NAME/KEY: source
<222> LOCATION: (1)..(336)
<223> OTHER INFORMATION: 5'UTR region from the genomic RNA of HIV-1
      strain NL4-3 "HIV-1 vector pNL4-3"
<220> FEATURE:
<221> NAME/KEY: misc_feature
<222> LOCATION: (1)..(98)
<223> OTHER INFORMATION: /note="R region"
<220> FEATURE:
<221> NAME/KEY: misc_feature
<222> LOCATION: (1)..(58)
<223> OTHER INFORMATION: /note="TAR"
<220> FEATURE:
<221> NAME/KEY: misc_feature
<222> LOCATION: (59)..(105)
<223> OTHER INFORMATION: /note="Poly-A"
<220> FEATURE:
<221> NAME/KEY: misc_feature
<222> LOCATION: (81)..(86)
<223> OTHER INFORMATION: /note="RNA16(+) binding region"
<220> FEATURE:
<221> NAME/KEY: misc_feature
<222> LOCATION: (99)..(180)
<223> OTHER INFORMATION: /note="U5 region"
<220> FEATURE:
<221> NAME/KEY: misc_feature
```

```
<222> LOCATION: (117)..(237)
<223> OTHER INFORMATION: /note="PBS"
<220> FEATURE:
<221> NAME/KEY: misc_feature
<222> LOCATION: (244)..(278)
<223> OTHER INFORMATION: /note="DIS"
<220> FEATURE:
<221> NAME/KEY: misc_feature
<222> LOCATION: (283)..(301)
<223> OTHER INFORMATION: /note="SD"
<220> FEATURE:
<221> NAME/KEY: misc_feature
<222> LOCATION: (313)..(326)
<223> OTHER INFORMATION: /note="Psi"

<400> SEQUENCE: 2
gggucucucu gguuagacca gaucugagcc ugggagcucu cuggcuaacu agggaaccca      60
cugcuuaagc cucaauaaag cuugccuuga gugcucaaag uagugugugc ccgucuguug     120
ugugacucug guaacuagag aucccucaga cccuuuuagu caguguggaa aaucucuagc     180
aguggcgccc gaacagggac uugaaagcga aguaaagcc agaggagauc ucucgacgca      240
ggacucggcu ugcugaagcg cgcacggcaa gaggcgaggg gcggcgacug ugaguacgc      300 caaaaauuuu gacuagcgga ggcuagaagg agagag                              336

<210> SEQ ID NO 3
<211> LENGTH: 290
<212> TYPE: RNA
<213> ORGANISM: Human immunodeficiency virus type 1
<220> FEATURE:
<221> NAME/KEY: source
<222> LOCATION: (1)..(290)
<223> OTHER INFORMATION: Common region in the 5'UTR from genomic and
      subgenomic RNA from HIV-1 strain NL4-3 "HIV-1 vector pNL4-3"
<220> FEATURE:
<221> NAME/KEY: misc_feature
<222> LOCATION: (1)..(98)
<223> OTHER INFORMATION: /note="R region"
<220> FEATURE:
<221> NAME/KEY: misc_feature
<222> LOCATION: (1)..(58)
<223> OTHER INFORMATION: /note="TAR"
<220> FEATURE:
<221> NAME/KEY: misc_feature
<222> LOCATION: (59)..(105)
<223> OTHER INFORMATION: /note="Poly-A"
<220> FEATURE:
<221> NAME/KEY: misc_feature
<222> LOCATION: (81)..(86)
<223> OTHER INFORMATION: /note="RNA16(+) binding region"
<220> FEATURE:
<221> NAME/KEY: misc_feature
<222> LOCATION: (99)..(180)
<223> OTHER INFORMATION: /note="U5 region"
<220> FEATURE:
<221> NAME/KEY: misc_feature
<222> LOCATION: (117)..(237)
<223> OTHER INFORMATION: /note="PBS"
<220> FEATURE:
<221> NAME/KEY: misc_feature
<222> LOCATION: (244)..(278)
<223> OTHER INFORMATION: /note="DIS"
<220> FEATURE:
<221> NAME/KEY: misc_feature
<222> LOCATION: (283)..(290)
<223> OTHER INFORMATION: /note="Nucleotides 1 to 8 of SD"

<400> SEQUENCE: 3
gggucucucu gguuagacca gaucugagcc ugggagcucu cuggcuaacu agggaaccca      60
cugcuuaagc cucaauaaag cuugccuuga gugcucaaag uagugugugc ccgucuguug     120
ugugacucug guaacuagag aucccucaga cccuuuuagu caguguggaa aaucucuagc     180
```
aguggcgccc gaacagggac uugaaagcga aaguaaagcc agaggagauc ucucgacgca    240
ggacucggcu ugcugaagcg cgcacggcaa gaggcgaggg gcggcgacug              290

<210> SEQ ID NO 4
<211> LENGTH: 25
<212> TYPE: RNA
<213> ORGANISM: Homo sapiens
<220> FEATURE:
<221> NAME/KEY: source
<222> LOCATION: (1)..(25)
<223> OTHER INFORMATION: 5' hairpin of snRNA U6

<400> SEQUENCE: 4
gucgucgcuu cugcacgaca uauac                                         25

<210> SEQ ID NO 5
<211> LENGTH: 24
<212> TYPE: RNA
<213> ORGANISM: Homo sapiens
<220> FEATURE:
<221> NAME/KEY: source
<222> LOCATION: (1)..(24)
<223> OTHER INFORMATION: 3' hairpin of snRNA U6

<400> SEQUENCE: 5
agagcggacu ucuguccgcu uuuu                                          24

<210> SEQ ID NO 6
<211> LENGTH: 16
<212> TYPE: DNA
<213> ORGANISM: Artificial Sequence
<220> FEATURE:
<223> OTHER INFORMATION: var-DNA consensus sequence
<220> FEATURE:
<221> NAME/KEY: source
<222> LOCATION: (1)..(16)
<223> OTHER INFORMATION: var-DNA consensus sequence
<220> FEATURE:
<221> NAME/KEY: misc_feature
<222> LOCATION: (1)..(1)
<223> OTHER INFORMATION: Nucleotide N is selected independently from A,
     C, G or T
<220> FEATURE:
<221> NAME/KEY: misc_feature
<222> LOCATION: (2)..(2)
<223> OTHER INFORMATION: Nucleotide N is selected independently from A,
     C, G or T
<220> FEATURE:
<221> NAME/KEY: misc_feature
<222> LOCATION: (3)..(3)
<223> OTHER INFORMATION: Nucleotide N is selected independently from A,
     C, G or T
<220> FEATURE:
<221> NAME/KEY: misc_feature
<222> LOCATION: (4)..(4)
<223> OTHER INFORMATION: Nucleotide N is selected independently from A,
     C, G or T
<220> FEATURE:
<221> NAME/KEY: misc_feature
<222> LOCATION: (9)..(9)
<223> OTHER INFORMATION: Nucleotide R is selected independently from A
     or G
<220> FEATURE:
<221> NAME/KEY: misc_feature
<222> LOCATION: (13)..(13)
<223> OTHER INFORMATION: Nucleotide N is complementary to nucleotide in
     position 4
<220> FEATURE:
<221> NAME/KEY: misc_feature
<222> LOCATION: (14)..(14)
<223> OTHER INFORMATION: Nucleotide N is complementary to nucleotide in
     position 3

```
<220> FEATURE:
<221> NAME/KEY: misc_feature
<222> LOCATION: (15)..(15)
<223> OTHER INFORMATION: Nucleotide N is complementary to nucleotide in
      position 2
<220> FEATURE:
<221> NAME/KEY: misc_feature
<222> LOCATION: (16)..(16)
<223> OTHER INFORMATION: Nucleotide N is complementary to nucleotide in
      position 1

<400> SEQUENCE: 6
nnnnggcarg gannnn                                                           16

<210> SEQ ID NO 7
<211> LENGTH: 16
<212> TYPE: RNA
<213> ORGANISM: Artificial Sequence
<220> FEATURE:
<223> OTHER INFORMATION: var-RNA consensus sequence
<220> FEATURE:
<221> NAME/KEY: source
<222> LOCATION: (1)..(16)
<223> OTHER INFORMATION: var-RNA consensus sequence
<220> FEATURE:
<221> NAME/KEY: misc_feature
<222> LOCATION: (1)..(1)
<223> OTHER INFORMATION: Nucleotide N is selected independently from A,
      C, G or U
<220> FEATURE:
<221> NAME/KEY: misc_feature
<222> LOCATION: (2)..(2)
<223> OTHER INFORMATION: Nucleotide N is selected independently from A,
      C, G or U
<220> FEATURE:
<221> NAME/KEY: misc_feature
<222> LOCATION: (3)..(3)
<223> OTHER INFORMATION: Nucleotide N is selected independently from A,
      C, G or U
<220> FEATURE:
<221> NAME/KEY: misc_feature
<222> LOCATION: (4)..(4)
<223> OTHER INFORMATION: Nucleotide N is selected independently from A,
      C, G or U
<220> FEATURE:
<221> NAME/KEY: misc_feature
<222> LOCATION: (9)..(9)
<223> OTHER INFORMATION: Nucleotide R is selected independently from A
      or G
<220> FEATURE:
<221> NAME/KEY: misc_feature
<222> LOCATION: (13)..(13)
<223> OTHER INFORMATION: Nucleotide N is complementary to nucleotide in
      position 4
<220> FEATURE:
<221> NAME/KEY: misc_feature
<222> LOCATION: (14)..(14)
<223> OTHER INFORMATION: Nucleotide N is complementary to nucleotide in
      position 3
<220> FEATURE:
<221> NAME/KEY: misc_feature
<222> LOCATION: (15)..(15)
<223> OTHER INFORMATION: Nucleotide N is complementary to nucleotide in
      position 2
<220> FEATURE:
<221> NAME/KEY: misc_feature
<222> LOCATION: (16)..(16)
<223> OTHER INFORMATION: Nucleotide N is complementary to nucleotide in
      position 1

<400> SEQUENCE: 7
nnnnggcarg gannnn                                                           16

<210> SEQ ID NO 8
<211> LENGTH: 16
```

```
<212> TYPE: DNA
<213> ORGANISM: Artificial Sequence
<220> FEATURE:
<223> OTHER INFORMATION: var-DNA preferred consensus sequence
<220> FEATURE:
<221> NAME/KEY: source
<222> LOCATION: (1)..(16)
<223> OTHER INFORMATION: var-DNA preferred consensus sequence
<220> FEATURE:
<221> NAME/KEY: misc_feature
<222> LOCATION: (1)..(1)
<223> OTHER INFORMATION: Nucleotide N is selected independently from A,
      C, G or T
<220> FEATURE:
<221> NAME/KEY: misc_feature
<222> LOCATION: (2)..(2)
<223> OTHER INFORMATION: Nucleotide N is selected independently from A,
      C, G or T
<220> FEATURE:
<221> NAME/KEY: misc_feature
<222> LOCATION: (3)..(3)
<223> OTHER INFORMATION: Nucleotide D is selected independently from A,
      G or T
<220> FEATURE:
<221> NAME/KEY: misc_feature
<222> LOCATION: (4)..(4)
<223> OTHER INFORMATION: Nucleotide Y is selected independently from T
      or C
<220> FEATURE:
<221> NAME/KEY: misc_feature
<222> LOCATION: (9)..(9)
<223> OTHER INFORMATION: Nucleotide R is selected independently from A
      or G
<220> FEATURE:
<221> NAME/KEY: misc_feature
<222> LOCATION: (13)..(13)
<223> OTHER INFORMATION: Nucleotide R is A when Y is T, or  is G when Y
      is C
<220> FEATURE:
<221> NAME/KEY: misc_feature
<222> LOCATION: (14)..(14)
<223> OTHER INFORMATION: Nucleotide N is T when D is A, or  is C when D
      is G, or  is A
      when D is T
<220> FEATURE:
<221> NAME/KEY: misc_feature
<222> LOCATION: (15)..(15)
<223> OTHER INFORMATION: Nucleotide N is A when N in position 2 is T, or
      is C when N in position 2 is G, or  is G when N in position 2 is
      C, or  is T when N in position 2 is A
<220> FEATURE:
<221> NAME/KEY: misc_feature
<222> LOCATION: (16)..(16)
<223> OTHER INFORMATION: Nucleotide N is A when N in position 1 is T, or
      is C when N in position 1 is G, or is G when N in position 1 is C,
      or is T when N in position 1 is A

<400> SEQUENCE: 8
nndyggcarg garnnn                                                          16

<210> SEQ ID NO 9
<211> LENGTH: 16
<212> TYPE: RNA
<213> ORGANISM: Artificial Sequence
<220> FEATURE:
<223> OTHER INFORMATION: var-RNA preferred consensus sequence
<220> FEATURE:
<221> NAME/KEY: source
<222> LOCATION: (1)..(16)
<223> OTHER INFORMATION: var-RNA preferred consensus sequence
<220> FEATURE:
<221> NAME/KEY: misc_feature
<222> LOCATION: (1)..(1)
<223> OTHER INFORMATION: Nucleotide N is selected independently from A,
      C, G or U
<220> FEATURE:
<221> NAME/KEY: misc_feature
```

```
<222> LOCATION: (2)..(2)
<223> OTHER INFORMATION: Nucleotide N is selected independently from A,
      C, G or U
<220> FEATURE:
<221> NAME/KEY: misc_feature
<222> LOCATION: (3)..(3)
<223> OTHER INFORMATION: Nucleotide D is selected independently from A,
      G or U
<220> FEATURE:
<221> NAME/KEY: misc_feature
<222> LOCATION: (4)..(4)
<223> OTHER INFORMATION: Nucleotide Y is selected independently from U
      or C
<220> FEATURE:
<221> NAME/KEY: misc_feature
<222> LOCATION: (9)..(9)
<223> OTHER INFORMATION: Nucleotide R is selected independently from A
      or G
<220> FEATURE:
<221> NAME/KEY: misc_feature
<222> LOCATION: (13)..(13)
<223> OTHER INFORMATION: Nucleotide R is selected from A or G when Y is
      U, or is G when Y is C
<220> FEATURE:
<221> NAME/KEY: misc_feature
<222> LOCATION: (14)..(14)
<223> OTHER INFORMATION: Nucleotide N is U when D is A, or is selected
      from C or U when D is G, or is selected from A or G when D is U
<220> FEATURE:
<221> NAME/KEY: misc_feature
<222> LOCATION: (15)..(15)
<223> OTHER INFORMATION: Nucleotide N is selected from A or G when N in
      position 2 is U, or is selected from C or U when N in position 2
      is G, or is G when N in position 2 is C, or is U when N in
      position 2 is A or G
<220> FEATURE:
<221> NAME/KEY: misc_feature
<222> LOCATION: (16)..(16)
<223> OTHER INFORMATION: Nucleotide N is selected from A or G when N in
      position 1 is U, or isselected from C or U when N in position 1 is
      G, or is G when N in position 1 is C, or is U when N in position 1
      is A or G

<400> SEQUENCE: 9
nndyggcarg garnnn                                                        16

<210> SEQ ID NO 10
<211> LENGTH: 64
<212> TYPE: RNA
<213> ORGANISM: Artificial Sequence
<220> FEATURE:
<223> OTHER INFORMATION: Aptamer IX03-1
<220> FEATURE:
<221> NAME/KEY: source
<222> LOCATION: (1)..(64)
<223> OTHER INFORMATION: IX03-1
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"

<400> SEQUENCE: 10
gggaauucaa gacacgaaca uaguggcaag gaacuaugga gugaucugau acuacgagcu         60
cgac                                                                     64

<210> SEQ ID NO 11
```

```
<211> LENGTH: 64
<212> TYPE: RNA
<213> ORGANISM: Artificial Sequence
<220> FEATURE:
<223> OTHER INFORMATION: Aptamer IX24-1
<220> FEATURE:
<221> NAME/KEY: source
<222> LOCATION: (1)..(64)
<223> OTHER INFORMATION: IX24-1
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"

<400> SEQUENCE: 11
gggaauucaa cgacaggcuc cauguggcaa ggaaaaugga gugaucugau acuacgagcu      60
cgac                                                                  64

<210> SEQ ID NO 12
<211> LENGTH: 64
<212> TYPE: RNA
<213> ORGANISM: Artificial Sequence
<220> FEATURE:
<223> OTHER INFORMATION: Aptamer IX36-1
<220> FEATURE:
<221> NAME/KEY: source
<222> LOCATION: (1)..(64)
<223> OTHER INFORMATION: IX36-1
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"

<400> SEQUENCE: 12
gggaauucaa caccacuauu guuggcaagg aagcaaugga gugaucugau acuacgagcu      60
cgac                                                                  64

<210> SEQ ID NO 13
<211> LENGTH: 64
<212> TYPE: RNA
<213> ORGANISM: Artificial Sequence
<220> FEATURE:
<223> OTHER INFORMATION: Aptamer X02-1
<220> FEATURE:
<221> NAME/KEY: source
<222> LOCATION: (1)..(64)
<223> OTHER INFORMATION: X02-1
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
<223> OTHER INFORMATION: /note="Selected regiOn"
<220> FEATURE:
<221> NAME/KEY: misc_feature
```

<222> LOCATION: (36)..(64)
<223> OTHER INFORMATION: /note="3' constant region"

<400> SEQUENCE: 13
gggaauucaa cuucaagcag uggcaaggaa cugcaaugga gugaucugau acuacgagcu    60
cgac    64

<210> SEQ ID NO 14
<211> LENGTH: 64
<212> TYPE: RNA
<213> ORGANISM: Artificial Sequence
<220> FEATURE:
<223> OTHER INFORMATION: Aptamer X04-2
<220> FEATURE:
<221> NAME/KEY: source
<222> LOCATION: (1)..(64)
<223> OTHER INFORMATION: X04-2
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"

<400> SEQUENCE: 14
gggaauucaa guacggcaag gaguacaucg uaguaaugga gugaucugau acuacgagcu    60
cgac    64

<210> SEQ ID NO 15
<211> LENGTH: 64
<212> TYPE: RNA
<213> ORGANISM: Artificial Sequence
<220> FEATURE:
<223> OTHER INFORMATION: Aptamer X09-1
<220> FEATURE:
<221> NAME/KEY: source
<222> LOCATION: (1)..(64)
<223> OTHER INFORMATION: X09-1
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"

<400> SEQUENCE: 15
gggaauucaa guacggcaag gaguacaucg uaggaaugga gugaucugau acuacgagcu    60
cgac    64

<210> SEQ ID NO 16
<211> LENGTH: 64
<212> TYPE: RNA
<213> ORGANISM: Artificial Sequence
<220> FEATURE:
<223> OTHER INFORMATION: Aptamer X10-7
<220> FEATURE:
<221> NAME/KEY: source
<222> LOCATION: (1)..(64)

```
<223> OTHER INFORMATION: X10-7
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"

<400> SEQUENCE: 16
gggaauucaa caccacuauu guuggcaagg aagcaaugga gugaucugau acuacgagcu    60
cgac                                                                 64

<210> SEQ ID NO 17
<211> LENGTH: 64
<212> TYPE: RNA
<213> ORGANISM: Artificial Sequence
<220> FEATURE:
<223> OTHER INFORMATION: Aptamer X13-1
<220> FEATURE:
<221> NAME/KEY: source
<222> LOCATION: (1)..(64)
<223> OTHER INFORMATION: X13-1
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"

<400> SEQUENCE: 17
gggaauucaa guacggcaag gaguacaucg uagcaaugga gugaucugau acuacgagcu    60
cgac                                                                 64

<210> SEQ ID NO 18
<211> LENGTH: 64
<212> TYPE: RNA
<213> ORGANISM: Artificial Sequence
<220> FEATURE:
<223> OTHER INFORMATION: Aptamer X36-1
<220> FEATURE:
<221> NAME/KEY: source
<222> LOCATION: (1)..(64)
<223> OTHER INFORMATION: X36-1
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"

<400> SEQUENCE: 18
gggaauucaa gacauauacca uuguggcaag gaacaaugga gugaucugau acuacgagcu   60
cgac                                                                 64
```

```
<210> SEQ ID NO 19
<211> LENGTH: 64
<212> TYPE: RNA
<213> ORGANISM: Artificial Sequence
<220> FEATURE:
<223> OTHER INFORMATION: Aptamer X41-2
<220> FEATURE:
<221> NAME/KEY: source
<222> LOCATION: (1)..(64)
<223> OTHER INFORMATION: X41-2
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"

<400> SEQUENCE: 19
gggaauucaa gcauacugca ucguggcaag gaacgaugga gugaucugau acuacgagcu      60
cgac                                                                  64

<210> SEQ ID NO 20
<211> LENGTH: 64
<212> TYPE: RNA
<213> ORGANISM: Artificial Sequence
<220> FEATURE:
<223> OTHER INFORMATION: Aptamer XI1-17
<220> FEATURE:
<221> NAME/KEY: source
<222> LOCATION: (1)..(64)
<223> OTHER INFORMATION: XI1-17
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"

<400> SEQUENCE: 20
gggaauucaa caccacuauu guuggcaagg aagcaaugga gugaucugau acuacgagcu      60
cgac                                                                  64

<210> SEQ ID NO 21
<211> LENGTH: 64
<212> TYPE: RNA
<213> ORGANISM: Artificial Sequence
<220> FEATURE:
<223> OTHER INFORMATION: Aptamer XI21-7
<220> FEATURE:
<221> NAME/KEY: source
<222> LOCATION: (1)..(64)
<223> OTHER INFORMATION: XI21-7
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
```

<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"

<400> SEQUENCE: 21
gggaauucaa guacggcaag gaguacaucg uagcaaugga gugaucugau acuacgagcu    60
cgac    64

<210> SEQ ID NO 22
<211> LENGTH: 64
<212> TYPE: RNA
<213> ORGANISM: Artificial Sequence
<220> FEATURE:
<223> OTHER INFORMATION: Aptamer XI23-3
<220> FEATURE:
<221> NAME/KEY: source
<222> LOCATION: (1)..(64)
<223> OTHER INFORMATION: XI23-3
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"

<400> SEQUENCE: 22
gggaauucaa guacggcaag gaguacaucg uaguaaugga gugaucugau acuacgagcu    60
cgac    64

<210> SEQ ID NO 23
<211> LENGTH: 64
<212> TYPE: RNA
<213> ORGANISM: Artificial Sequence
<220> FEATURE:
<223> OTHER INFORMATION: Aptamer XI141-2
<220> FEATURE:
<221> NAME/KEY: source
<222> LOCATION: (1)..(64)
<223> OTHER INFORMATION: XI141-2
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"

<400> SEQUENCE: 23
gggaauucaa cacaaccugg guggcaagga acccaaugga gugaucugau acuacgagcu    60
cgac    64

<210> SEQ ID NO 24
<211> LENGTH: 64
<212> TYPE: RNA
<213> ORGANISM: Artificial Sequence
<220> FEATURE:
<223> OTHER INFORMATION: Aptamer XI13-1

```
<220> FEATURE:
<221> NAME/KEY: source
<222> LOCATION: (1)..(64)
<223> OTHER INFORMATION: XI13-1
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"

<400> SEQUENCE: 24
gggaauucaa gaauagcaca uuguggcaag gaacaaugga gugaucugau acuacgagcu      60
cgac                                                                  64

<210> SEQ ID NO 25
<211> LENGTH: 64
<212> TYPE: RNA
<213> ORGANISM: Artificial Sequence
<220> FEATURE:
<223> OTHER INFORMATION: Aptamer XI101-1
<220> FEATURE:
<221> NAME/KEY: source
<222> LOCATION: (1)..(64)
<223> OTHER INFORMATION: XI101-1
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"

<400> SEQUENCE: 25
gggaauucaa cacuaccugg guggcaagga acccaaugga gugaucugau acuacgagcu      60
cgac                                                                  64

<210> SEQ ID NO 26
<211> LENGTH: 64
<212> TYPE: RNA
<213> ORGANISM: Artificial Sequence
<220> FEATURE:
<223> OTHER INFORMATION: Aptamer XI149-1
<220> FEATURE:
<221> NAME/KEY: source
<222> LOCATION: (1)..(64)
<223> OTHER INFORMATION: XI149-1
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"

<400> SEQUENCE: 26
```

```
gggaauucaa caccacuauu guuggcaagg aaacaaugga gugaucugau acuacgagcu    60
cgac                                                                64
```

```
<210> SEQ ID NO 27
<211> LENGTH: 64
<212> TYPE: RNA
<213> ORGANISM: Artificial Sequence
<220> FEATURE:
<223> OTHER INFORMATION: Aptamer XI107-1
<220> FEATURE:
<221> NAME/KEY: source
<222> LOCATION: (1)..(64)
<223> OTHER INFORMATION: XI107-1
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"

<400> SEQUENCE: 27
gggaauucaa guacggcaag gaguacaucg uaacaaugga gugaucugau acuacgagcu    60
cgac                                                                64
```

```
<210> SEQ ID NO 28
<211> LENGTH: 64
<212> TYPE: RNA
<213> ORGANISM: Artificial Sequence
<220> FEATURE:
<223> OTHER INFORMATION: Aptamer XI129-1
<220> FEATURE:
<221> NAME/KEY: source
<222> LOCATION: (1)..(64)
<223> OTHER INFORMATION: XI129-1
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"

<400> SEQUENCE: 28
gggaauucaa caccacuauu guuggcaagg aaguaaugga gugaucugau acuacgagcu    60
cgac                                                                64
```

```
<210> SEQ ID NO 29
<211> LENGTH: 64
<212> TYPE: RNA
<213> ORGANISM: Artificial Sequence
<220> FEATURE:
<223> OTHER INFORMATION: Aptamer XIV22-23
<220> FEATURE:
<221> NAME/KEY: source
<222> LOCATION: (1)..(64)
<223> OTHER INFORMATION: XIV22-23
<220> FEATURE:
<221> NAME/KEY: misc_feature
<222> LOCATION: (1)..(10)
<223> OTHER INFORMATION: /note="5' constant region"
```

```
<220> FEATURE:
<221> NAME/KEY: misc_feature
<222> LOCATION: (11)..(35)
<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"

<400> SEQUENCE: 29
gggaauucaa caccacuauu guuggcaagg aagcaaugga gugaucugau acuacgagcu    60
cgac                                                                64

<210> SEQ ID NO 30
<211> LENGTH: 64
<212> TYPE: RNA
<213> ORGANISM: Artificial Sequence
<220> FEATURE:
<223> OTHER INFORMATION: Aptamer XIV26-6
<220> FEATURE:
<221> NAME/KEY: source
<222> LOCATION: (1)..(64)
<223> OTHER INFORMATION: XIV26-6
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"

<400> SEQUENCE: 30
gggaauucaa guacggcaag gaguacaucg uagcaaugga gugaucugau acuacgagcu    60
cgac                                                                64

<210> SEQ ID NO 31
<211> LENGTH: 64
<212> TYPE: RNA
<213> ORGANISM: Artificial Sequence
<220> FEATURE:
<223> OTHER INFORMATION: Aptamer XIV1-2
<220> FEATURE:
<221> NAME/KEY: source
<222> LOCATION: (1)..(64)
<223> OTHER INFORMATION: XIV1-2
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"

<400> SEQUENCE: 31
gggaauucaa cacaaccugg guggcaagga acccaaugga gugaucugau acuacgagcu    60
cgac                                                                64

<210> SEQ ID NO 32
<211> LENGTH: 64
<212> TYPE: RNA
```

```
<213> ORGANISM: Artificial Sequence
<220> FEATURE:
<223> OTHER INFORMATION: Aptamer XIV32-1
<220> FEATURE:
<221> NAME/KEY: source
<222> LOCATION: (1)..(64)
<223> OTHER INFORMATION: XIV32-1
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"

<400> SEQUENCE: 32
gggaauucaa caccacuauu guuggcaggg aagcaaugga gugaucugau acuacgagcu    60
cgac                                                                64

<210> SEQ ID NO 33
<211> LENGTH: 64
<212> TYPE: RNA
<213> ORGANISM: Artificial Sequence
<220> FEATURE:
<223> OTHER INFORMATION: Aptamer XIV5-1
<220> FEATURE:
<221> NAME/KEY: source
<222> LOCATION: (1)..(64)
<223> OTHER INFORMATION: XIV5-1
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"

<400> SEQUENCE: 33
gggaauucaa guacggcaag gaguacaucg cagcaaugga gugaucugau acuacgagcu    60
cgac                                                                64

<210> SEQ ID NO 34
<211> LENGTH: 64
<212> TYPE: RNA
<213> ORGANISM: Artificial Sequence
<220> FEATURE:
<223> OTHER INFORMATION: Aptamer XIV12-1
<220> FEATURE:
<221> NAME/KEY: source
<222> LOCATION: (1)..(64)
<223> OTHER INFORMATION: XIV12-1
<220> FEATURE:
<221> NAME/KEY: misc_feature
<222> LOCATION: (1)..(10)
<223> OTHER INFORMATION: /note="5' constant region"
<220> FEATURE:
<221> NAME/KEY: misc_feature
<222> LOCATION: (11)..(35)
<223> OTHER INFORMATION: /note="Selected region"
<220> FEATURE:
<221> NAME/KEY: misc_feature
<222> LOCATION: (36)..(64)
<223> OTHER INFORMATION: /note="3' constant region"
```

```
<400> SEQUENCE: 34
gggaauucaa caccgcuauu guuggcaagg aagcaaugga gugaucugau acuacgagcu    60
cgac                                                                64

<210> SEQ ID NO 35
<211> LENGTH: 16
<212> TYPE: RNA
<213> ORGANISM: Artificial Sequence
<220> FEATURE:
<223> OTHER INFORMATION: RNA16(+)
<220> FEATURE:
<221> NAME/KEY: source
<222> LOCATION: (1)..(16)
<223> OTHER INFORMATION: RNA16(+)
<220> FEATURE:
<221> NAME/KEY: misc_feature
<222> LOCATION: (5)..(12)
<223> OTHER INFORMATION: /note="Apical loop"

<400> SEQUENCE: 35
ccccggcaag gagggg                                                   16

<210> SEQ ID NO 36
<211> LENGTH: 16
<212> TYPE: RNA
<213> ORGANISM: Artificial Sequence
<220> FEATURE:
<223> OTHER INFORMATION: RNA16(+) var-G
<220> FEATURE:
<221> NAME/KEY: source
<222> LOCATION: (1)..(16)
<223> OTHER INFORMATION: RNA16(+) var-G
<220> FEATURE:
<221> NAME/KEY: misc_feature
<222> LOCATION: (5)..(12)
<223> OTHER INFORMATION: /note="Apical loop var-G"

<400> SEQUENCE: 36
ccccggcagg gagggg                                                   16

<210> SEQ ID NO 37
<211> LENGTH: 125
<212> TYPE: RNA
<213> ORGANISM: Artificial Sequence
<220> FEATURE:
<223> OTHER INFORMATION: L-XIV22-23
<220> FEATURE:
<221> NAME/KEY: source
<222> LOCATION: (1)..(125)
<223> OTHER INFORMATION: L-XIV22-23
<220> FEATURE:
<221> NAME/KEY: misc_feature
<222> LOCATION: (1)..(25)
<223> OTHER INFORMATION: /note="5' hairpin of snRNA U6"
<220> FEATURE:
<221> NAME/KEY: misc_feature
<222> LOCATION: (32)..(95)
<223> OTHER INFORMATION: /note="XIV22-23"
<220> FEATURE:
<221> NAME/KEY: misc_feature
<222> LOCATION: (102)..(125)
<223> OTHER INFORMATION: /note="3' hairpin of snRNA U6"

<400> SEQUENCE: 37
gucgucgcuu cugcacgaca uauacgguac cgggaauuca acaccacuau uguuggcaag    60
gaagcaaugg agugaucuga uacuacgagc ucgacgggcc cagagcggac uucuguccgc   120
uuuuu                                                              125
```

```
<210> SEQ ID NO 38
<211> LENGTH: 125
<212> TYPE: RNA
<213> ORGANISM: Artificial Sequence
<220> FEATURE:
<223> OTHER INFORMATION: L-XIV26-6
<220> FEATURE:
<221> NAME/KEY: source
<222> LOCATION: (1)..(125)
<223> OTHER INFORMATION: L-XIV26-6
<220> FEATURE:
<221> NAME/KEY: misc_feature
<222> LOCATION: (1)..(25)
<223> OTHER INFORMATION: /note="5' hairpin of snRNA U6"
<220> FEATURE:
<221> NAME/KEY: misc_feature
<222> LOCATION: (32)..(95)
<223> OTHER INFORMATION: /note="XIV26-6"
<220> FEATURE:
<221> NAME/KEY: misc_feature
<222> LOCATION: (102)..(125)
<223> OTHER INFORMATION: /note="3' hairpin of snRNA U6"

<400> SEQUENCE: 38
gucgucgcuu cugcacgaca uauacgguac cgggaauuca aguacggcaa ggaguacauc    60
guagcaaugg agugaucuga uacuacgagc ucgacgggcc cagagcggac uucuguccgc   120
uuuuu                                                                125

<210> SEQ ID NO 39
<211> LENGTH: 16
<212> TYPE: RNA
<213> ORGANISM: Artificial Sequence
<220> FEATURE:
<223> OTHER INFORMATION: generic RNA16(+)
<220> FEATURE:
<221> NAME/KEY: source
<222> LOCATION: (1)..(16)
<223> OTHER INFORMATION: generic RNA16(+)
<220> FEATURE:
<221> NAME/KEY: misc_feature
<222> LOCATION: (5)..(12)
<223> OTHER INFORMATION: /note="Generic apical loop"
<220> FEATURE:
<221> NAME/KEY: misc_feature
<222> LOCATION: (9)..(9)
<223> OTHER INFORMATION: /note="Nucleotide R, selected from A or G"

<400> SEQUENCE: 39
ccccggcarg gagggg                                                     16

<210> SEQ ID NO 40
<211> LENGTH: 30
<212> TYPE: DNA
<213> ORGANISM: Artificial Sequence
<220> FEATURE:
<223> OTHER INFORMATION: 5'EcoRIK primer
<220> FEATURE:
<221> NAME/KEY: source
<222> LOCATION: (1)..(30)
<223> OTHER INFORMATION: 5'EcoRIK
<220> FEATURE:
<221> NAME/KEY: misc_feature
<222> LOCATION: (4)..(23)
<223> OTHER INFORMATION: /note="T7 RNA polymerase promoter"
<220> FEATURE:
<221> NAME/KEY: misc_feature
<222> LOCATION: (23)..(28)
<223> OTHER INFORMATION: /note="EcoRI restriction enzyme sequence
      recognition"

<400> SEQUENCE: 40
```
ggataatacg actcactata gggaattcaa                                    30

<210> SEQ ID NO 41
<211> LENGTH: 71
<212> TYPE: DNA
<213> ORGANISM: Artificial Sequence
<220> FEATURE:
<223> OTHER INFORMATION: 3'RANDOMK
<220> FEATURE:
<221> NAME/KEY: source
<222> LOCATION: (1)..(71)
<223> OTHER INFORMATION: 3'RANDOMK
<220> FEATURE:
<221> NAME/KEY: misc_feature
<222> LOCATION: (4)..(9)
<223> OTHER INFORMATION: /note="XhoI restriction enzyme sequence
      recognition"
<220> FEATURE:
<221> NAME/KEY: misc_feature
<222> LOCATION: (30)..(54)
<223> OTHER INFORMATION: /note="random sequence region"
<220> FEATURE:
<221> NAME/KEY: misc_feature
<222> LOCATION: (30)..(30)
<223> OTHER INFORMATION: Nucleotide N is selected independently from A,
      C, G or T
<220> FEATURE:
<221> NAME/KEY: misc_feature
<222> LOCATION: (31)..(31)
<223> OTHER INFORMATION: Nucleotide N is selected independently from A,
      C, G or T
<220> FEATURE:
<221> NAME/KEY: misc_feature
<222> LOCATION: (32)..(32)
<223> OTHER INFORMATION: Nucleotide N is selected independently from A,
      C, G or T
<220> FEATURE:
<221> NAME/KEY: misc_feature
<222> LOCATION: (33)..(33)
<223> OTHER INFORMATION: Nucleotide N is selected independently from A,
      C, G or T
<220> FEATURE:
<221> NAME/KEY: misc_feature
<222> LOCATION: (34)..(34)
<223> OTHER INFORMATION: Nucleotide N is selected independently from A,
      C, G or T
<220> FEATURE:
<221> NAME/KEY: misc_feature
<222> LOCATION: (35)..(35)
<223> OTHER INFORMATION: Nucleotide N is selected independently from A,
      C, G or T
<220> FEATURE:
<221> NAME/KEY: misc_feature
<222> LOCATION: (36)..(36)
<223> OTHER INFORMATION: Nucleotide N is selected independently from A,
      C, G or T
<220> FEATURE:
<221> NAME/KEY: misc_feature
<222> LOCATION: (37)..(37)
<223> OTHER INFORMATION: Nucleotide N is selected independently from A,
      C, G or T
<220> FEATURE:
<221> NAME/KEY: misc_feature
<222> LOCATION: (38)..(38)
<223> OTHER INFORMATION: Nucleotide N is selected independently from A,
      C, G or T
<220> FEATURE:
<221> NAME/KEY: misc_feature
<222> LOCATION: (39)..(39)
<223> OTHER INFORMATION: Nucleotide N is selected independently from A,
      C, G or T
<220> FEATURE:
<221> NAME/KEY: misc_feature
<222> LOCATION: (40)..(40)
<223> OTHER INFORMATION: Nucleotide N is selected independently from A,
      C, G or T
<220> FEATURE:
<221> NAME/KEY: misc_feature

```
<222> LOCATION: (41)..(41)
<223> OTHER INFORMATION: Nucleotide N is selected independently from A,
      C, G or T
<220> FEATURE:
<221> NAME/KEY: misc_feature
<222> LOCATION: (42)..(42)
<223> OTHER INFORMATION: Nucleotide N is selected independently from A,
      C, G or T
<220> FEATURE:
<221> NAME/KEY: misc_feature
<222> LOCATION: (43)..(43)
<223> OTHER INFORMATION: Nucleotide N is selected independently from A,
      C, G or T
<220> FEATURE:
<221> NAME/KEY: misc_feature
<222> LOCATION: (44)..(44)
<223> OTHER INFORMATION: Nucleotide N is selected independently from A,
      C, G or T
<220> FEATURE:
<221> NAME/KEY: misc_feature
<222> LOCATION: (45)..(45)
<223> OTHER INFORMATION: Nucleotide N is selected independently from A,
      C, G or T
<220> FEATURE:
<221> NAME/KEY: misc_feature
<222> LOCATION: (46)..(46)
<223> OTHER INFORMATION: Nucleotide N is selected independently from A,
      C, G or T
<220> FEATURE:
<221> NAME/KEY: misc_feature
<222> LOCATION: (47)..(47)
<223> OTHER INFORMATION: Nucleotide N is selected independently from A,
      C, G or T
<220> FEATURE:
<221> NAME/KEY: misc_feature
<222> LOCATION: (48)..(48)
<223> OTHER INFORMATION: Nucleotide N is selected independently from A,
      C, G or T
<220> FEATURE:
<221> NAME/KEY: misc_feature
<222> LOCATION: (49)..(49)
<223> OTHER INFORMATION: Nucleotide N is selected independently from A,
      C, G or T
<220> FEATURE:
<221> NAME/KEY: misc_feature
<222> LOCATION: (50)..(50)
<223> OTHER INFORMATION: Nucleotide N is selected independently from A,
      C, G or T
<220> FEATURE:
<221> NAME/KEY: misc_feature
<222> LOCATION: (51)..(51)
<223> OTHER INFORMATION: Nucleotide N is selected independently from A,
      C, G or T
<220> FEATURE:
<221> NAME/KEY: misc_feature
<222> LOCATION: (52)..(52)
<223> OTHER INFORMATION: Nucleotide N is selected independently from A,
      C, G or T
<220> FEATURE:
<221> NAME/KEY: misc_feature
<222> LOCATION: (53)..(53)
<223> OTHER INFORMATION: Nucleotide N is selected independently from A,
      C, G or T
<220> FEATURE:
<221> NAME/KEY: misc_feature
<222> LOCATION: (54)..(54)
<223> OTHER INFORMATION: Nucleotide N is selected independently from A,
      C, G or T
<220> FEATURE:
<221> NAME/KEY: misc_feature
<222> LOCATION: (57)..(62)
<223> OTHER INFORMATION: /note="EcoRI restriction enzyme sequence
      recognition"

<400> SEQUENCE: 41
gtcgagctcg tagtatcaga tcactccatn nnnnnnnnnn nnnnnnnnnn nnnnttgaat    60
tccctatagt g                                                         71
```

<210> SEQ ID NO 42
<211> LENGTH: 29
<212> TYPE: DNA
<213> ORGANISM: Artificial Sequence
<220> FEATURE:
<223> OTHER INFORMATION: 3'XhoIK
<220> FEATURE:
<221> NAME/KEY: source
<222> LOCATION: (1)..(29)
<223> OTHER INFORMATION: 3'XhoIK
<220> FEATURE:
<221> NAME/KEY: misc_feature
<222> LOCATION: (4)..(9)
<223> OTHER INFORMATION: /note="XhoI restriction enzyme sequence
      recognition"

<400> SEQUENCE: 42
gtcgagctcg tagtatcaga tcactccat                               29

<210> SEQ ID NO 43
<211> LENGTH: 33
<212> TYPE: DNA
<213> ORGANISM: Artificial Sequence
<220> FEATURE:
<223> OTHER INFORMATION: 5'T7pNL4-3
<220> FEATURE:
<221> NAME/KEY: source
<222> LOCATION: (1)..(33)
<223> OTHER INFORMATION: 5'T7pNL4-3
<220> FEATURE:
<221> NAME/KEY: misc_feature
<222> LOCATION: (1)..(20)
<223> OTHER INFORMATION: /note="T7 RNA polymerase promoter"
<220> FEATURE:
<221> NAME/KEY: misc_feature
<222> LOCATION: (20)..(30)
<223> OTHER INFORMATION: /note="nucleotides 1 to 11 from genomic RNA of
      HIV-1 strain NL4-3"

<400> SEQUENCE: 43
taatacgact cactataggg tctctctggt tag                          33

<210> SEQ ID NO 44
<211> LENGTH: 22
<212> TYPE: DNA
<213> ORGANISM: Human immunodeficiency virus type 1
<220> FEATURE:
<221> NAME/KEY: source
<222> LOCATION: (1)..(22)
<223> OTHER INFORMATION: 3'T7pNL4-3 "HIV-1 vector pNL4-3"
<220> FEATURE:
<221> NAME/KEY: misc_feature
<222> LOCATION: (1)..(22)
<223> OTHER INFORMATION: /note="nucleotides complementary to the region
      between positions 307 and 288 from the genomic RNA of HIV-1 strain
      NL4-3"

<400> SEQUENCE: 44
aatttttggc gtactcacca gt                                      22

<210> SEQ ID NO 45
<211> LENGTH: 16
<212> TYPE: RNA
<213> ORGANISM: Artificial Sequence
<220> FEATURE:
<223> OTHER INFORMATION: RNA16(-)
<220> FEATURE:
<221> NAME/KEY: source
<222> LOCATION: (1)..(16)
<223> OTHER INFORMATION: RNA16(-)

```
<400> SEQUENCE: 45
ccccgaaaac aagggg                                                  16

<210> SEQ ID NO 46
<211> LENGTH: 22
<212> TYPE: DNA
<213> ORGANISM: Artificial Sequence
<220> FEATURE:
<223> OTHER INFORMATION: 5'KpnIC3
<220> FEATURE:
<221> NAME/KEY: source
<222> LOCATION: (1)..(22)
<223> OTHER INFORMATION: 5'KpnIC3
<220> FEATURE:
<221> NAME/KEY: misc_feature
<222> LOCATION: (7)..(12)
<223> OTHER INFORMATION: /note="KpnI restriction enzyme sequence
      recognition"

<400> SEQUENCE: 46
cgactcggta ccgggaattc aa                                           22

<210> SEQ ID NO 47
<211> LENGTH: 26
<212> TYPE: DNA
<213> ORGANISM: Artificial Sequence
<220> FEATURE:
<223> OTHER INFORMATION: 3'ApaIC3
<220> FEATURE:
<221> NAME/KEY: source
<222> LOCATION: (1)..(26)
<223> OTHER INFORMATION: 3'ApaIC3
<220> FEATURE:
<221> NAME/KEY: misc_feature
<222> LOCATION: (4)..(9)
<223> OTHER INFORMATION: /note="ApaI restriction enzyme sequence
      recognition"

<400> SEQUENCE: 47
tctgggcccg tcgagctcgt agtatc                                       26

<210> SEQ ID NO 48
<211> LENGTH: 41
<212> TYPE: DNA
<213> ORGANISM: Artificial Sequence
<220> FEATURE:
<223> OTHER INFORMATION: 5'T7U6
<220> FEATURE:
<221> NAME/KEY: source
<222> LOCATION: (1)..(41)
<223> OTHER INFORMATION: 5'T7U6
<220> FEATURE:
<221> NAME/KEY: misc_feature
<222> LOCATION: (1)..(20)
<223> OTHER INFORMATION: /note="T7 RNA polymerase promoter"
<220> FEATURE:
<221> NAME/KEY: misc_feature
<222> LOCATION: (21)..(41)
<223> OTHER INFORMATION: /note="DNA sequence equivalent to that of
      nucleotides 1 to 21 from the 5' hairpin of snRNA U6"

<400> SEQUENCE: 48
taatacgact cactataggg gtcgtcgctt ctgcacgaca t                      41

<210> SEQ ID NO 49
<211> LENGTH: 30
<212> TYPE: DNA
<213> ORGANISM: Artificial Sequence
<220> FEATURE:
<223> OTHER INFORMATION: 3'ApaIU6
<220> FEATURE:
```

```
<221> NAME/KEY: source
<222> LOCATION: (1)..(30)
<223> OTHER INFORMATION: 3'ApaIU6
<220> FEATURE:
<221> NAME/KEY: misc_feature
<222> LOCATION: (4)..(9)
<223> OTHER INFORMATION: /note="ApaI restriction enzyme sequence
      recognition"
<220> FEATURE:
<221> NAME/KEY: misc_feature
<222> LOCATION: (10)..(30)
<223> OTHER INFORMATION: /note="DNA sequence equivalent to that of
      nucleotides 4 to 24 from the 3' hairpin of snRNA U6"

<400> SEQUENCE: 49
agcgggccca aaaagcggac agaagtccgc                                      30

<210> SEQ ID NO 50
<211> LENGTH: 14
<212> TYPE: RNA
<213> ORGANISM: Artificial Sequence
<220> FEATURE:
<223> OTHER INFORMATION: RNA14(+)
<220> FEATURE:
<221> NAME/KEY: source
<222> LOCATION: (1)..(14)
<223> OTHER INFORMATION: RNA14(+)

<400> SEQUENCE: 50
cccggcaagg aggg                                                       14

<210> SEQ ID NO 51
<211> LENGTH: 14
<212> TYPE: RNA
<213> ORGANISM: Artificial Sequence
<220> FEATURE:
<223> OTHER INFORMATION: RNA14(-)
<220> FEATURE:
<221> NAME/KEY: source
<222> LOCATION: (1)..(14)
<223> OTHER INFORMATION: RNA14(-)

<400> SEQUENCE: 51
cccgaaaaca aggg                                                       14

<210> SEQ ID NO 52
<211> LENGTH: 14
<212> TYPE: DNA
<213> ORGANISM: Artificial Sequence
<220> FEATURE:
<223> OTHER INFORMATION: DNA14(+)
<220> FEATURE:
<221> NAME/KEY: source
<222> LOCATION: (1)..(14)
<223> OTHER INFORMATION: DNA14(+)

<400> SEQUENCE: 52
cccggcaagg aggg                                                       14

<210> SEQ ID NO 53
<211> LENGTH: 14
<212> TYPE: DNA
<213> ORGANISM: Artificial Sequence
<220> FEATURE:
<223> OTHER INFORMATION: DNA14(+)
<220> FEATURE:
<221> NAME/KEY: source
<222> LOCATION: (1)..(14)
<223> OTHER INFORMATION: DNA14(-)

<400> SEQUENCE: 53
```

```
cccgaaaaca aggg                                                          14

<210> SEQ ID NO 54
<211> LENGTH: 64
<212> TYPE: RNA
<213> ORGANISM: Artificial Sequence
<220> FEATURE:
<223> OTHER INFORMATION: Aptamer XIV48-1

<400> SEQUENCE: 54
gggaauucaa aaccacaacg gcuaaccacu gcccaaugga gugaucugau acuacgagcu         60
cgac                                                                     64

<210> SEQ ID NO 55
<211> LENGTH: 63
<212> TYPE: RNA
<213> ORGANISM: Artificial Sequence
<220> FEATURE:
<223> OTHER INFORMATION: Aptamer XIV25-1

<400> SEQUENCE: 55
gggaauucaa cacuacucua cggcucgaag ccccaaugga gugaucugau acuacgagcc         60
gac                                                                      63

<210> SEQ ID NO 56
<211> LENGTH: 64
<212> TYPE: RNA
<213> ORGANISM: Artificial Sequence
<220> FEATURE:
<223> OTHER INFORMATION: Aptamer XIV37-1

<400> SEQUENCE: 56
gggaauucaa cacuaccgac cguccacacc agccaaugga gugaucugau acuacgagcu         60
cgac                                                                     64
```

The invention claimed is:

1. An aptamer characterized in that it comprises a structure with sequence $Mon^1$-$Mon^2$-$Mon^3$-$Mon^4$-$Mon^5$-$Mon^6$-$Mon^7$-$Mon^8$, responsible for specific binding to accessible areas in the complete folding of the 5'-UTR region of the genome of the human immunodeficiency virus HIV type 1 (HIV-1), wherein $Mon^1$ to $Mon^8$ are monomers of a nucleic acid or of a chemical analogue of nucleic acid and wherein said monomers comprise a nitrogenous base, such that the nitrogenous base of $Mon^1$ is guanine (G), the nitrogenous base of $Mon^2$ is guanine (G), the nitrogenous base of $Mon^3$ is cytosine (C), the nitrogenous base of $Mon^4$ is adenine (A), the nitrogenous base of $Mon^5$ is a purine base selected from adenine (A) or guanine (G), the nitrogenous base of $Mon^6$ is guanine (G), the nitrogenous base of $Mon^7$ is guanine (G) and the nitrogenous base of $Mon^8$ is adenine (A); and an anterior flanking region $Mon^{a4}$-$Mon^{a3}$-$Mon^{a2}$-$Mon^{a1}$- bound to the monomer $Mon^1$ and a posterior flanking region -$Mon^{b1}$-$Mon^{b2}$-$Mon^{b3}$-$Mon^{b4}$ bound to the monomer $M^8$ of said structure, wherein each flanking region comprises at least one sequence of 4 monomers of a nucleic acid or of a chemical analogue of nucleic acid, wherein the nitrogenous bases of at least 3 of the 4 monomers of the anterior flanking region closest to $Mon^1$, contiguous or not, are paired with the nitrogenous bases of at least 3 of the 4 first monomers of the posterior flanking region closest to $Mon^8$, such that the sequence structure $Mon^1$-$Mon^2$-$Mon^3$-$Mon^4$-$Mon^5$-$Mon^6$-$Mon^7$-$Mon^8$ forms a single-stranded terminal loop closing a double-stranded stem formed by the flanking regions with said paired nucleotides; or the enantiomer of said aptamer.

2. The aptamer according to claim 1, comprising a structure with the sequence $Mon^{a4}$-$Mon^{a3}$-$Mon^{a2}$-$Mon^{a1}$-$Mon^1$-$Mon^2$-$Mon^3$-$Mon^4$-$Mon^5$-$Mon^6$-$Mon^7$-$Mon^8$-$Mon^{b1}$-$Mon^{b2}$-$Mon^{b3}$-$Mon^{b4}$, wherein $Mon^{a1}$ to $Mon^{a4}$ and $Mon^{b1}$ to $Mon^{b4}$ are monomers of a nucleic acid or of a chemical analogue of nucleic acid and comprise a nitrogenous base, such that:

i. the nitrogenous bases from $Mon^{a1}$ to $Mon^{a4}$ are independently selected from the following group: A, C, G, T and U;

ii. the nitrogenous base of $Mon^{b1}$ is complementary to the nitrogenous base of $Mon^{a1}$;

iii. the nitrogenous base of $Mon^{b2}$ is complementary to the nitrogenous base of $Mon^{a2}$;

iv. the nitrogenous base of $Mon^{b3}$ is complementary to the nitrogenous base of $Mon^{a3}$;

v. the nitrogenous base of $Mon^{b4}$ is complementary to the nitrogenous base of $Mon^{a4}$;

wherein $Mon^1$ to $Mon^8$ are the monomers defined in claim 1, and wherein the complementarity rules to which these respective pairings of Mon$^{a1}$ to Mon$^{a4}$ with Mon$^{b1}$ to Mon$^{b4}$ are subjected are: A is complementary to T or U; C is complementary to G; G is complementary to C or U; T is complementary to A; U is complementary to A or G; or the enantiomer of said aptamer.

3. The aptamer according to claim 1, comprising a nucleotide sequence selected from the group consisting of: SEQ ID No: 10, SEQ ID No: 11, SEQ ID No: 12, SEQ ID No: 13, SEQ ID No: 14, SEQ ID No: 15, SEQ ID No: 16, SEQ ID No: 17, SEQ ID No: 18, SEQ ID No: 19, SEQ ID No: 20, SEQ ID No: 21, SEQ ID No: 22, SEQ ID No: 23, SEQ ID No: 24, SEQ ID No: 25, SEQ ID No: 26, SEQ ID No: 27, SEQ ID No: 28, SEQ ID No: 29, SEQ ID No: 30, SEQ ID No: 31, SEQ ID No: 32, SEQ ID No: 33, SEQ ID No: 34, SEQ ID No: 35, SEQ ID No: 36, SEQ ID No: 37 and SEQ ID No: 38; or the enantiomer of said aptamer.

4. The aptamer according to claim 1, wherein at least one of the nucleic acid monomers of said aptamer is an LNA monomer; and/or at least one of the nucleotides of said aptamer has a modification to increase resistance to nuclease degradation; or the enantiomer of said aptamer.

5. The aptamer according to claim 1, wherein the monomers of its structure are monomers of a chemical analogue of nucleic acid and said chemical analogue is one selected from the group consisting of: PNA, tPNA, GNA, p-RNA, TNA and PMO; or the enantiomer of said aptamer.

6. A DNA genetic construct useful for the synthesis by transcription, in vitro or intracellular, of an RNA aptamer defined in claim 1, characterized in that it comprises a DNA nucleotide sequence that corresponds to the sequence of nucleic acid monomers of said aptamer.

7. A method for the production of an aptamer defined in claim 1, characterized in that it comprises combining experimental techniques of in vitro selection of nucleic acids with computational optimization that allow analyzing both the sequences generated by in vitro selection and their corresponding secondary structures, comprising:
   a. obtaining RNA molecules by in vitro transcription with random sequence, of at least 25 nucleotides in length, flanked by anterior and posterior regions of constant and known sequence;
   b. selecting and isolating the RNA molecules obtained in the above step with higher affinity for the target molecule that corresponds to the 5'UTR region of HIV-1;
   c. obtaining and amplifying a cDNA obtained from the RNA molecules isolated in the preceding step;
   d. sequencing the amplified cDNA;
   e. repeating successive cycles defined by steps a-d using the product amplified in step c as a template for in vitro transcription of step a, to obtain a progressive enrichment of molecules with higher binding capacity to the target in the resulting population;
   f. classifying the cDNA sequences sequenced in the different repeated cycles a-d, comprising quantifying the nucleotide difference existing between said sequences, multiple aligning and sequence clustering or grouping of said cDNA, folding of the RNA sequence derived from the cDNA to the minimum energy structure, characterizing the minimum structural motif between sequences and analysing interactions between DNA sequences and the 5'UTR RNA target of HIV-1.

8. A method for inhibiting HIV-1 replication in a cell culture, comprising interfering the function of the 5'UTR region of the genome of HIV-1 by binding an aptamer or enantiomer thereof, defined in claim 1.

9. A method for detecting HIV-1 in vitro, comprising the specific binding of an aptamer or enantiomer thereof, defined in claim 1, to the 5'UTR region of the HIV-1 genome.

10. A method for detecting HIV-1 in a biological sample, comprising the specific binding of an aptamer or enantiomer thereof, defined in claim 1, to the 5'UTR region of the HIV-1 genome.

11. A method of treatment of a disease associated with HIV-1 infection in a subject, comprising administering a therapeutically effective amount of an aptamer or enantiomer thereof, defined in claim 1.

12. A method for inhibiting HIV-1 replication in a cell culture, comprising interfering the function of the 5'UTR region of the genome of HIV-1 by binding an aptamer characterized in that it comprises a structure with sequence Mon$^1$-Mon$^2$-Mon$^3$-Mon$^4$-Mon$^5$-Mon$^6$-Mon$^7$-Mon$^8$, responsible for specific binding to accessible areas in the complete folding of the 5'-UTR region of the genome of the human immunodeficiency virus HIV type 1 (HIV-1), wherein Mon$^1$ to Mon$^8$ are monomers of a nucleic acid or of a chemical analogue of nucleic acid and wherein said monomers comprise a nitrogenous base, such that the nitrogenous base of Mon$^1$ is guanine (G), the nitrogenous base of Mon$^2$ is guanine (G), the nitrogenous base of Mon$^3$ is cytosine (C), the nitrogenous base of Mon$^4$ is adenine (A), the nitrogenous base of Mon$^5$ is a purine base selected from adenine (A) or guanine (G), the nitrogenous base of Mon$^6$ is guanine (G), the nitrogenous base of Mon$^7$ is guanine (G) and the nitrogenous base of Mon$^8$ is adenine (A); or enantiomer thereof.

13. A method for detecting HIV-1 in vitro, comprising a specific binding of an aptamer characterized in that it comprises a structure with sequence Mon$^1$-Mon$^2$-Mon$^3$-Mon$^4$-Mon$^5$-Mon$^6$-Mon$^7$-Mon$^8$, responsible for specific binding to accessible areas in the complete folding of the 5'-UTR region of the genome of the human immunodeficiency virus HIV type 1 (HIV-1), wherein Mon$^1$ to Mon$^8$ are monomers of a nucleic acid or of a chemical analogue of nucleic acid and wherein said monomers comprise a nitrogenous base, such that the nitrogenous base of Mon$^1$ is guanine (G), the nitrogenous base of Mon$^2$ is guanine (G), the nitrogenous base of Mon$^3$ is cytosine (C), the nitrogenous base of Mon$^4$ is adenine (A), the nitrogenous base of Mon$^5$ is a purine base selected from adenine (A) or guanine (G), the nitrogenous base of Mon$^6$ is guanine (G), the nitrogenous base of Mon$^7$ is guanine (G) and the nitrogenous base of Mon$^8$ is adenine (A); or enantiomer thereof to the 5'UTR region of the HIV-1 genome or enantiomer thereof.

14. A method for detecting HIV-1 in a biological sample, comprising the specific binding of an aptamer characterized in that it comprises a structure with sequence Mon$^1$-Mon$^2$-Mon$^3$-Mon$^4$-Mon$^5$-Mon$^6$-Mon$^7$-Mon$^8$, responsible for specific binding to accessible areas in the complete folding of the 5'-UTR region of the genome of the human immunodeficiency virus HIV type 1 (HIV-1), wherein Mon$^1$ to Mon$^8$ are monomers of a nucleic acid or of a chemical analogue of nucleic acid and wherein said monomers comprise a nitrogenous base, such that the nitrogenous base of Mon$^1$ is guanine (G), the nitrogenous base of Mon$^2$ is guanine (G), the nitrogenous base of Mon$^3$ is cytosine (C), the nitrogenous base of Mon$^4$ is adenine (A), the nitrogenous base of Mon$^5$ is a purine base selected from adenine (A) or guanine (G), the nitrogenous base of Mon$^6$ is guanine (G), the nitrogenous base of Mon$^7$ is guanine (G) and the nitrogenous base of Mon$^8$ is adenine (A); or enantiomer thereof to the 5'UTR region of the HIV-1 genome.

15. A method of treatment of a disease associated with HIV-1 infection in a subject, comprising administering a therapeutically effective amount of an aptamer characterized in that it comprises a structure with sequence $Mon^1$-$Mon^2$-$Mon^3$-$Mon^4$-$Mon^5$-$Mon^6$-$Mon^7$-$Mon^8$, responsible for specific binding to accessible areas in the complete folding of the 5'-UTR region of the genome of the human immunodeficiency virus HIV type 1 (HIV-1), wherein $Mon^1$ to $Mon^8$ are monomers of a nucleic acid or of a chemical analogue of nucleic acid and wherein said monomers comprise a nitrogenous base, such that the nitrogenous base of $Mon^1$ is guanine (G), the nitrogenous base of $Mon^2$ is guanine (G), the nitrogenous base of $Mon^3$ is cytosine (C), the nitrogenous base of $Mon^4$ is adenine (A), the nitrogenous base of $Mon^5$ is a purine base selected from adenine (A) or guanine (G), the nitrogenous base of $Mon^6$ is guanine (G), the nitrogenous base of $Mon^7$ is guanine (G) and the nitrogenous base of $Mon^8$ is adenine (A); or enantiomer thereof.

* * * * *